(12) United States Patent
Zwart et al.

(10) Patent No.: US 9,730,308 B2
(45) Date of Patent: Aug. 8, 2017

(54) PARTICLE ACCELERATOR THAT PRODUCES CHARGED PARTICLES HAVING VARIABLE ENERGIES

(71) Applicant: Mevion Medical Systems, Inc., Littleton, MA (US)

(72) Inventors: Gerrit Townsend Zwart, Durham, NH (US); Charles D. O'Neal, III, Bolton, MA (US); Ken Yoshiki Franzen, Acton, MA (US)

(73) Assignee: Mevion Medical Systems, Inc., Littleton, MA (US)

( * ) Notice: Subject to any disclaimer, the term of this patent is extended or adjusted under 35 U.S.C. 154(b) by 0 days.

(21) Appl. No.: 13/916,401

(22) Filed: Jun. 12, 2013

(65) Prior Publication Data

US 2014/0371511 A1     Dec. 18, 2014

(51) Int. Cl.
*H05H 13/02* (2006.01)
*A61N 5/10* (2006.01)

(52) U.S. Cl.
CPC ........... *H05H 13/02* (2013.01); *A61N 5/1077* (2013.01); *H05H 2277/11* (2013.01)

(58) Field of Classification Search
CPC ... A61N 5/1077; H05H 13/02; H05H 2277/11
USPC ............. 315/500–507, 62; 250/493.2, 492.3, 250/492.21, 491.1, 398
See application file for complete search history.

(56) References Cited

U.S. PATENT DOCUMENTS

| | | |
|---|---|---|
| 498,915 A | 6/1893 | Heimann |
| 2,280,606 A | 4/1942 | Van et al. |
| 2,492,324 A | 12/1949 | Salisbury |
| 2,615,129 A | 10/1952 | McMillan |
| 2,616,042 A | 10/1952 | Weeks |
| 2,659,000 A | 11/1953 | Salisbury |
| 2,701,304 A | 2/1955 | Dickinson |
| 2,789,222 A | 4/1957 | Martin |
| 3,175,131 A | 3/1965 | Burleigh et al. |

(Continued)

FOREIGN PATENT DOCUMENTS

| | | |
|---|---|---|
| CA | 2354071 | 6/2000 |
| CA | 2629333 | 5/2007 |

(Continued)

OTHER PUBLICATIONS

"Beam Delivery and Properties," *Journal of the ICRU*, 2007, 7(2):20 pages.

(Continued)

*Primary Examiner* — Tuyet Vo
*Assistant Examiner* — Amy Yang
(74) *Attorney, Agent, or Firm* — Choate, Hall & Stewart LLP; Paul Pysher

(57) ABSTRACT

An example synchrocyclotron includes the following: a voltage source to provide a radio frequency (RF) voltage to a cavity to accelerate particles from a particle source; a coil to receive a variable electrical current and to generate a magnetic field that is at least 4 Tesla to cause the particles to move orbitally within the cavity; and an extraction channel to receive the accelerated particles and to output the received particles from the cavity. The particles that are output from the cavity have an energy that is variable based at least on the variable electrical current applied to the coil.

28 Claims, 15 Drawing Sheets

(56) References Cited

U.S. PATENT DOCUMENTS

| | | | |
|---|---|---|---|
| 3,432,721 A | 3/1969 | Naydan et al. | |
| 3,582,650 A | 6/1971 | Avery | |
| 3,679,899 A | 7/1972 | Dimeff | |
| 3,689,847 A | 9/1972 | Verster | |
| 3,757,118 A | 9/1973 | Hodge et al. | |
| 3,868,522 A | 2/1975 | Bigham et al. | |
| 3,886,367 A | 5/1975 | Castle, Jr. | |
| 3,925,676 A | 12/1975 | Bigham et al. | |
| 3,955,089 A | 5/1976 | McIntyre et al. | |
| 3,958,327 A | 5/1976 | Marancik et al. | |
| 3,992,625 A | 11/1976 | Schmidt et al. | |
| 4,038,622 A | 7/1977 | Purcell | |
| 4,047,068 A | 9/1977 | Ress et al. | |
| 4,112,306 A | 9/1978 | Nunan | |
| 4,129,784 A | 12/1978 | Tschunt et al. | |
| 4,139,777 A | 2/1979 | Rautenbach | |
| 4,197,510 A | 4/1980 | Szu | |
| 4,220,866 A | 9/1980 | Taumann et al. | |
| 4,230,129 A | 10/1980 | LeVeen | |
| 4,256,966 A | 3/1981 | Heinz | |
| 4,293,772 A | 10/1981 | Stieber | |
| 4,336,505 A | 6/1982 | Meyer | |
| 4,342,060 A | 7/1982 | Gibson | |
| 4,345,210 A | 8/1982 | Tran | |
| 4,353,033 A | 10/1982 | Karasawa | |
| 4,425,506 A | 1/1984 | Brown et al. | |
| 4,490,616 A | 12/1984 | Cipollina et al. | |
| 4,507,614 A | 3/1985 | Prono et al. | |
| 4,507,616 A | 3/1985 | Blosser et al. | |
| 4,589,126 A | 5/1986 | Augustsson et al. | |
| 4,598,208 A | 7/1986 | Brunelli et al. | |
| 4,628,523 A | 12/1986 | Heflin | |
| 4,633,125 A | 12/1986 | Blosser et al. | |
| 4,641,057 A | 2/1987 | Blosser et al. | |
| 4,641,104 A | 2/1987 | Blosser et al. | |
| 4,651,007 A | 3/1987 | Perusek et al. | |
| 4,680,565 A | 7/1987 | Jahnke | |
| 4,705,955 A | 11/1987 | Mileikowsky | |
| 4,710,722 A | 12/1987 | Jahnke | |
| 4,726,046 A | 2/1988 | Nunan | |
| 4,734,653 A | 3/1988 | Jahnke | |
| 4,737,727 A | 4/1988 | Yamada et al. | |
| 4,739,173 A | 4/1988 | Blosser et al. | |
| 4,745,367 A | 5/1988 | Dustmann et al. | |
| 4,754,147 A | 6/1988 | Maughan et al. | |
| 4,763,483 A | 8/1988 | Olsen | |
| 4,767,930 A | 8/1988 | Stieber et al. | |
| 4,769,623 A | 9/1988 | Marsing et al. | |
| 4,771,208 A | 9/1988 | Jongen et al. | |
| 4,783,634 A | 11/1988 | Yamamoto et al. | |
| 4,808,941 A | 2/1989 | Marsing | |
| 4,812,658 A | 3/1989 | Koehler | |
| 4,843,333 A | 6/1989 | Marsing et al. | |
| 4,845,371 A | 7/1989 | Stieber | |
| 4,865,284 A | 9/1989 | Gosis et al. | |
| 4,868,843 A | 9/1989 | Nunan | |
| 4,868,844 A | 9/1989 | Nunan | |
| 4,870,287 A | 9/1989 | Cole et al. | |
| 4,880,985 A | 11/1989 | Jones | |
| 4,894,541 A | 1/1990 | Ono | |
| 4,896,206 A | 1/1990 | Denham | |
| 4,902,993 A | 2/1990 | Krevet | |
| 4,904,949 A | 2/1990 | Wilson | |
| 4,905,267 A | 2/1990 | Miller et al. | |
| 4,917,344 A | 4/1990 | Prechter et al. | |
| 4,943,781 A | 7/1990 | Wilson et al. | |
| 4,945,478 A | 7/1990 | Merickel et al. | |
| 4,968,915 A | 11/1990 | Wilson et al. | |
| 4,987,309 A | 1/1991 | Klasen et al. | |
| 4,992,744 A | 2/1991 | Fujita et al. | |
| 4,996,496 A | 2/1991 | Kitamura et al. | |
| 5,006,759 A | 4/1991 | Krispel | |
| 5,010,562 A | 4/1991 | Hernandez et al. | |
| 5,012,111 A | 4/1991 | Ueda | |
| 5,017,789 A * | 5/1991 | Young et al. | 250/396 ML |
| 5,017,882 A | 5/1991 | Finlan | |
| 5,036,290 A | 7/1991 | Sonobe et al. | |
| 5,039,057 A | 8/1991 | Prechter et al. | |
| 5,039,867 A | 8/1991 | Nishihara et al. | |
| 5,046,078 A | 9/1991 | Hernandez et al. | |
| 5,072,123 A | 12/1991 | Johnsen | |
| 5,111,042 A | 5/1992 | Sullivan et al. | |
| 5,111,173 A | 5/1992 | Matsuda et al. | |
| 5,117,194 A | 5/1992 | Nakanishi et al. | |
| 5,117,212 A * | 5/1992 | Yamamoto | H01F 6/00 335/210 |
| 5,117,829 A | 6/1992 | Miller et al. | |
| 5,148,032 A | 9/1992 | Hernandez | |
| 5,166,531 A | 11/1992 | Huntzinger | |
| 5,189,687 A | 2/1993 | Bova et al. | |
| 5,191,706 A | 3/1993 | Cosden | |
| 5,240,218 A | 8/1993 | Dye | |
| 5,260,579 A | 11/1993 | Yasuda et al. | |
| 5,260,581 A | 11/1993 | Lesyna et al. | |
| 5,278,533 A | 1/1994 | Kawaguchi | |
| 5,285,166 A | 2/1994 | Hiramoto et al. | |
| 5,317,164 A | 5/1994 | Kurokawa | |
| 5,336,891 A | 8/1994 | Crewe | |
| 5,341,104 A | 8/1994 | Anton et al. | |
| 5,349,198 A | 9/1994 | Takanaka | |
| 5,365,742 A | 11/1994 | Boffito et al. | |
| 5,374,913 A | 12/1994 | Pissantezky et al. | |
| 5,382,914 A | 1/1995 | Hamm et al. | |
| 5,401,973 A | 3/1995 | McKeown et al. | |
| 5,405,235 A | 4/1995 | Lebre et al. | |
| 5,434,420 A | 7/1995 | McKeown et al. | |
| 5,440,133 A | 8/1995 | Moyers et al. | |
| 5,451,794 A | 9/1995 | McKeown et al. | |
| 5,461,773 A | 10/1995 | Kawaguchi | |
| 5,463,291 A | 10/1995 | Carroll et al. | |
| 5,464,411 A | 11/1995 | Schulte et al. | |
| 5,492,922 A | 2/1996 | Palkowitz | |
| 5,511,549 A | 4/1996 | Legg et al. | |
| 5,521,469 A | 5/1996 | Laisne | |
| 5,538,942 A | 7/1996 | Koyama et al. | |
| 5,549,616 A | 8/1996 | Schulte et al. | |
| 5,561,697 A | 10/1996 | Takafuji et al. | |
| 5,585,642 A | 12/1996 | Britton et al. | |
| 5,633,747 A | 5/1997 | Nikoonahad | |
| 5,635,721 A | 6/1997 | Bardi et al. | |
| 5,668,371 A | 9/1997 | Deasy et al. | |
| 5,672,878 A | 9/1997 | Yao | |
| 5,691,679 A | 11/1997 | Ackermann et al. | |
| 5,717,371 A | 2/1998 | Crow | |
| 5,726,448 A | 3/1998 | Smith et al. | |
| 5,727,554 A | 3/1998 | Kalend et al. | |
| 5,730,745 A | 3/1998 | Schulte et al. | |
| 5,739,646 A * | 4/1998 | Nakanishi | H05H 13/00 313/62 |
| 5,751,781 A | 5/1998 | Brown et al. | |
| 5,778,047 A | 7/1998 | Mansfield et al. | |
| 5,783,914 A | 7/1998 | Hiramoto et al. | |
| 5,784,431 A | 7/1998 | Kalend et al. | |
| 5,797,924 A | 8/1998 | Schulte et al. | |
| 5,811,944 A | 9/1998 | Sampayan et al. | |
| 5,818,058 A | 10/1998 | Nakanishi et al. | |
| 5,821,705 A | 10/1998 | Caporaso et al. | |
| 5,825,845 A | 10/1998 | Blair et al. | |
| 5,841,237 A | 11/1998 | Alton | |
| 5,846,043 A | 12/1998 | Spath | |
| 5,851,182 A | 12/1998 | Sahadevan | |
| 5,866,912 A | 2/1999 | Slater et al. | |
| 5,874,811 A | 2/1999 | Finlan et al. | |
| 5,895,926 A | 4/1999 | Britton et al. | |
| 5,920,601 A | 7/1999 | Nigg et al. | |
| 5,929,458 A | 7/1999 | Nemezawa et al. | |
| 5,963,615 A | 10/1999 | Egley et al. | |
| 5,993,373 A | 11/1999 | Nonaka et al. | |
| 6,008,499 A | 12/1999 | Hiramoto et al. | |
| 6,034,377 A | 3/2000 | Pu | |
| 6,057,655 A | 5/2000 | Jongen | |
| 6,061,426 A | 5/2000 | Linders et al. | |
| 6,064,807 A | 5/2000 | Arai et al. | |
| 6,066,851 A | 5/2000 | Madono et al. | |

(56) References Cited

U.S. PATENT DOCUMENTS

| | | |
|---|---|---|
| 6,080,992 A | 6/2000 | Nonaka et al. |
| 6,087,670 A | 7/2000 | Hiramoto et al. |
| 6,094,760 A | 8/2000 | Nonaka et al. |
| 6,118,848 A | 9/2000 | Reiffel |
| 6,140,021 A | 10/2000 | Nakasuji et al. |
| 6,144,875 A | 11/2000 | Schweikard et al. |
| 6,158,708 A | 12/2000 | Egley et al. |
| 6,207,952 B1 | 3/2001 | Kan et al. |
| 6,219,403 B1 | 4/2001 | Nishihara |
| 6,222,905 B1 | 4/2001 | Yoda et al. |
| 6,241,671 B1 | 6/2001 | Ritter et al. |
| 6,246,066 B1 | 6/2001 | Yuehu |
| 6,256,591 B1 | 7/2001 | Yoda et al. |
| 6,265,837 B1 | 7/2001 | Akiyama et al. |
| 6,268,610 B1 | 7/2001 | Pu |
| 6,278,239 B1 | 8/2001 | Caporaso et al. |
| 6,279,579 B1 | 8/2001 | Riaziat et al. |
| 6,307,914 B1 | 10/2001 | Kunieda et al. |
| 6,316,776 B1 | 11/2001 | Hiramoto et al. |
| 6,366,021 B1 | 4/2002 | Meddaugh et al. |
| 6,369,585 B2 | 4/2002 | Yao |
| 6,380,545 B1 | 4/2002 | Yan |
| 6,407,505 B1 | 6/2002 | Bertsche |
| 6,417,634 B1 | 7/2002 | Bergstrom |
| 6,433,336 B1 | 8/2002 | Jongen et al. |
| 6,433,349 B2 | 8/2002 | Akiyama et al. |
| 6,433,494 B1 | 8/2002 | Kulish et al. |
| 6,441,569 B1 | 8/2002 | Janzow |
| 6,443,349 B1 | 9/2002 | Van Der Burg |
| 6,465,957 B1 | 10/2002 | Whitham et al. |
| 6,472,834 B2 | 10/2002 | Hiramoto et al. |
| 6,476,403 B1 | 11/2002 | Dolinskii et al. |
| 6,492,922 B1 | 12/2002 | New |
| 6,493,424 B2 | 12/2002 | Whitham |
| 6,498,444 B1 | 12/2002 | Hanna et al. |
| 6,501,961 B1 | 12/2002 | Kirkpatrick |
| 6,501,981 B1 | 12/2002 | Schweikard et al. |
| 6,519,316 B1 | 2/2003 | Collins |
| 6,593,696 B2 | 7/2003 | Ding et al. |
| 6,594,336 B2 | 7/2003 | Nishizawa et al. |
| 6,600,164 B1 | 7/2003 | Badura et al. |
| 6,617,598 B1 | 9/2003 | Matsuda |
| 6,621,889 B1 | 9/2003 | Mostafavi |
| 6,639,234 B1 | 10/2003 | Badura et al. |
| 6,646,383 B2 | 11/2003 | Bertsche et al. |
| 6,670,618 B1 | 12/2003 | Hartmann et al. |
| 6,683,318 B1 | 1/2004 | Haberer et al. |
| 6,683,426 B1 | 1/2004 | Kleeven |
| 6,693,283 B2 | 2/2004 | Eickhoff et al. |
| 6,710,362 B2 | 3/2004 | Kraft et al. |
| 6,713,773 B1 | 3/2004 | Lyons et al. |
| 6,713,976 B1 | 3/2004 | Zumoto et al. |
| 6,717,162 B1 | 4/2004 | Jongen |
| 6,736,831 B1 | 5/2004 | Hartmann et al. |
| 6,745,072 B1 | 6/2004 | Badura et al. |
| 6,769,806 B2 | 8/2004 | Moyers |
| 6,774,383 B2 | 8/2004 | Norimine et al. |
| 6,777,689 B2 | 8/2004 | Nelson |
| 6,777,700 B2 | 8/2004 | Yanagisawa et al. |
| 6,780,149 B1 | 8/2004 | Schulte |
| 6,799,068 B1 | 9/2004 | Hartmann et al. |
| 6,800,866 B2 | 10/2004 | Amemiya et al. |
| 6,803,591 B2 | 10/2004 | Yamashita et al. |
| 6,814,694 B1 | 11/2004 | Pedroni |
| 6,822,244 B2 | 11/2004 | Beloussov et al. |
| 6,853,703 B2 | 2/2005 | Svatos et al. |
| 6,864,770 B2 | 3/2005 | Nemoto et al. |
| 6,865,254 B2 | 3/2005 | Nafstadius |
| 6,873,123 B2 | 3/2005 | Marchand et al. |
| 6,891,177 B1 | 5/2005 | Kraft et al. |
| 6,891,924 B1 | 5/2005 | Yoda et al. |
| 6,894,300 B2 | 5/2005 | Reimoser et al. |
| 6,897,451 B2 | 5/2005 | Kaercher et al. |
| 6,914,396 B1 | 7/2005 | Symons et al. |
| 6,936,832 B2 | 8/2005 | Norimine et al. |
| 6,953,943 B2 | 10/2005 | Yanagisawa et al. |
| 6,965,116 B1 | 11/2005 | Wagner et al. |
| 6,969,194 B1 | 11/2005 | Nafstadius |
| 6,979,832 B2 | 12/2005 | Yanagisawa et al. |
| 6,984,835 B2 | 1/2006 | Harada |
| 6,992,312 B2 | 1/2006 | Yanagisawa et al. |
| 6,993,112 B2 | 1/2006 | Hesse |
| 7,008,105 B2 | 3/2006 | Amann et al. |
| 7,011,447 B2 | 3/2006 | Moyers |
| 7,012,267 B2 | 3/2006 | Moriyama et al. |
| 7,014,361 B1 | 3/2006 | Ein-Gal |
| 7,026,636 B2 | 4/2006 | Yanagisawa et al. |
| 7,038,403 B2 | 5/2006 | Mastrangeli et al. |
| 7,041,479 B2 | 5/2006 | Swartz et al. |
| 7,045,781 B2 | 5/2006 | Adamec et al. |
| 7,049,613 B2 | 5/2006 | Yanagisawa et al. |
| 7,053,389 B2 | 5/2006 | Yanagisawa et al. |
| 7,054,801 B2 | 5/2006 | Sakamoto et al. |
| 7,060,997 B2 | 6/2006 | Norimine et al. |
| 7,071,479 B2 | 7/2006 | Yanagisawa et al. |
| 7,073,508 B2 | 7/2006 | Moyers |
| 7,081,619 B2 | 7/2006 | Bashkirov et al. |
| 7,084,410 B2 | 8/2006 | Beloussov et al. |
| 7,091,478 B2 | 8/2006 | Haberer |
| 7,102,144 B2 | 9/2006 | Matsuda et al. |
| 7,122,811 B2 | 10/2006 | Matsuda et al. |
| 7,122,966 B2 | 10/2006 | Norling et al. |
| 7,122,978 B2 | 10/2006 | Nakanishi et al. |
| 7,135,678 B2 | 11/2006 | Wang et al. |
| 7,138,771 B2 | 11/2006 | Bechthold et al. |
| 7,154,107 B2 | 12/2006 | Yanagisawa et al. |
| 7,154,108 B2 | 12/2006 | Tadokoro et al. |
| 7,154,991 B2 | 12/2006 | Earnst et al. |
| 7,162,005 B2 | 1/2007 | Bjorkholm |
| 7,173,264 B2 | 2/2007 | Moriyama et al. |
| 7,173,265 B2 | 2/2007 | Miller et al. |
| 7,173,385 B2 | 2/2007 | Caporaso et al. |
| 7,186,991 B2 | 3/2007 | Kato et al. |
| 7,193,227 B2 | 3/2007 | Hiramoto et al. |
| 7,199,382 B2 | 4/2007 | Rigney et al. |
| 7,208,748 B2 | 4/2007 | Sliski et al. |
| 7,212,608 B2 | 5/2007 | Nagamine et al. |
| 7,212,609 B2 | 5/2007 | Nagamine et al. |
| 7,221,733 B1 | 5/2007 | Takai et al. |
| 7,227,161 B2 | 6/2007 | Matsuda et al. |
| 7,247,869 B2 | 7/2007 | Tadokoro et al. |
| 7,257,191 B2 | 8/2007 | Sommer |
| 7,259,529 B2 | 8/2007 | Tanaka |
| 7,262,424 B2 | 8/2007 | Moriyama et al. |
| 7,262,565 B2 | 8/2007 | Fujisawa |
| 7,274,018 B2 | 9/2007 | Adamec et al. |
| 7,280,633 B2 | 10/2007 | Cheng et al. |
| 7,295,649 B2 | 11/2007 | Johnsen |
| 7,297,967 B2 | 11/2007 | Yanagisawa et al. |
| 7,301,162 B2 | 11/2007 | Matsuda et al. |
| 7,307,264 B2 | 12/2007 | Brusasco et al. |
| 7,318,805 B2 | 1/2008 | Schweikard et al. |
| 7,319,231 B2 | 1/2008 | Moriyama et al. |
| 7,319,336 B2 | 1/2008 | Baur et al. |
| 7,331,713 B2 | 2/2008 | Moyers |
| 7,332,880 B2 | 2/2008 | Ina et al. |
| 7,345,291 B2 | 3/2008 | Kats |
| 7,345,292 B2 | 3/2008 | Moriyama et al. |
| 7,348,557 B2 | 3/2008 | Armit |
| 7,348,579 B2 | 3/2008 | Pedroni |
| 7,351,988 B2 | 4/2008 | Naumann et al. |
| 7,355,189 B2 | 4/2008 | Yanagisawa et al. |
| 7,368,740 B2 | 5/2008 | Beloussov et al. |
| 7,372,053 B2 | 5/2008 | Yamashita et al. |
| 7,378,672 B2 | 5/2008 | Harada |
| 7,381,979 B2 | 6/2008 | Yamashita et al. |
| 7,397,054 B2 | 7/2008 | Natori et al. |
| 7,397,901 B1 | 7/2008 | Johnsen |
| 7,398,309 B2 | 7/2008 | Baumann et al. |
| 7,402,822 B2 | 7/2008 | Guertin et al. |
| 7,402,823 B2 | 7/2008 | Guertin et al. |
| 7,402,824 B2 | 7/2008 | Guertin et al. |
| 7,402,963 B2 | 7/2008 | Sliski |
| 7,405,407 B2 | 7/2008 | Hiramoto et al. |

(56) References Cited

U.S. PATENT DOCUMENTS

| | | |
|---|---|---|
| 7,425,717 B2 | 9/2008 | Matsuda et al. |
| 7,432,516 B2 | 10/2008 | Peggs et al. |
| 7,439,528 B2 | 10/2008 | Nishiuchi et al. |
| 7,446,328 B2 | 11/2008 | Rigney et al. |
| 7,446,490 B2 | 11/2008 | Jongen et al. |
| 7,449,701 B2 | 11/2008 | Fujimaki et al. |
| 7,453,076 B2 | 11/2008 | Welch et al. |
| 7,465,944 B2 | 12/2008 | Ueno et al. |
| 7,466,085 B2 | 12/2008 | Nutt |
| 7,468,506 B2 | 12/2008 | Rogers et al. |
| 7,473,913 B2 | 1/2009 | Hermann et al. |
| 7,476,867 B2 | 1/2009 | Fritsch et al. |
| 7,476,883 B2 | 1/2009 | Nutt |
| 7,482,606 B2 | 1/2009 | Groezinger et al. |
| 7,492,556 B2 | 2/2009 | Atkins et al. |
| 7,507,975 B2 | 3/2009 | Mohr |
| 7,525,104 B2 | 4/2009 | Harada |
| 7,541,905 B2 | 6/2009 | Antaya |
| 7,547,901 B2 | 6/2009 | Guertin et al. |
| 7,554,096 B2 | 6/2009 | Ward et al. |
| 7,554,097 B2 | 6/2009 | Ward et al. |
| 7,555,103 B2 | 6/2009 | Johnsen |
| 7,557,358 B2 | 7/2009 | Ward et al. |
| 7,557,359 B2 | 7/2009 | Ward et al. |
| 7,557,360 B2 | 7/2009 | Ward et al. |
| 7,557,361 B2 | 7/2009 | Ward et al. |
| 7,560,715 B2 | 7/2009 | Pedroni |
| 7,560,717 B2 | 7/2009 | Matsuda et al. |
| 7,567,694 B2 | 7/2009 | Lu et al. |
| 7,574,251 B2 | 8/2009 | Lu et al. |
| 7,576,499 B2 | 8/2009 | Caporaso et al. |
| 7,579,603 B2 | 8/2009 | Birgy et al. |
| 7,579,610 B2 | 8/2009 | Grozinger et al. |
| 7,582,866 B2 | 9/2009 | Furuhashi et al. |
| 7,582,885 B2 | 9/2009 | Katagiri et al. |
| 7,582,886 B2 | 9/2009 | Trbojevic |
| 7,586,112 B2 | 9/2009 | Chiba et al. |
| 7,598,497 B2 | 10/2009 | Yamamoto et al. |
| 7,609,009 B2 | 10/2009 | Tanaka et al. |
| 7,609,809 B2 | 10/2009 | Kapatoes et al. |
| 7,609,811 B1 | 10/2009 | Siljamaki et al. |
| 7,615,942 B2 | 11/2009 | Sanders et al. |
| 7,629,598 B2 | 12/2009 | Harada |
| 7,639,853 B2 | 12/2009 | Olivera et al. |
| 7,639,854 B2 | 12/2009 | Schnarr et al. |
| 7,643,661 B2 | 1/2010 | Ruchala et al. |
| 7,656,258 B1 | 2/2010 | Antaya et al. |
| 7,659,521 B2 | 2/2010 | Pedroni |
| 7,659,528 B2 | 2/2010 | Uematsu |
| 7,668,291 B2 | 2/2010 | Nord et al. |
| 7,672,429 B2 | 3/2010 | Urano et al. |
| 7,679,073 B2 | 3/2010 | Urano et al. |
| 7,682,078 B2 | 3/2010 | Rietzel |
| 7,692,166 B2 | 4/2010 | Muraki et al. |
| 7,692,168 B2 | 4/2010 | Moriyama et al. |
| 7,696,499 B2 | 4/2010 | Miller et al. |
| 7,696,847 B2 | 4/2010 | Antaya |
| 7,701,677 B2 | 4/2010 | Schultz et al. |
| 7,709,818 B2 | 5/2010 | Matsuda et al. |
| 7,710,051 B2 | 5/2010 | Caporaso et al. |
| 7,728,311 B2 | 6/2010 | Gall |
| 7,746,978 B2 | 6/2010 | Cheng et al. |
| 7,755,305 B2 | 7/2010 | Umezawa et al. |
| 7,759,642 B2 | 7/2010 | Nir |
| 7,763,867 B2 | 7/2010 | Birgy et al. |
| 7,767,988 B2 | 8/2010 | Kaiser et al. |
| 7,770,231 B2 | 8/2010 | Prater et al. |
| 7,772,577 B2 | 8/2010 | Saito et al. |
| 7,773,723 B2 | 8/2010 | Nord et al. |
| 7,773,788 B2 | 8/2010 | Lu et al. |
| 7,778,488 B2 | 8/2010 | Nord et al. |
| 7,783,010 B2 | 8/2010 | Clayton |
| 7,784,127 B2 | 8/2010 | Kuro et al. |
| 7,786,451 B2 | 8/2010 | Ward et al. |
| 7,786,452 B2 | 8/2010 | Ward et al. |
| 7,789,560 B2 | 9/2010 | Moyers |
| 7,791,051 B2 | 9/2010 | Beloussov et al. |
| 7,796,731 B2 | 9/2010 | Nord et al. |
| 7,801,269 B2 | 9/2010 | Cravens et al. |
| 7,801,270 B2 | 9/2010 | Nord et al. |
| 7,801,988 B2 | 9/2010 | Baumann et al. |
| 7,807,982 B2 | 10/2010 | Nishiuchi et al. |
| 7,809,107 B2 | 10/2010 | Nord et al. |
| 7,812,319 B2 | 10/2010 | Diehl et al. |
| 7,812,326 B2 | 10/2010 | Grozinger et al. |
| 7,816,657 B2 | 10/2010 | Hansmann et al. |
| 7,817,778 B2 | 10/2010 | Nord et al. |
| 7,817,836 B2 | 10/2010 | Chao et al. |
| 7,834,334 B2 | 11/2010 | Grozinger et al. |
| 7,834,336 B2 | 11/2010 | Boeh et al. |
| 7,835,494 B2 | 11/2010 | Nord et al. |
| 7,835,502 B2 | 11/2010 | Spence et al. |
| 7,839,972 B2 | 11/2010 | Ruchala et al. |
| 7,839,973 B2 | 11/2010 | Nord et al. |
| 7,848,488 B2 | 12/2010 | Mansfield |
| 7,857,756 B2 | 12/2010 | Warren et al. |
| 7,860,216 B2 | 12/2010 | Jongen et al. |
| 7,860,550 B2 | 12/2010 | Saracen et al. |
| 7,868,301 B2 | 1/2011 | Diehl |
| 7,875,801 B2 | 1/2011 | Tsotsis |
| 7,875,861 B2 | 1/2011 | Huttenberger et al. |
| 7,875,868 B2 | 1/2011 | Moriyama et al. |
| 7,881,431 B2 | 2/2011 | Aoi et al. |
| 7,894,574 B1 | 2/2011 | Nord et al. |
| 7,906,769 B2 | 3/2011 | Blasche et al. |
| 7,914,734 B2 | 3/2011 | Livingston |
| 7,919,765 B2 | 4/2011 | Timmer |
| 7,920,040 B2 | 4/2011 | Antaya et al. |
| 7,920,675 B2 | 4/2011 | Lomax et al. |
| 7,928,415 B2 | 4/2011 | Bert et al. |
| 7,934,869 B2 | 5/2011 | Ivanov et al. |
| 7,940,881 B2 | 5/2011 | Jongen et al. |
| 7,943,913 B2 | 5/2011 | Balakin |
| 7,947,969 B2 | 5/2011 | Pu |
| 7,949,096 B2 | 5/2011 | Cheng et al. |
| 7,950,587 B2 | 5/2011 | Henson et al. |
| 7,960,710 B2 | 6/2011 | Kruip et al. |
| 7,961,844 B2 | 6/2011 | Takeda et al. |
| 7,977,648 B2 | 7/2011 | Westerly et al. |
| 7,977,656 B2 | 7/2011 | Fujimaki et al. |
| 7,982,198 B2 | 7/2011 | Nishiuchi et al. |
| 7,982,416 B2 | 7/2011 | Tanaka et al. |
| 7,984,715 B2 | 7/2011 | Moyers |
| 7,986,768 B2 | 7/2011 | Nord et al. |
| 7,987,053 B2 | 7/2011 | Schaffner |
| 7,989,785 B2 | 8/2011 | Emhofer et al. |
| 7,990,524 B2 | 8/2011 | Jureller et al. |
| 7,997,553 B2 | 8/2011 | Sloan et al. |
| 8,002,466 B2 | 8/2011 | Von Neubeck et al. |
| 8,003,964 B2 | 8/2011 | Stark et al. |
| 8,009,803 B2 | 8/2011 | Nord et al. |
| 8,009,804 B2 | 8/2011 | Siljamaki et al. |
| 8,039,822 B2 | 10/2011 | Rietzel |
| 8,041,006 B2 | 10/2011 | Boyden et al. |
| 8,044,364 B2 | 10/2011 | Yamamoto |
| 8,049,187 B2 | 11/2011 | Tachikawa |
| 8,053,508 B2 | 11/2011 | Korkut et al. |
| 8,053,739 B2 | 11/2011 | Rietzel |
| 8,053,745 B2 | 11/2011 | Moore |
| 8,053,746 B2 | 11/2011 | Timmer et al. |
| 8,067,748 B2 | 11/2011 | Balakin |
| 8,069,675 B2 | 12/2011 | Radovinsky et al. |
| 8,071,966 B2 | 12/2011 | Kaiser et al. |
| 8,080,801 B2 | 12/2011 | Safai |
| 8,085,899 B2 | 12/2011 | Nord et al. |
| 8,089,054 B2 | 1/2012 | Balakin |
| 8,093,564 B2 | 1/2012 | Balakin |
| 8,093,568 B2 | 1/2012 | Mackie et al. |
| 8,111,125 B2 | 2/2012 | Antaya et al. |
| 8,129,699 B2 | 3/2012 | Balakin |
| 8,144,832 B2 | 3/2012 | Balakin |
| 8,173,981 B2 | 5/2012 | Trbojevic |
| 8,188,688 B2 | 5/2012 | Balakin |
| 8,198,607 B2 | 6/2012 | Balakin |

(56) References Cited

U.S. PATENT DOCUMENTS

| | | | |
|---|---|---|---|
| 8,222,613 B2 | 7/2012 | Tajiri et al. | |
| 8,227,768 B2 | 7/2012 | Smick et al. | |
| 8,232,536 B2 | 7/2012 | Harada | |
| 8,288,742 B2 | 10/2012 | Balakin | |
| 8,291,717 B2 | 10/2012 | Radovinsky et al. | |
| 8,294,127 B2 | 10/2012 | Tachibana | |
| 8,304,725 B2 | 11/2012 | Komuro et al. | |
| 8,304,750 B2 | 11/2012 | Preikszas et al. | |
| 8,309,941 B2 | 11/2012 | Balakin | |
| 8,330,132 B2 | 12/2012 | Guertin et al. | |
| 8,334,520 B2 | 12/2012 | Otaka et al. | |
| 8,335,397 B2 | 12/2012 | Takane et al. | |
| 8,344,340 B2 | 1/2013 | Gall et al. | |
| 8,350,214 B2 | 1/2013 | Otaki et al. | |
| 8,368,038 B2 | 2/2013 | Balakin | |
| 8,368,043 B2 | 2/2013 | Havelange et al. | |
| 8,373,143 B2 | 2/2013 | Balakin | |
| 8,373,145 B2 | 2/2013 | Balakin | |
| 8,378,299 B2 | 2/2013 | Frosien | |
| 8,378,321 B2 | 2/2013 | Balakin | |
| 8,382,943 B2 | 2/2013 | Clark | |
| 8,389,949 B2 | 3/2013 | Harada et al. | |
| 8,399,866 B2 | 3/2013 | Balakin | |
| 8,405,042 B2 | 3/2013 | Honda et al. | |
| 8,405,056 B2 | 3/2013 | Amaldi et al. | |
| 8,415,643 B2 | 4/2013 | Balakin | |
| 8,416,918 B2 | 4/2013 | Nord et al. | |
| 8,421,041 B2 | 4/2013 | Balakin | |
| 8,426,833 B2* | 4/2013 | Trbojevic | 250/493.1 |
| 8,436,323 B2 | 5/2013 | Iseki et al. | |
| 8,440,987 B2 | 5/2013 | Stephani et al. | |
| 8,445,872 B2 | 5/2013 | Behrens et al. | |
| 8,466,441 B2 | 6/2013 | Iwata et al. | |
| 8,472,583 B2 | 6/2013 | Star-Lack et al. | |
| 8,483,357 B2 | 7/2013 | Siljamaki et al. | |
| 8,487,278 B2 | 7/2013 | Balakin | |
| 8,552,406 B2 | 10/2013 | Phaneuf et al. | |
| 8,552,408 B2 | 10/2013 | Hanawa et al. | |
| 8,569,717 B2 | 10/2013 | Balakin | |
| 8,581,215 B2 | 11/2013 | Balakin | |
| 8,581,523 B2* | 11/2013 | Gall et al. | 315/501 |
| 8,581,525 B2 | 11/2013 | Antaya et al. | |
| 8,653,314 B2 | 2/2014 | Pelati et al. | |
| 8,653,473 B2 | 2/2014 | Yajima | |
| 8,791,656 B1 | 7/2014 | Zwart et al. | |
| 8,975,836 B2 | 3/2015 | Bromberg et al. | |
| 2002/0172317 A1 | 11/2002 | Maksimchuk et al. | |
| 2003/0048080 A1 | 3/2003 | Amemiya et al. | |
| 2003/0125622 A1 | 7/2003 | Schweikard et al. | |
| 2003/0136924 A1 | 7/2003 | Kraft et al. | |
| 2003/0152197 A1 | 8/2003 | Moyers | |
| 2003/0163015 A1 | 8/2003 | Yanagisawa et al. | |
| 2003/0183779 A1 | 10/2003 | Norimine et al. | |
| 2003/0234369 A1 | 12/2003 | Glukhoy | |
| 2004/0000650 A1 | 1/2004 | Yanagisawa et al. | |
| 2004/0017888 A1 | 1/2004 | Seppi et al. | |
| 2004/0056212 A1 | 3/2004 | Yanagisawa et al. | |
| 2004/0061077 A1 | 4/2004 | Muramatsu et al. | |
| 2004/0061078 A1 | 4/2004 | Muramatsu et al. | |
| 2004/0085023 A1 | 5/2004 | Chistyakov | |
| 2004/0098445 A1 | 5/2004 | Baumann et al. | |
| 2004/0111134 A1 | 6/2004 | Muramatsu et al. | |
| 2004/0118081 A1 | 6/2004 | Reimoser et al. | |
| 2004/0149934 A1 | 8/2004 | Yanagisawa et al. | |
| 2004/0159795 A1 | 8/2004 | Kaercher et al. | |
| 2004/0173763 A1 | 9/2004 | Moriyama et al. | |
| 2004/0174958 A1 | 9/2004 | Moriyama et al. | |
| 2004/0183033 A1 | 9/2004 | Moriyama et al. | |
| 2004/0183035 A1 | 9/2004 | Yanagisawa et al. | |
| 2004/0200982 A1 | 10/2004 | Moriyama et al. | |
| 2004/0200983 A1 | 10/2004 | Fujimaki et al. | |
| 2004/0213381 A1 | 10/2004 | Harada | |
| 2004/0227104 A1 | 11/2004 | Matsuda et al. | |
| 2004/0232356 A1 | 11/2004 | Norimine et al. | |
| 2004/0240626 A1 | 12/2004 | Moyers | |
| 2005/0058245 A1 | 3/2005 | Ein-Gal | |
| 2005/0089141 A1 | 4/2005 | Brown | |
| 2005/0161618 A1 | 7/2005 | Pedroni | |
| 2005/0184686 A1 | 8/2005 | Caporaso et al. | |
| 2005/0228255 A1 | 10/2005 | Saracen et al. | |
| 2005/0234327 A1 | 10/2005 | Saracen et al. | |
| 2005/0247890 A1 | 11/2005 | Norimine et al. | |
| 2006/0017015 A1 | 1/2006 | Sliski et al. | |
| 2006/0067468 A1 | 3/2006 | Rietzel | |
| 2006/0126792 A1 | 6/2006 | Li | |
| 2006/0145088 A1 | 7/2006 | Ma | |
| 2006/0284562 A1 | 12/2006 | Hruby et al. | |
| 2007/0001128 A1* | 1/2007 | Sliski | H05H 13/02 |
| | | | 250/492.3 |
| 2007/0013273 A1 | 1/2007 | Albert et al. | |
| 2007/0014654 A1 | 1/2007 | Haverfield et al. | |
| 2007/0023699 A1 | 2/2007 | Yamashita et al. | |
| 2007/0029510 A1 | 2/2007 | Hermann et al. | |
| 2007/0051904 A1 | 3/2007 | Kaiser et al. | |
| 2007/0092812 A1 | 4/2007 | Caporaso et al. | |
| 2007/0061937 A1 | 5/2007 | Gall | |
| 2007/0114945 A1 | 5/2007 | Mattaboni et al. | |
| 2007/0145916 A1 | 6/2007 | Caporaso et al. | |
| 2007/0171015 A1 | 7/2007 | Antaya | |
| 2007/0181519 A1 | 8/2007 | Khoshnevis | |
| 2007/0228304 A1* | 10/2007 | Nishiuchi | A61N 5/1043 |
| | | | 250/505.1 |
| 2007/0284548 A1 | 12/2007 | Kaiser et al. | |
| 2008/0093567 A1 | 4/2008 | Gall | |
| 2008/0218102 A1 | 9/2008 | Sliski | |
| 2009/0096179 A1 | 4/2009 | Stark et al. | |
| 2009/0140671 A1 | 6/2009 | O'Neal et al. | |
| 2009/0140672 A1 | 6/2009 | Gall et al. | |
| 2009/0200483 A1 | 8/2009 | Gall et al. | |
| 2010/0022710 A1 | 1/2010 | Xie et al. | |
| 2010/0045213 A1* | 2/2010 | Sliski et al. | 315/502 |
| 2010/0230617 A1* | 9/2010 | Gall | 250/492.21 |
| 2012/0142538 A1 | 6/2012 | Antaya et al. | |
| 2012/0217903 A1* | 8/2012 | Tanaka | H05H 7/12 |
| | | | 315/502 |
| 2013/0009571 A1 | 1/2013 | Antaya | |
| 2013/0053616 A1 | 2/2013 | Gall et al. | |
| 2013/0237425 A1 | 9/2013 | Leigh et al. | |
| 2014/0028220 A1* | 1/2014 | Bromberg et al. | 315/502 |
| 2014/0042934 A1 | 2/2014 | Tsutsui | |
| 2014/0097920 A1 | 4/2014 | Goldie et al. | |
| 2014/0320006 A1* | 10/2014 | Abs | H05H 7/02 |
| | | | 315/39.51 |

FOREIGN PATENT DOCUMENTS

| | | |
|---|---|---|
| CN | 1537657 A | 10/2004 |
| CN | 101932361 | 12/2010 |
| CN | 101933405 | 12/2010 |
| CN | 101933406 | 12/2010 |
| CN | 101061759 | 5/2011 |
| CN | 104244562 A | 12/2014 |
| DE | 2753397 | 6/1978 |
| DE | 31 48 100 | 6/1983 |
| DE | 35 30 446 | 8/1984 |
| DE | 41 01 094 C1 | 5/1992 |
| DE | 4411171 | 10/1995 |
| EP | 0 194 728 | 9/1986 |
| EP | 0276123 | 7/1988 |
| EP | 0 277 521 | 8/1988 |
| EP | 0 208 163 | 1/1989 |
| EP | 0 222 786 | 7/1990 |
| EP | 0 221 987 | 1/1991 |
| EP | 0 499 253 | 8/1992 |
| EP | 0 306 966 | 4/1995 |
| EP | 0 388 123 | 5/1995 |
| EP | 0 465 597 | 5/1997 |
| EP | 0 911 064 | 6/1998 |
| EP | 0 864 337 | 9/1998 |
| EP | 0 776 595 | 12/1998 |
| EP | 1 069 809 | 1/2001 |
| EP | 1 153 398 | 4/2001 |
| EP | 1 294 445 | 3/2003 |

(56) References Cited

FOREIGN PATENT DOCUMENTS

| | | |
|---|---|---|
| EP | 1 348 465 | 10/2003 |
| EP | 1 358 908 | 11/2003 |
| EP | 1 371 390 | 12/2003 |
| EP | 1 402 923 | 3/2004 |
| EP | 1 430 932 | 6/2004 |
| EP | 1 454 653 | 9/2004 |
| EP | 1 454 654 | 9/2004 |
| EP | 1 454 655 | 9/2004 |
| EP | 1 454 656 | 9/2004 |
| EP | 1 454 657 | 9/2004 |
| EP | 1 477 206 | 11/2004 |
| EP | 1 738 798 | 1/2007 |
| EP | 1 826 778 | 8/2007 |
| EP | 1 949 404 | 7/2008 |
| EP | 2183753 | 7/2008 |
| EP | 2394498 | 2/2010 |
| EP | 2232961 | 9/2010 |
| EP | 2232962 | 9/2010 |
| EP | 2227295 | 5/2011 |
| EP | 1 605 742 | 6/2011 |
| EP | 2363170 | 9/2011 |
| EP | 2363171 | 9/2011 |
| EP | 2814304 | 12/2014 |
| FR | 2 560 421 | 8/1985 |
| FR | 2911843 | 8/2008 |
| GB | 0 957 342 | 5/1964 |
| GB | 2 015 821 | 9/1979 |
| GB | 2 361 523 | 10/2001 |
| JP | 43-23267 | 10/1968 |
| JP | U48-108098 | 12/1973 |
| JP | 57-162527 | 10/1982 |
| JP | 58-141000 | 8/1983 |
| JP | 61-80800 | 4/1986 |
| JP | 61-225798 | 10/1986 |
| JP | 62-150804 | 7/1987 |
| JP | 62-186500 | 8/1987 |
| JP | 10-071213 | 3/1988 |
| JP | 63-149344 | 6/1988 |
| JP | 63-218200 | 9/1988 |
| JP | 63-226899 | 9/1988 |
| JP | 64-89621 | 4/1989 |
| JP | 01-276797 | 11/1989 |
| JP | 01-302700 | 12/1989 |
| JP | 04-269700 | 9/1990 |
| JP | 03-20700 | 1/1991 |
| JP | 4-94198 | 3/1992 |
| JP | 04-128717 | 4/1992 |
| JP | 04-129768 | 4/1992 |
| JP | 04-242196 | 8/1992 |
| JP | 04-269700 | 9/1992 |
| JP | 04-273409 | 9/1992 |
| JP | 04-337300 | 11/1992 |
| JP | 05-341352 | 12/1993 |
| JP | 06-233831 | 8/1994 |
| JP | 06-036893 | 10/1994 |
| JP | 07-260939 | 10/1995 |
| JP | 07-263196 | 10/1995 |
| JP | 07-263200 | 10/1995 |
| JP | 08-173890 | 7/1996 |
| JP | 08-264298 | 10/1996 |
| JP | 09-162585 | 6/1997 |
| JP | 11-47287 | 2/1999 |
| JP | 11-102800 | 4/1999 |
| JP | 11-243295 | 9/1999 |
| JP | 03-020700 B2 | 3/2000 |
| JP | 2000-294399 | 10/2000 |
| JP | 2001-6900 | 1/2001 |
| JP | 2001-009050 | 1/2001 |
| JP | 2001-129103 | 5/2001 |
| JP | 2001-346893 | 12/2001 |
| JP | 2002-164686 | 6/2002 |
| JP | 2002-533888 | 10/2002 |
| JP | 2002-533888 A | 10/2002 |
| JP | 2003-517755 | 5/2003 |
| JP | 2005-526578 | 9/2005 |
| JP | 2007-260193 | 10/2007 |
| JP | 2007-260193 A | 10/2007 |
| JP | 2007-263200 A | 10/2007 |
| JP | 05-046928 | 3/2008 |
| JP | 2008-507826 | 3/2008 |
| JP | 04-242196 B2 | 3/2009 |
| JP | 2009-515671 | 4/2009 |
| JP | 2009-516905 | 4/2009 |
| JP | 04-269700 B2 | 5/2009 |
| JP | 2009-524201 | 6/2009 |
| JP | 2009-524201 A | 6/2009 |
| JP | 2011-501391 | 1/2011 |
| JP | 2011-501391 A | 1/2011 |
| JP | 2011-505191 | 2/2011 |
| JP | 2011-505670 | 2/2011 |
| JP | 2011-507151 | 3/2011 |
| JP | 2011-507151 A | 3/2011 |
| JP | 2012-195279 | 10/2012 |
| SU | 300137 | 11/1969 |
| SU | 569 635 | 8/1977 |
| TW | 200930160 | 7/2009 |
| TW | 200934682 | 8/2009 |
| TW | 200939908 | 9/2009 |
| TW | 200940120 | 10/2009 |
| WO | WO 86/07229 | 12/1986 |
| WO | WO 90/12413 | 10/1990 |
| WO | WO 92/03028 | 2/1992 |
| WO | WO 93/02536 | 2/1993 |
| WO | WO 98/17342 | 4/1998 |
| WO | WO 99/39385 | 8/1999 |
| WO | WO 00/40064 | 7/2000 |
| WO | WO 00/49624 | 8/2000 |
| WO | WO 01/26230 | 4/2001 |
| WO | WO 01/26569 | 4/2001 |
| WO | WO 02/07817 | 1/2002 |
| WO | WO 03/039212 | 5/2003 |
| WO | WO 03/092812 | 11/2003 |
| WO | WO 2004/026401 | 4/2004 |
| WO | WO 2004/101070 | 11/2004 |
| WO | WO 2006-012467 | 2/2006 |
| WO | WO 2007/061937 | 5/2007 |
| WO | WO-2007/061937 A2 | 5/2007 |
| WO | WO 2007061937 A2 * | 5/2007 | ............... A61N 5/10 |
| WO | WO 2007/084701 | 7/2007 |
| WO | WO 2007/130164 | 11/2007 |
| WO | WO 2007/145906 | 12/2007 |
| WO | WO 2008/030911 | 3/2008 |
| WO | WO 2008/081480 | 10/2008 |
| WO | WO 2009/048745 | 4/2009 |
| WO | WO 2009/070173 | 6/2009 |
| WO | WO 2009/070588 | 6/2009 |
| WO | WO 2009/073480 | 6/2009 |
| WO | WO 2009073480 A2 * | 6/2009 | ............... H03L 7/00 |
| WO | WO 2013/079311 | 6/2013 |
| WO | WO2014/018706 | 1/2014 |
| WO | WO2014/018876 | 1/2014 |

OTHER PUBLICATIONS

"510(k) Summary: Ion Beam Applications S.A.", FDA, Jul. 12, 2001, 5 pages.

"510(k) Summary: Optivus Proton Beam Therapy System", Jul. 21, 2000, 5 pages.

"An Accelerated Collaboration Meets with Beaming Success," Lawrence Livermore National Laboratory, Apr. 12, 2006, S&TR, Livermore, California, pp. 1-3, http://www.llnl.gov/str/April06/Caporaso.html.

"CPAC Highlights Its Proton Therapy Program at ESTRO Annual Meeting", TomoTherapy Incorporated, Sep. 18, 2008, Madison, Wisconsin, pp. 1-2.

"Indiana's mega-million proton therapy cancer center welcomes its first patients" [online] Press release, Health & Medicine Week, 2004, retrieved from NewsRx.com, Mar. 1, 2004, pp. 119-120.

"LLNL, UC Davis Team Up to Fight Cancer," Lawrence Livermore National Laboratory, Apr. 28, 2006, SF-06-04-02, Livermore, California, pp. 1-4.

"Patent Assignee Search 'Paul Scherrer Institute,'" Library Services at Fish & Richardson P.C., Mar. 20, 2007, 40 pages.

(56) References Cited

OTHER PUBLICATIONS

"Patent Prior Art Search for 'Proton Therapy System'," Library Services at Fish & Richardson P.C., Mar. 20, 2007, 46 pages.
"Superconducting Cyclotron Contract" awarded by Paul Scherrer Institute (PSI), Villigen, Switzerland, http://www.accel.de/News/superconducting_cyclotron_contract.htm, Jan. 2009, 1 page.
"The Davis 76-Inch Isochronous Cyclotron", Beam On: Crocker Nuclear Laboratory, University of California, 2009, 1 page.
"The K100 Neutron-therapy Cyclotron," National Superconducting Cyclotron Laboratory at Michigan State University (NSCL), retrieved from: http://www.nscl.msu.edu/tech/accelerators/k100, Feb. 2005, 1 page.
"The K250 Proton therapy Cyclotron," National Superconducting Cyclotron Laboratory at Michigan State University (NSCL), retrieved from: http://www.nscl.msu.edu/tech/accelerators/k250.html, Feb. 2005, 2 pages.
"The K250 Proton-therapy Cyclotron Photo Illustration," National Superconducting Cyclotron Laboratory at Michigan State University (NSCL), retrieved from: http://www.nscl.msu.edu/media/image/experimental-equipment-technology/250.html, Feb. 2005, 1 page.
18$^{th}$ Japan Conference on Radiation and Radioisotopes [Japanese], Nov. 25-27, 1987, 9 pages.
Abrosimov et al., "1000MeV Proton Beam Therapy facility at Petersburg Nuclear Physics Institute Synchrocyclotron," Medical Radiology (Moscow) 32, 10 (1987) revised in Journal of Physics, Conference Series 41, 2006, pp. 424-432, Institute of Physics Publishing Limited.
Abrosimov et al., *Proc. Academy Science*, 1985, USSR 5, p. 84.
Adachi et al., "A 150MeV FFAG Synchrotron with "Return-Yoke Free" Magent," *Proceedings of the 2001 Particle Accelerator Conference*, Chicago, 2001, 3 pages.
Ageyev et al., "The IHEP Accelerating and Storage Complex (UNK) Status Report," *11th International Conference on High-Energy Accelerators*, 1980, pp. 60-70.
Agosteo et al., "Maze Design of a gantry room for proton therapy," *Nuclear Instruments & Methods in Physics Research*, 1996, Section A, 382, pp. 573-582.
Alexeev et al., "R4 Design of Superconducting Magents for Proton Synchrotrons," *Proceedings of the Fifth International Cryogenic Engineering Conference*, 1974, pp. 531-533.
Allardyce et al., "Performance and Prospects of the Reconstructed CERN 600 MeV Synchrocyclotron," *IEEE Transactions on Nuclear Science USA*, Jun. 1977, ns-24:(3)1631-1633.
Alonso, "Magnetically Scanned Ion Beams for Radiation Therapy," Accelerator & Fusion Research Division, Lawrence Berkeley Laboratory, Berkeley, CA, Oct. 1988, 13 pages.
Amaldi et al., "The Italian project for a hadrontherapy centre" *Nuclear Instruments and Methods in Physics Research A*, 1995, 360, pp. 297-301.
Amaldi, "Overview of the world landscape of Hadrontherapy and the projects of the TERA foundation," Physica Medica, An International journal Devoted to the Applications of Physics to Medicine and Biology, Jul. 1998, vol. XIV, Supplement 1, 6th Workshop on Heavy Charged Particles in Biology and Medicine, Instituto Scientific Europeo (ISE), Sep. 29-Oct. 1, 1977, Baveno, pp. 76-85.
Anferov et al., "Status of the Midwest Proton Radiotherapy Institute," Proceedings of the 2003 Particle Accelerator Conference,2003, pp. 699-701.
Anferov et al., "The Indiana University Midwest Proton Radiation Institute," Proceedings of the 2001 Particle Accelerator Conference, 2001, Chicago, pp. 645-647.
Appun, "Various problems of magnet fabrication for high-energy accelerators," *Journal for All Engineers Interested in the Nuclear Field*, 1967, pp. 10-16 (1967) [Lang.: German], *English bibliographic information* (http://www.osti.gov/energycitations/product.biblio.jsp?osti_id=4442292).
Arduini et al. "Physical specifications of clinical proton beams from a synchrotron," *Med. Phys*, Jun. 1996, 23 (6): 939-951.

Badano et al., "Proton-Ion Medical Machine Study (PIMMS) Part I," PIMMS, Jan. 1999, 238 pages.
Beeckman et al., "Preliminary design of a reduced cost proton therapy facility using a compact, high field isochronous cyclotron," *Nuclear Instruments and Methods in Physics Reasearch B56/57*, 1991, pp. 1201-1204.
Bellomo et al., "The Superconducting Cyclotron Program at Michigan State University," *Bulletin of the American Physical Society*, Sep. 1980, 25(7):767.
Benedikt and Carli, "Matching to Gantries for Medical Synchrotrons" *IEEE Proceedings of the 1997 Particle Accelerator Conference*, 1997, pp. 1379-1381.
Bieth et al., "A Very Compact Protontherapy Facility Based on an Extensive Use of High Temperature Superconductors (HTS)" *Cyclotrons and their Applications 1998*, Proceedings of the Fifteenth International Conference on Cyclotrons and their Applications, Caen, Jun. 14-19, 1998, pp. 669-672.
Bigham, "Magnetic Trim Rods for Superconducting Cyclotrons," Nuclear Instruments and Methods (North-Holland Publishing Co.), 1975, 141:223-228.
Bimbot, "First Studies of the External Beam from the Orsay S.C. 200 MeV," Institut de Physique Nucleaire, BP 1, Orsay, France, *IEEE*, 1979, pp. 1923-1926.
Blackmore et al., "Operation of the Triumf Proton Therapy Facility," *IEEE Proceedings of the 1997 Particle Accelerator Conferenc*, May 12-16, 19973:3831-3833.
Bloch, "The Midwest Proton Therapy Center," Application of Accelerators in Research and Industry, Proceedings of the Fourteenth Int'l. Conf., Part Two, Nov. 1996, pp. 1253-1255.
Blosser et al., "Problems and Accomplishments of Superconducting Cyclotrons," Proceedings of the 14$^{th}$ International Conference, Cyclotrons and Their Applications, Oct. 1995, pp. 674-684.
Blosser et al., "Superconducting Cyclotrons", Seventh International Conference on Cyclotrons and their Applications, Aug. 19-22, 1975, pp. 584-594.
Blosser et al., "Progress toward an experiment to study the effect of RF grounding in an internal ion source on axial oscillations of the beam in a cyclotron," National Superconducting Cyclotron Laboratory, Michigan State University, Report MSUCL-760, CP600, Cyclotrons and their Applications 2011, Sixteenth International Conference, 2001, pp. 274-276.
Blosser et al., "A Compact Superconducting Cyclotron for the Production of High Intensity Protons," Proceedings of the 1997 Particle Accelerator Conference, May 12-16, 1997, 1:1054-1056.
Blosser et al., "Advances in Superconducting Cyclotrons at Michigan State University," Proceedings of the 11$^{th}$ International Conference on Cyclotrons and their Applications, Oct. 1986, pp. 157-167 , Tokyo.
Blosser et al., "Characteristics of a 400 (Q2/A) MeV Super-Conducting Heavy-Ion Cyclotron," Bulletin of the American Physical Society, Oct. 1974, p. 1026.
Blosser et al., "Medical Accelerator Projects at Michigan State Univ." IEEE Proceedings of the 1989 Particle Accelerator Conference, Mar. 20-23, 1989, 2:742-746.
Blosser et al., "Superconducting Cyclotron for Medical Application", *IEEE Transactions on Magnetics*, Mar. 1989, 25(2): 1746-1754.
Blosser, "Application of Superconductivity in Cyclotron Construction," *Ninth International Conference on Cyclotrons and their Applications*, Sep. 1981, pp. 147-157.
Blosser, "Applications of Superconducting Cyclotrons," Twelfth International Conference on Cyclotrons and Their Applications, May 8-12, 1989, pp. 137-144.
Blosser, "Future Cyclotrons," AIP, *The Sixth International Cyclotron Conference*, 1972, pp. 16-32.
Blosser, "Medical Cyclotrons," *Physics Today*, Special Issue Physical Review Centenary, Oct. 1993, pp. 70-73.
Blosser, "Preliminary Design Study Exploring Building Features Required for a Proton Therapy Facility for the Ontario Cancer Institute", Mar. 1991, MSUCL-760a, 53 pages.
Blosser, "Program on the Coupled Superconducting Cyclotron Project," *Bulletin of the American Physical Society*, Apr. 1981, 26(4):558.

(56) References Cited

OTHER PUBLICATIONS

Blosser, "Synchrocyclotron Improvement Programs," *IEEE Transactions on Nuclear Science USA*, Jun. 1969, 16(3):Part I, pp. 405-414.
Blosser, "The Michigan State University Superconducting Cyclotron Program," *Nuclear Science*, Apr. 1979, NS-26(2):2040-2047.
Blosser, National Superconducting Cyclotron Laboratory, Michigan State University, Report MSUCL-760, 2001, 3 pages.
Blosser, H., Present and Future Superconducting Cyclotrons, *Bulletin of the American Physical Society*, Feb. 1987, 32(2):171 Particle Accelerator Conference, Washington, D.C.
Blosser, H.G., "Superconducting Cyclotrons at Michigan State University", Nuclear Instruments & Methods in Physics Research, 1987,vol. B 24/25, part II, pp. 752-756.
Botha et al., "A New Multidisciplinary Separated-Sector Cyclotron Facility," *IEEE Transactions on Nuclear Science*, 1977, NS-24(3):1118-1120.
Canadian Office action issued in Canadian application No. 2,629,333 issued Aug. 30, 2010, 5 pages.
Chichili et al., "Fabrication of Nb3Sn Shell-Type Coils with Pre-Preg Ceramic Insulation," American Institute of Physics Conference Proceedings, AIP USA, No. 711, (XP-002436709, ISSN: 0094-243X), 2004, pp. 450-457.
Chinese Office action from corresponding Chinese application No. 200880125832.9, mailed Jun. 5, 2012, 6 pages.
Chinese Office Action issued in Chinese Application No. 200780102281.X , dated Dec. 7, 2011, 23 pages (with English translation).
Chinese Office action issued in Chinese application No. 200880125832.9, dated Sep. 22, 2011, 111 pages.
Chinese Office action issued in Chinese application No. 200880125918.1, dated Sep. 15, 2011, 111 pages.
Chong et al., Radiology Clinic North American 7, 3319, 1969, 27 pages.
Chu et al., "Performance Specifications for Proton Medical Facility," Lawrence Berkeley Laboratory, University of California, Mar. 1993, 128 pages.
Chu et al., "Instrumentation for Treatment of Cancer Using Proton and Light-ion Beams," Review of Scientific Instruments, Aug. 1993, 64 (8):2055-2122.
Chu, "Instrumentation in Medical Systems," Accelerator and Fusion Research Division, Lawrence Berkeley Laboratory, University of California, Berkeley, CA, May 1995, 9 pages.
Cole et al., "Design and Application of a Proton Therapy Accelerator," Fermi National Accelerator Laboratory, *IEEE*, 1985, 5 pages.
Collins, et al., "The Indiana University Proton Therapy System," Proceedings of EPAC 2006, Edinburgh, Scotland, 2006, 3 pages.
Conradi et al., "Proposed New Facilities for Proton Therapy at iThemba Labs," *Proceedings of EPAC*, 2002, pp. 560-562.
C/E Source of Ions for Use in Sychro-Cyclotrons Search, Jan. 31, 2005, 9 pages.
Source Search "Cites of U.S. and Foreign Patents/Published applications in the name of Mitsubishi Denki Kabushiki Kaisha and Containing the Keywords (Proton and Synchrocyclotron)," Jan. 2005, 8 pages.
Cosgrove et al., "Microdosimetric Studies on the Orsay Proton Synchrocyclotron at 73 and 200 MeV," *Radiation Protection Dosimetry*, 1997, 70(1-4):493-496.
Coupland, "High-field (5 T) pulsed superconducting dipole magnet," *Proceedings of the Institution of Electrical Engineers*, Jul. 1974, 121(7):771-778.
Coutrakon et al. "Proton Synchrotrons for Cancer Therapy," Application of Accelerators in Research and Industry—Sixteenth International Conf., American Institute of Physics, Nov. 1-5, 2000, vol. 576, pp. 861-864.
Coutrakon et al., "A prototype beam delivery system for the proton medical accelerator at Loma Linda," *Medical Physics*, Nov./Dec. 1991, 18(6):1093-1099.

Cuttone, "Applications of a Particle Accelerators in Medical Physics," Istituto Nazionale di Fisica Nucleare-Laboratori Nazionali del Sud, V.S. Sofia, 44 Cantania, Italy, Jan. 2010, 17 pages.
Dahl P, "Superconducting Magnet System," American Institute of Physics, AIP Conference Proceedings, 1987-1988, 2: 1329-1376.
Dialog Search, Jan. 31, 2005, 17 pages.
Dugan et al., "Tevatron Status" IEEE, Particle Accelerator Conference, Accelerator Science & Technology, 1989, pp. 426-430.
Eickhoff et al., "The Proposed Accelerator Facility for Light Ion Cancer Therapy in Heidelberg," Proceedings of the 1999 Particle Accelerator Conference, New York, 1999, pp. 2513-2515.
Enchevich et al., "Minimizing Phase Losses in the 680 MeV Synchrocyclotron by Correcting the Accelerating Voltage Amplitude," *Atomnaya Energiya*, 1969, 26:(3):315-316.
Endo et al., "Compact Proton and Carbon Ion Synchrotrons for Radiation Therapy," Proceedings of EPAC 2002, Paris France, 2002, pp. 2733-2735.
European Communication issued in corresponding European application No. 11165422.4, dated Sep. 2, 2011, 5 pages.
European Communication issued in European application No. 07868958.5, dated Nov. 26, 2010, 50 pages.
European Patent Office communication issued in European application No. 08856764.9, dated Jul. 30, 2010, 2 pages.
European Patent Office communicationissued in European application No. 07868958.5, dated Jul. 16, 2010, 2 pages.
European Search Report issued in European Application No. 11165423.2, dated Aug. 8, 2011, 118 pages.
Flanz et al., "Treating Patients with the NPTC Accelerator Based Proton Treatment Facility," Proceedings of the 2003 Particle Accelerator Conference, 2003, pp. 690-693.
Flanz et al., "Large Medical Gantries," Particle Accelerator Conference, Massachusetts General Hospital, 1995, pp. 1-5.
Flanz et al., "Operation of a Cyclotron Based Proton Therapy Facility", Massachusetts General Hospital, Boston, MA 02114, pp. 1-4, retrieved from Internet in 2009.
Flanz et al., "The Northeast Proton Therapy Center at Massachusetts General Hospital," Fifth Workshop on Heavy Charge Particles in Biology and Medicine, GSI, Darmstadt, Aug. 1995, 11 pages.
Flanz, et al., "Scanning Beam Technologies", PTCOG 2008, 28 pages.
Flood and Frazier, . "The Wide-Band Driven RF System for the Berkeley 88-Inch Cyclotron," American Institute of Physics, Conference Proceedings., No. 9, 1972, 459-466.
Foster and Kashikhin, "Superconducting Superferric Dipole Magent with Cold Iron Core for the VLHC," *IEEE Transactions on Applied Superconductivity*, Mar. 2002, 12(1):111-115.
Friesel et al., "Design and Construction Progress on the IUCF Midwest Proton Radiation Institute," Proceedings of EPAC 2002, 2002, pp. 2736-2738.
Fukumoto et al., "A Proton Therapy Facility Plan" Cyclotrons and their Applications, Proceedings of the 13th International Conference, Vancouver, Canada, Jul. 6-10, 1992, pp. 258-261.
Fukumoto, "Cyclotron Versus Synchrotron for Proton Beam Therapy," KEK Prepr., No. 95-122, 995, pp. 533-536.
Goto et al., "Progress on the Sector Magnets for the Riken SRC," American Institute of Physics, CP600, Cyclotrons and Their Applications 2001, Sixteenth International Conference, 2001, pp. 319-323.
Graffman et al., "Design Studies for a 200 MeV Proton Clinic for Radiotherapy," AIP Conference Proceedings: Cyclotrons—1972, 1972, No. 9, pp. 603-615.
Graffman et al., *Acta Radiol. Therapy Phys. Biol.* 1970, 9, 1 (1970).
Graffman, et. al. "Proton radiotherapy with the Uppsala cyclotron. Experience and plans" *Strahlentherapie*, 1985, 161(12):764-770.
Hede, "Research Groups Promoting Proton Therapy "Lite,"" Journal of the National Cancer Institute, Dec. 6, 2006, 98(23):1682-1684.
Heinz, "Superconducting Pulsed Magnetic Systems for High-Energy Synchrotrons," *Proceedings of the Fourth International Cryogenic Engineering Conference*, May 24-26, 1972, pp. 55-63.
Hentschel et al., "Plans for the German National Neutron Therapy Centre with a Hospital-Based 70 MeV Proton Cyclotron at University Hospital Essen/Germany," Cyclotrons and their Applications,

(56) References Cited

OTHER PUBLICATIONS

Proceedings of the Fifteenth International Conference on Cyclotrons and their Applications, Caen, Franco, Jun. 14-19, 1998, pp. 21-23.
Hepburn et al., "Superconducting Cyclotron Neutron Source for Therapy," *International Journal of Radiation Oncology Biology Physics*, vol. 3 complete, 1977, pp. 387-391.
Hirabayashi, "Development of Superconducting Magnets for Beam Lines and Accelerator at KEK," *IEEE Transaction on Magnetics*, Jan. 1981, Mag-17(1):728-731.
International Preliminary Report on Patentability issued in PCT Application No. PCT/US2008/084695, dated Jun. 10, 2010, 10 pages.
International Preliminary Report on Patentability issued in PCT Application No. PCT/US2008/084699, dated Jun. 10, 2010, 8 pages.
International Preliminary Report on Patentability issued in PCT Application No. PCT/US2007/086109, dated Jun. 10, 2010, 7 pages.
International Preliminary Report on Patentability in Internation Application No. PCT/US2006/44853, dated May 29, 2008, 8 pages.
International Preliminary Report on Patentability in Internation Application No. PCT/US2007/001506, dated Jul. 5, 2007, 15 pages.
International Preliminary Report on Patentability in Internation Application No. PCT/US2007/001628, dated Apr. 22, 2008, 15 pages.
International Search Report and Written Opinion in International Application No. PCT/US2006/44853, dated Oct. 5, 2007, 3 pages.
International Search Report and Written Opinion in International Application No. PCT/US2007/001506, dated Jul. 5, 2007, Publication No. WO2007/084701, Published Jul. 26, 2007, 14 pages.
International Preliminary Report on Patentability on International Application No. PCT/US2008/077513, dated Apr. 22, 2010.
International Search Report and Written Opinion in International Application No. PCT/US2008/077513, dated Oct. 1, 2009, 73 pages.
International Search Report and Written Opinion in International Application No. PCT/US2008/084695, dated Jan. 26, 2009, 15 pages.
International Search Report in International Application No. PCT/US2007/001628, dated Feb. 18, 2008, 4 pages.
International Search Report and Written Opinion in International Application No. PCT/US2007/086109, dated Aug. 26, 2008, 6 pages.
International Search Report and Written Opinion in International Application No. PCT/US2008/084699, dated Feb. 4, 2009, 11 pages.
Ishibashi and McInturff, "Winding Design Study of Superconducting 10 T Dipoles for a Synchrotron," *IEEE Transactions on Magnetics*, May 1983, MAG-19(3):1364-1367.
Ishibashi and McInturff, "Stress Analysis of Superconducting 10T Magnets for Synchrotron," Proceedings of the Ninth International Cryogenic Engineering Conference, May 11-14, 1982, pp. 513-516.
Jahnke et al., "First Superconducting Prototype Magnets for a Compact Synchrotron Radiation Source in Operation," *IEEE Transactions on Magnetics*, Mar. 1988, 24(2):1230-1232.
Jones and Dershem, "Synchrotron Radiation from Proton in a 20 TEV, 10 TESLA Superconducting Super Collide,r" *Proceedings of the 12th International Conference on High-Energy Accelerator*, Aug. 11-16, 1983, pp. 138-140.
Jones and Mills, "The South African National Accelerator Centre: Particle Therapy and Isotope Production Programmes," *Radiation Physics and Chemistry*, Apr.-Jun. 1998, 51(4-6):571-578.
Jones et al., "Status Report of the NAC Particle Therapy Programme," *Stralentherapie and Onkologie*, vol. 175, Suppl. II, Jun. 1999, pp. 30-32.
Jones, "Progress with the 200 MeV Cyclotron Facility at the National Accelerator Centre," Commission of the European Communities Radiation Protection Proceedings, Fifth Symposium on Neutron Dosimetry, Sep. 17-21, 1984, vol. II, pp. 989-998.
Jones, "Present Status and Future Trends of Heavy Particle Radiotherapy," Cyclotrons and their Applications 1998, Proceedings of the Fifteenth International Conference on Cyclotrons and their Applications, Jun. 14-19, 1998, pp. 13-20.
Jongen et al., "Development of a Low-cost Compact Cyclotron System for Proton Therapy," *National Institute of Radiol. Sci*,1991, No. 81, pp. 189-200.
Jongen et al., "Progress report on the IBA-SHI small cyclotron for cancer therapy" *Nuclear Instruments and Methods in Physics Research*, Section B, vol. 79, issue 1-4, 1993, pp. 885-889.
Jongent et al., "The proton therapy system for the NPTC: Equipment Description and progress report," *Nuclear Instruments and methods in physics research*, 1996, Section B, 113(1): 522-525.
Jongen et al., "The proton therapy system for MGH's NPTC: equipment description and progress report," *Bulletin du Cancer/Radiotherapie, Proceedings of the meeting of the European Heavy Particle Therapy Group*, 1996, 83(Suppl. 1):219-222.
Kanai et al., "Three-dimensional Beam Scanning for Proton Therapy," Nuclear Instruments and Methods in Physic Research, Sep. 1, 1983, The Netherlands, 214(23):491-496.
Karlin et al., "Medical Radiology" (Moscow), 1983, 28, 13.
Karlin et al., "The State and Prospects in the Development of the Medical Proton Tract on the Synchrocyclotron in Gatchina," *Med. Radiol.*, Moscow, 28(3):28-32 (Mar. 1983)(German with English Abstract on end of p. 32).
Kats and Druzhinin, "Comparison of Methods for Irradiation Prone Patients," *Atomic Energy*, Feb. 2003, 94(2):120-123.
Kats and Onosovskii, "A Simple, Compact, Flat System for the Irradiation of a Lying Patient with a Proton Beam from Different Directions," *Instruments and Experimental Techniques*, 1996, 39(1): 132-134.
Kats and Onosovskii, "A Planar Magnetooptical System for the Irradiation of a Lying Patient with a Proton Beam from Various Directions," *Instruments and Experimental Techniques*, 1996, 39(1):127-131.
Khoroshkov et al.,"Moscow Hospital-Based Proton Therapy Facility Design," *Am. Journal Clinical Oncology: CCT*, Apr. 1994, 17(2):109-114.
Kim and Blosser, "Optimized Magnet for a 250 MeV Proton Radiotherapy Cyclotron," Cyclotrons and Their Applications 2001, May 2001, *Sixteenth International Conference*, pp. 345-347.
Kim and Yun, "A Light-Ion Superconducting Cyclotron System for Multi-Disciplinary Users," *Journal of the Korean Physical Society*, Sep. 2003, 43(3):325-331.
Kim et al., "Construction of 8T Magnet Test Stand for Cyclotron Studies," *IEEE Transactions on Applied Superconductivity*, Mar. 1993, 3(1):266-268.
Kim et al., "Design Study of a Superconducting Cyclotron for Heavy Ion Therapy," *Cyclotrons and Their Applications 2001, Sixteenth International Conference*, May 13-17, 2001, pp. 324-326.
Kim et al., "Trim Coil System for the Riken Cyclotron Ring Cyclotron," *Proceedings of the 1997 Particle Accelerator Conference, IEEE*, Dec. 1981, vol. 3, pp. 214-235 or 3422-3424, 1998.
Kim, "An Eight Tesla Superconducting Magnet for Cyclotron Studies," Ph.D. Dissertation, Michigan State University, Department of Physics and Astronomy, 1994, 138 pages.
Kimstrand, "Beam Modelling for Treatment Planning of Scanned Proton Beams," Digital Comprehensive Summaries of Uppsala dissertations from the Faculty of Medicine 330, Uppsala Universitet, 2008, 58 pages.
Kishida and Yano, "Beam Transport System for the RIKEN SSC (II)," *Scientific Papers of the Institute of Physical and Chemical Research*, Dec. 1981, 75(4):214-235.
Koehler et al., "Range Modulators for Protons and Heavy Ions," *Nuclear Instruments and Methods*, 1975, vol. 131, pp. 437-440.
Koto and Tsujii, "Future of Particle Therapy," *Japanese Journal of Cancer Clinics*, 2001, 47(1):95-98 [Lang.: Japanese], English abstract (http://sciencelinks.jp/j-east/article/200206/000020020601A0511453.php).
Kraft et al., "Hadrontherapy in Oncology," U. Amaldi and Larrsson, editors Elsevier Science, 1994, 390 pages.

(56) References Cited

OTHER PUBLICATIONS

Krevet et al., "Design of a Strongly Curved Superconducting Bending Magnet for a Compact Synchrotron Light Source," *Advance in Cryogenic Engineering*, 1988, vol. 33, pp. 25-32.

Laisne et al., "The Orsay 200 MeV Synchrocyclotron," *IEEE Transactions on Nuclear Science*, Apr. 1979, NS-26(2):1919-1922.

Larsson et al., *Nature*, 1958, 182:1222.

Larsson, "Biomedical Program for the Converted 200-MeV Synchrocyclotron at the Gustaf Werner Institute," *Radiation Research*, 1985, 104:S310-S318.

Lawrence et al., "Heavy particles in acromegaly and Cushing's Disease," in Endocrine and Norendocrine Hormone Producing Tumors (Year Book Medical Chicago, 1973, pp. 29-61.

Lawrence et al., "Successful Treatment of Acromegaly: Metabolic and Clinical Studies in 145 Patients," *The Journal of Clinical Endrocrinology and Metabolism*, Aug. 1970, 31(2), 21 pages.

Lawrence et al., "Treatment of Pituitary Tumors," (Excerpta medica, Amsterdam/American Elsevier, New York, 1973, pp. 253-262.

Lawrence, *Cancer*, 1957, 10:795.

Lecroy et al., "Viewing Probe for High Voltage Pulses," *Review of Scientific Instruments USA*, Dec. 1960, 31(12):1354.

Lin et al., "Principles and 10 Year Experience of the Beam Monitor System at the PSI Scanned Proton Therapy Facility", Center for Proton Radiation Therapy, Paul Scherrer Institute, CH-5232, Villigen PSI, Switzerland, 2007, 21 pages.

Linfoot et al., "Acromegaly," in Hormonal Proteins and Peptides, edited by C.H. Li, 1975, pp. 191-246.

Literature Author and Keyword Search, Feb. 14, 2005, 44 pages.

Literature Keyword Search, Jan. 24, 2005, 96 pages.

Literature Search and Keyword Search for Synchrocyclotron, Jan. 25, 2005, 68 pages.

Literature Search by Company Name/Component Source, Jan. 24, 2005, 111 pages.

Literature Search, Jan. 26, 2005, 36 pages.

Livingston et al., "A capillary ion source for the cyclotron," *Review Science Instruments*, Feb. 1939, 10:63.

Mandrillon, "High Energy Medical Accelerators," *EPAC 90, 2nd European Particle Accelerator Conference*, Jun. 12-16, 1990, 2:54-58.

Marchand et al., "IEA Proton Pencil Beam Scanning: an Innovative Solution for Cancer Treatment," Proceedings of EPAC 2000, Vienna, Austria, 3 pages.

Marti et al., "High Intensity Operation of a Superconducting Cyclotron," *Proceedings of the 14the International Conference, Cyclotrons and Their Applications*, Oct. 1995, pp. 45-48 (Oct. 1995).

Martin, "Operational Experience with Superconducting Synchrotron Magnets" *Proceedings of the 1987 IEEE Particle Accelerator Conference*, Mar. 16-19, 1987, vol. 3 of 3:1379-1382.

Meote et al., "ETOILE Hadrontherapy Project, Review of Design Studies" *Proceedings of EPAC 2002*, 2002, pp. 2745-2747.

Miyamoto et al., "Development of the Proton Therapy System," *The Hitachi Hyoron*, 79(10):775-779 (1997) [Lang: Japanese], English abstract (http://www.hitachi.com/rev/1998/revfeb98/rev4706.htm).

Montelius et al., "The Narrow Proton Beam Therapy Unit at the Svedberg Laboratory in Uppsala," *ACTA Oncologica*, 1991, 30:739-745.

Moser et al., "Nonlinear Beam Optics with Real Fields in Compact Storage Rings," Nuclear Instruments & Methods in Physics Research/Section B, B30, Feb. 1988, No. 1, pp. 105-109.

Moyers et al., "A Continuously Variable Thickness Scatterer for Proton Beams Using Self-compensating Dual Linear Wedges" Lorna Linda University Medical Center, Dept. of Radiation Medicine, Lorna Linda, CA, Nov. 2, 1992, 21 pages.

*National Cancer Institute Funding* (Senate—Sep. 21, 1992) (www.thomas.loc.gov/cgi-bin/query/z?r102:S21SE2-712 (2 pages).

Nicholson, "Applications of Proton Beam Therapy," *Journal of the American Society of Radiologic Technologists*, May/Jun. 1996, 67(5): 439-441.

Nolen et al., "The Integrated Cryogenic—Superconducting Beam Transport System Planned for MSU," *Proceedings of the 12th International Conference on High-Energy Accelerators*, Aug. 1983, pp. 549-551.

Norimine et al., "A Design of a Rotating Gantry with Easy Steering for Proton Therapy," *Proceedings of EPAC 2002*, 2002, pp. 2751-2753.

Ogino, Takashi, "Heavy Charged Particle Radiotherapy-Proton Beam", Division of Radiation Oncology, National Cancer Hospital East, Kashiwa, Japan, Dec. 2003, 7 pages.

Okumura et al., "Overview and Future Prospect of Proton Radiotherapy," *Japanese Journal of Cancer Clinics*, 1997, 43(2):209-214 [Lang.: Japanese].

Okumura et al., "Proton Radiotherapy" *Japanese Journal of Cancer and Chemotherapy*, 1993, 10.20(14):2149-2155[Lang.: Japanese].

Outstanding from Search Reports, "Accelerator of Polarized Portons at Fermilab," 2005, 20 pages.

Paganetti et al., "Proton Beam Radiotherapy—The State of the Art," Springer Verlag, Heidelberg, ISBN 3-540-00321-5, Oct. 2005,36 pages.

Palmer and Tollestrup, "Superconducting Magnet Technology for Accelerators," *Annual Review of Nuclear and Particle Science*, 1984, vol. 34, pp. 247-284.

Patent Assignee and Keyword Searches for Synchrocyclotron, Jan. 25, 2005, 77 pages.

Pavlovic, "Beam-optics study of the gantry beam delivery system for light-ion cancer therapy," *Nuclear Instruments and Methods in Physics Research*, Section A, Nov. 1997, 399(2):439-454(16).

Pedroni and Enge, "Beam optics design of compact gantry for proton therapy" *Medical & Biological Engineering & Computing*, May 1995, 33(3):271-277.

Pedroni and Jermann, . "SGSMP: Bulletin Mar. 2002 Proscan Project, Progress Report on the PROSCAN Project of PSI" [online] retrieved from www.sgsmp.ch/protA23.htm, Mar. 2002, 5 pages.

Pedroni et al., "A Novel Gantry for Proton Therapy at the Paul Scherrer Institute," *Cycloctrons and Their Applications 2001: Sixteenth International Conference. AIP Conference Proceedings*, 2001, 600:13-17.

Pedroni et al., "The 200-MeV proton therapy project at the Paul Scherrer Institute: Conceptual design and practical realization," *Medical Physics*, Jan. 1995, 22(1):37-53.

Pedroni, "Accelerators for Charged Particle Therapy: Performance Criteria from the User Point of View," *Cyclotrons and their Applications, Proceedings of the 13th International Conference*, Jul. 6-10, 1992, pp. 226-233.

Pedroni, "Latest Developments in Proton Therapy" *Proceedings of EPAC 2000*, 2000, pp. 240-244.

Pedroni, "Status of Proton Therapy: results and future trends," Paul Scherrer Institute, Division of Radiation Medicine, 1994, 5 pages.

Peggs et al., "A Survey of Hadron Therapy Accelerator Technologies," Particle Accelerator Conference, Jun. 25-29, 2007, 7 pages.

Potts et al., "MPWP6-Therapy III: Treatment Aids and Techniques" *Medical Physics*, Sep./Oct. 1988, 15(5):798.

Pourrahimi et al., "Powder Metallurgy Processed Nb3Sn(Ta) Wire for High Field NMR magnets," *IEEE Transactions on Applied Superconductivity*, Jun. 1995, 5(2):1603-1606.

Prieels et al., "The IBA State-of-the-Art Proton Therapy System, Performances and Recent Results," *Application of Accelerators in Research and industry—Sixteenth Int'l. Conf, American Institute of Physics*, Nov. 1-5, 2000, 576:857-860.

Rabin et al., "Compact Designs for Comprehensive Proton Beam Clinical Facilities," *Nuclear Instruments & Methods in Physics Research*, Apr. 1989, Section B, vol. 40-41, Part II, pp. 1335-1339.

*Research & Development Magazine*, "Proton Therapy Center Nearing Completion," Aug. 1999, 41(9):2 pages, (www.rdmag.com).

Resmini, "Design Characteristics of the K=800 Superconducting Cyclotron at M.S.U.," Cyclotron Laboratory, Michigan State University, East Lansing, Michigan 48824, IEEE Transaction on Nuclear Science, vol. NS-26, No. 2, Apr. 1979, 8 pages.

RetroSearch "Berkeley 88-Inch Cyclotron 'RF' or 'Frequency Control'," Jan. 21, 2005, 36 pages.

RetroSearch "Berkeley 88-Inch Cyclotron," Jan. 24, 2005, 170 pages.

(56) References Cited

OTHER PUBLICATIONS

RetroSearch "Bernard Gottschalk, Cyclotron, Beams, Compensated Upstream Modulator, Compensated Scatter," Jan. 21, 2005, 20 pages.
RetroSearch "Cyclotron with 'RF' or 'Frequency Control'," Jan. 21, 2005, 49 pages.
RetroSearch Gottschalk, Bernard, Harvard Cyclotron Wheel, Jan. 21, 2005, 20 pages.
RetroSearch "Loma Linda University Beam Compensation," Jan. 21, 2005, 60 pages.
RetroSearch "Loma Linda University, Beam Compensation Foil Wedge," Jan. 21, 2005, 15 pages.
Revised Patent Keyword Search, Jan. 25, 2005, 88 pages.
Rifuggiato et, al., "Status Report of the LNS Superconducting Cyclotron" *Nukleonika*, 2003, 48: S131-S134, Supplement 2.
Rode, "Tevatron Cryogenic System," *Proceedings of the 12th International Conference on High-energy Accelerators, Fermilab*, Aug. 11-16, 1983, pp. 529-535.
Salzburger et al., "Superconducting Synchrotron Magnets Supraleitende Synchrotronmagnete," Siemens A.G., Erlangen (West Germany). Abteilung Technische Physik, Report No. BMFT-FB-T-75-25, Oct. 1975, p. 147, Journal Announcement: GRAI7619; STAR1415, Subm-Sponsored by Bundesmin. Fuer Forsch. U. Technol. In German; English Summary.
Schillo et al,. "Compact Superconducting 250 MeV Proton Cyclotron for the PSI Proscan Proton Therapy Project," *Cyclotrons and Their Applications 2001, Sixteenth International Conference*, 2001, pp. 37-39.
Schneider et al., "Nevis Synchrocyclotron Conversion Program—RF System," *IEEE Transactions on Nuclear Science USA*, Jun. 1969, ns 16(3): 430-433.
Schneider et al., "Superconducting Cyclotrons," IEEE Transactions on Magnetics, vol. MAG-11, No. 2, Mar. 1975, New York, pp. 443-446.
Schreuder et al., "The Non-orthogonal Fixed Beam Arrangement for the Second Proton Therapy Facility at the National Accelerator Centre," *Application of Accelerators in Research and Industry, American Institute of Physics, Proceedings of the Fifteenth International Conference*, Nov. 1998, Part Two, pp. 963-966.
Schreuder, "Recent Developments in Superconducting Cyclotrons," *Proceedings of the 1995 Particle Accelerator Conference*, May 1-5, 1995, vol. 1, pp. 317-321.
Schubert and Blosser, "Conceptual Design of a High Field Ultra-Compact Cyclotron for Nuclear Physics Research," *Proceedings of the 1997 Particle Accelerator Conference*, May 12-16, 1997, vol. 1, pp. 1060-1062.
Schubert, "Extending the Feasibility Boundary of the Isochronous Cyclotron," Dissertation submitted to Michigan State University, 1997, Abstract http://adsabs.harvard.edu/abs/1998PhDT.......147S.
Shelaev et al., "Design Features of a Model Superconducting Synchrotron of JINR," *Proceedings of the 12th International Conference on High-energy Accelerators*, Aug. 11-16, 1983, pp. 416-418.
Shintomi et. al, "Technology and Materials for the Superconducting Super Collider (SSC) Project," [Lang.: Japanese], The Iron and Steel Institute of Japan 00211575, 78(8): 1305-1313, 1992, http://ci.nii.ac.jp/naid/110001493249/en/.
Sisterson, "World Wide Proton Therapy Experience in 1997," *The American Insitute of Physics, Applications of Accelerators in Research and Industry, Proceedings of the Fifteenth International Conference*, Part Two, Nov. 1998, pp. 959-962.
Sisterson, "Clinical use of proton and ion beams from a world-wide perspective," *Nuclear Instruments and Methods in Physics Research*, Section B, 1989, 40-41:1350-1353.
Slater et al., "Developing a Clinical Proton Accelerator Facility: Consortium-Assisted Technology Transfer," *Conference Record of the 1991 IEEE Particle Accelerator Conference: Accelerator Science and Technology*, vol. 1, May 6-9, 1991, pp. 532-536.

Slater et al., "Development of a Hospital-Based Proton Beam Treatment Center," *International Journal of Radiation Oncology Biology Physics*, Apr. 1988, 14(4):761-775.
Smith et al., "The Northeast Proton Therapy Center at Massachusetts General Hospital" *Journal of Brachytherapy International*, Jan. 1997, pp. 137-139.
Snyder and Marti, "Central region design studies for a proposed 250 MeV proton cyclotron," *Nuclear Instruments and Methods in Physics Research*, Section A, 1995, vol. 355, pp. 618-623.
Soga, "Progress of Particle Therapy in Japan," Application of Accelerators in Research and Industry, American Institute of Physics, Sixteenth International Conference, Nov. 2000, pp. 869-872.
Spiller et al., "The GSI Synchrotron Facility Proposal for Acceleration of High Intensity Ion and Proton Beams" *Proceedings of the 2003 Particle Accelerator Conference*, May 12-16, 2003, vol. 1, pp. 589-591.
Stanford et al., "Method of Temperature Control in Microwave Ferroelectric Measurements," Sperry Microwave Electronics Company, Clearwater, Florida, Sep. 19, 1960, 1 page.
Tadashi et al., "Large superconducting super collider (SSC) in the planning and materials technology," 1992, 78(8):1305-1313, The Iron and Steel Institute of Japan 00211575.
Takada, "Conceptual Design of a Proton Rotating Gantry for Cancer Therapy," *Japanese Journal of Medical Physics*, 1995, 15(4):270-284.
Takayama et al., "Compact Cyclotron for Proton Therapy," *Proceedings of the $8^{th}$ Symposium on Accelerator Science and Technology*, Japan, Nov. 25-27, 1991, pp. 380-382.
Teng, "The Fermilab Tevatron," Coral Gables 1981, Proceedings, Gauge Theories, Massive Neutrinos, and Proton Decay, 1981, pp. 43-62.
The Journal of Practical Pharmacy, 1995, 46(1):97-103 [Japanese].
Tilly et al., "Development and verification of the pulsed scanned proton beam at The Svedberg Laboratory in Uppsala," *Phys. Med. Biol.*, 2007, 52:2741-2754.
Tobias et al., *Cancer Research*,1958, 18, 121 (1958).
Tom, "The Use of Compact Cyclotrons for Producing Fast Neutrons for Therapy in a Rotatable Isocentric Gantry," *IEEE Transaction on Nuclear Science*, Apr. 1979, 26(2):2294-2298.
Toyoda, "Proton Therapy System", Sumitomo Heavy Industries, Ltd., 2000, 5 pages.
Trinks et. al., "The Tritron: A Superconducting Separated-Orbit Cyclotron," *Nuclear Instruments and Methods in Physics Research*, Section A, 1986, vol. 244, pp. 273-282.
Tsuji, "The Future and Progress of Proton Beam Radiotherapy," *Journal of Japanese Society for Therapeutic Radiology and Oncology*, 1994, 6(2):63-76.
UC Davis School of Medicine, "Unlikely Partners Turn Military Defense into Cancer Offense", Current Issue Summer 2008, Sacramento, California, pp. 1-2.
Umegaki et al., "Development of an Advanced Proton Beam Therapy System for Cancer Treatment" *Hitachi Hyoron*, 2003, 85(9):605-608 [Lang.: Japanese], English abstract, http://www.hitachi.com/ICSFiles/afieldfile/2004/06/01/r2003_04_104.pdf or http://www.hitachi.com/rev/archive/2003/2005649_12606.html (full text) [Hitachi, 52(4), Dec. 2003].
Umezawa et al., "Beam Commissioning of the new Proton Therapy System for University of Tsukuba," *Proceedings of the 2001 Particle Accelerator Conference*, vol. 1, Jun. 18-22, 2001, pp. 648-650.
van Steenbergen, "Superconducting Synchroton Development at BNL," *Proceedings of the 8th International Conference on High-Energy Accelerators CERN 1971*, 1971, pp. 196-198.
van Steenbergen, "The CMS, a Cold Magnet Synchrotron to Upgrade the Proton Energy Range of the BNL Facility," *IEEE Transactions on Nuclear Science*, Jun. 1971, 18(3):694-698.
Vandeplassche et al., "235 MeV Cyclotron for MGH's Northeast Proton Therapy Center (NPTC): Present Status," EPAC 96, *Fifth European Partical Accelerator Conference*, vol. 3, Jun. 10-14, 1996, pp. 2650-2652.
Vorobiev et al., "Concepts of a Compact Achromatic Proton Gantry with a Wide Scanning Field", Nuclear Instruments and Methods in Physics Research, Section A., 1998, 406(2):307-310.

(56) References Cited

OTHER PUBLICATIONS

Vrenken et al., "A Design of a Compact Gantry for Proton Therapy with 2D-Scanning," *Nuclear Instruments and Methods in Physics Research*, Section A, 1999, 426(2):618-624.
Wikipedia, "*Cyclotron*" http://en.wikipedia.org/wiki/Cyclotron (originally visited Oct. 6, 2005, revisited Jan. 28, 2009), 7pages.
Wikipedia, "*Synchrotron*" http://en.wikipedia.org/wiki/Synchrotron (originally visited Oct. 6, 2005, revisited Jan. 28, 2009), 7 pages.
Worldwide Patent Assignee Search, Jan. 24, 2005, 224 pages.
Worldwide Patent Keyword Search, Jan. 24, 2005, 94 pages.
Written Opinion in PCT Application No. PCT/US2007/001628, dated Feb. 18, 2008, 11 pages.
Wu, "Conceptual Design and Orbit Dynamics in a 250 MeV Superconducting Synchrocyclotron," Ph.D. Dissertation, Michigan State University, Department of Physics and Astronomy, 1990, 172 pages.
York et al., "Present Status and Future Possibilities at NSCL-MSU," EPAC 94, Fourth European Particle Accelerator Conference, pp. 554-556, Jun. 1994.
York et al., "The NSCL Coupled Cyclotron Project—Overview and Status," *Proceedings of the Fifteenth International Conference on Cyclotrons and their Applications*, Jun. 1998, pp. 687-691.
Yudelev et al., "Hospital Based Superconducting Cyclotron for Neutron Therapy: Medical Physics Perspective," *Cyclotrons and their applications 2001, 16th International Conference. American Institute of Physics Conference Proceedings*, vol. 600, May 13-17, 2001, pp. 40-43.
Zherbin et al., "Proton Beam Therapy at the Leningrad Synchrocyclotron (Clinicomethodological Aspects and Therapeutic Results)", Aug. 1987, 32(8):17-22, (German with English abstract on pp. 21-22).
U.S. Appl. No. 13/949,450, filed Jul. 24, 2013.
U.S. Appl. No. 13/830,792, filed Mar. 14, 2013.
European Search Report from European Application No. 14171707.4 dated Nov. 4, 2014 (3 pages).
European Search Report from European Application No. 14170555.8 dated Oct. 15, 2014 (5 pages).
European Search Report from European Application No. 14171707.4 dated Nov. 28, 2014 (6 pages).
U.S. Appl. No. 61/676,377, filed Jul. 27, 2012.
Office Action with English translation from Japanese Application 2014-120409 issued on Jun. 15, 2015 (10 pages).
First Office Action of CN201410404574.5, 8 pages (Mar. 1, 2016).
Tilly, et al., "Development and verification of the pulsed scanned proton beam at The Svedberg Laboratory in Uppsala", Physics in Medicine and Biology, Phys. Med. Biol. 52, pp. 2741-2454, 2007.
Response to European Communication mailed Nov. 28, 2014 in corresponding European Application 14171707.4, filed on Mar. 24, 2015 (29 pages).
Japanese Office action with English translation in corresponding Japanese application 2014-120409 issued on Jan. 18, 2016 (11 pages).
Response with English translation to Japanese office action issued Jun. 15, 2015 in corresponding Japanese application 2014-120409, filed on Oct. 14, 2015 (23 pages).
Office Action of CN201410404574.5, 8 pages (Mar. 1, 2016).
Communication under Rule 71(3) EPC for EP14171707.4-1551, 55 pages (Oct. 5, 2016).
Second Office Action (Chinese translation) for CN201410404574.5, 5 pages (Jan. 16, 2017).
Second Office Action (English translation) for CN201410404574.5, 10 pages (Jan. 16, 2017).

\* cited by examiner

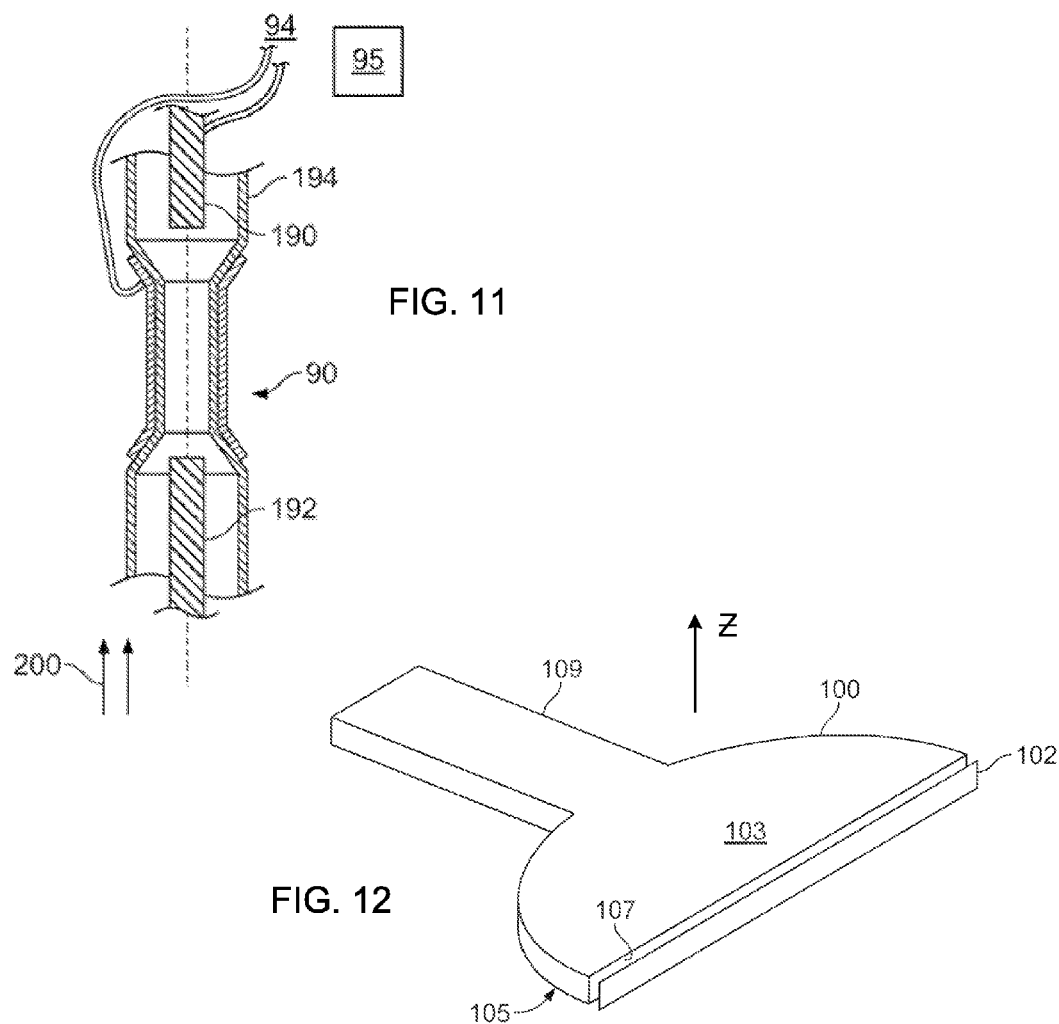

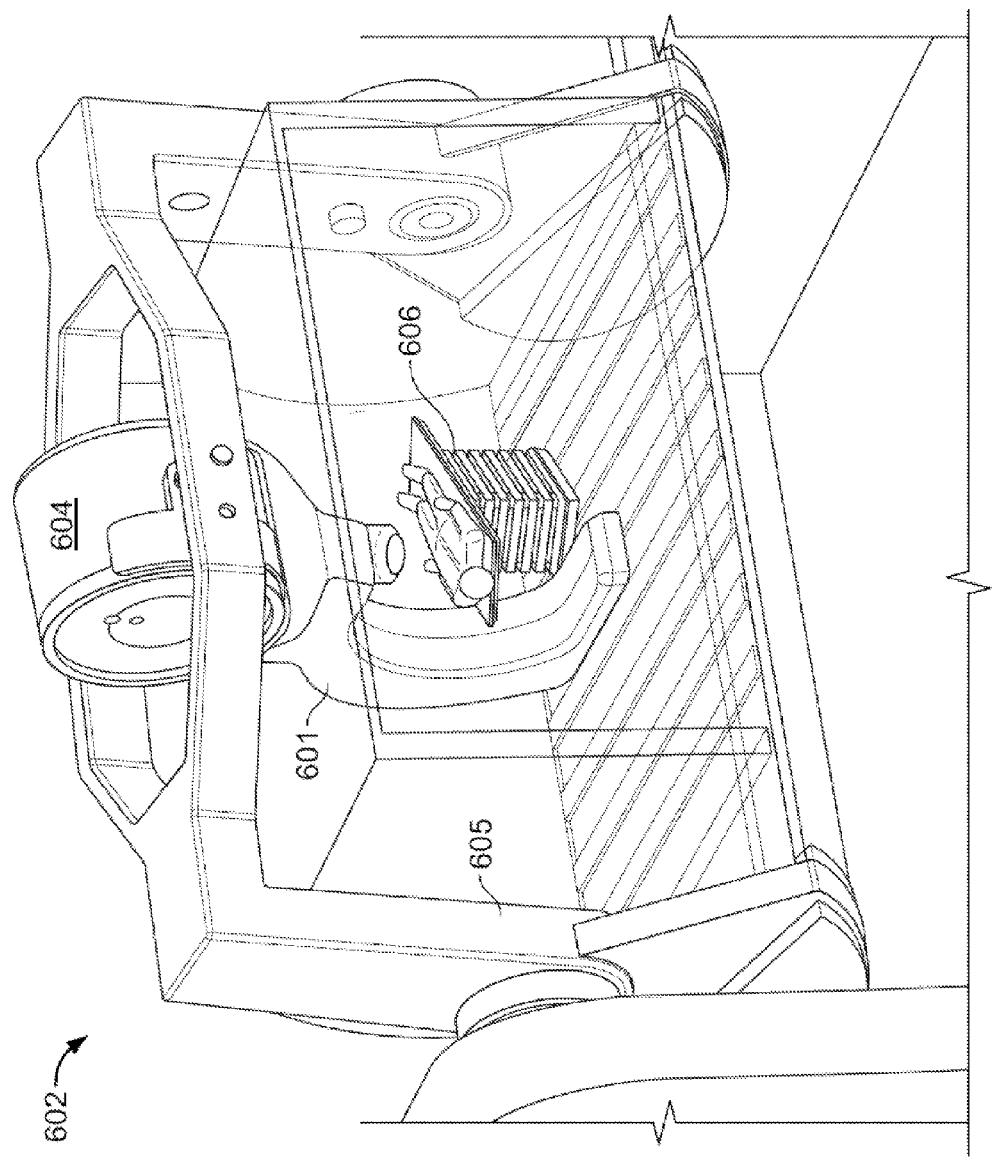

PARTICLE ACCELERATOR THAT PRODUCES CHARGED PARTICLES HAVING VARIABLE ENERGIES

TECHNICAL FIELD

This disclosure relates generally to a particle accelerator that produces charged particles having variable energies.

BACKGROUND

Particle therapy systems use an accelerator to generate a particle beam for treating afflictions, such as tumors. In operation, particles are accelerated in orbits inside a cavity in the presence of a magnetic field, and removed from the cavity through an extraction channel. Particle beams extracted from the accelerator can be used to irradiate a target volume in a body.

SUMMARY

An example synchrocyclotron includes the following: a voltage source to provide a radio frequency (RF) voltage to a cavity to accelerate particles from a particle source; a coil to receive a variable electrical current and to generate a magnetic field that is at least 4 Tesla to cause the particles to move orbitally within the cavity; and an extraction channel to receive the accelerated particles and to output the received particles from the cavity. The particles that are output from the cavity have an energy that is variable based at least on the variable electrical current applied to the coil.

An example proton therapy system includes the following: the above example synchrocyclotron; and a gantry on which the synchrocyclotron is mounted. The gantry is rotatable relative to a patient position. The particles are protons and are output essentially directly from the synchrocyclotron to the patient position.

The variable electrical current can include a fixed portion and a variable portion, and the variable portion of the electrical current can vary within a range that causes the magnetic field at an extraction radius of the synchrocyclotron to change by between about 5% and 35% of a maximum value at the extraction radius. The magnetic field at the extraction radius can change by between about 0.2 Tesla and about 1.4 Tesla or by between about 0.6 and about 4.2 Tesla. The coil can include a first set of coils and a second set of coils. The first set can be configured to receive a fixed portion of the variable electrical current, and the second set can be configured to receive a variable portion of the variable electrical current. The variable portion of the electrical current can vary within a range that causes the magnetic field at an extraction radius of the synchrocyclotron to change by between about 5% and 35% of a maximum value at the extraction radius. The coil can include one or more sets of coils, and at least one set of coils can be superconducting and can consist of between 2 and 10 million ampere turns. The magnetic field can have a magnitude having a range of about 4 Tesla to about 20 Tesla. The energy of the particles that are output from the cavity can vary continuously between about 115 MeV and about 250 MeV, e.g., at a rate up to 20 MeV per second. The energy of the particles that are output from the cavity can vary non-continuously between about 115 MeV and about 250 MeV. The energy of the particles can vary at a step size of about 10 MeV to about 80 MeV. Each variation of the energy by one step can take less than 30 minutes. The coil can include a superconducting coil. The voltage source can be configured to sweep the RF voltage over a frequency range in a cycle. The voltage source can be configured to sweep the RF voltage over a different frequency range corresponding to each different energy at which the particles are output from the cavity. Each frequency range can include a lower boundary and an upper boundary, and the lower boundary can be within a range of about 40 MHz to about 250 MHz, e.g., about 73 MHz to about 150 MHz, and the upper boundary can be within a range of about 56 MHz to about 340 MHz, e.g., about 131 MHz to about 196 MHz. One or more reactive elements can be coupled to the voltage source to sweep the RF voltage over a frequency range. The one or more reactive elements can be configured to select the frequency range for a corresponding energy at which the particles are output from the cavity. The one or more reactive elements can include a variable capacitor or inductor. The coil can include a first set of coils and a second set of coils, with the first set being superconducting and configured to receive a fixed portion of the variable electrical current, and the second set being superconducting or non-superconducting and configured to receive a variable portion of the variable electrical current.

Two or more of the features described in this disclosure, including those described in this summary section, may be combined to form implementations not specifically described herein.

Control of the various systems described herein, or portions thereof, may be implemented via a computer program product that includes instructions that are stored on one or more non-transitory machine-readable storage media, and that are executable on one or more processing devices. The systems described herein, or portions thereof, may be implemented as an apparatus, method, or electronic system that may include one or more processing devices and memory to store executable instructions to implement control of the stated functions.

The details of one or more implementations are set forth in the accompanying drawings and the description below. Other features, objects, and advantages will be apparent from the description and drawings, and from the claims.

DESCRIPTION OF DRAWINGS

FIG. 11 is a cross-sectional view of an ion source.

FIG. 12 is a perspective view of a dee plate and a dummy dee.

FIG. 17 shows a patient positioned within an inner gantry in a treatment room.

DETAILED DESCRIPTION

Overview

Figure 1:
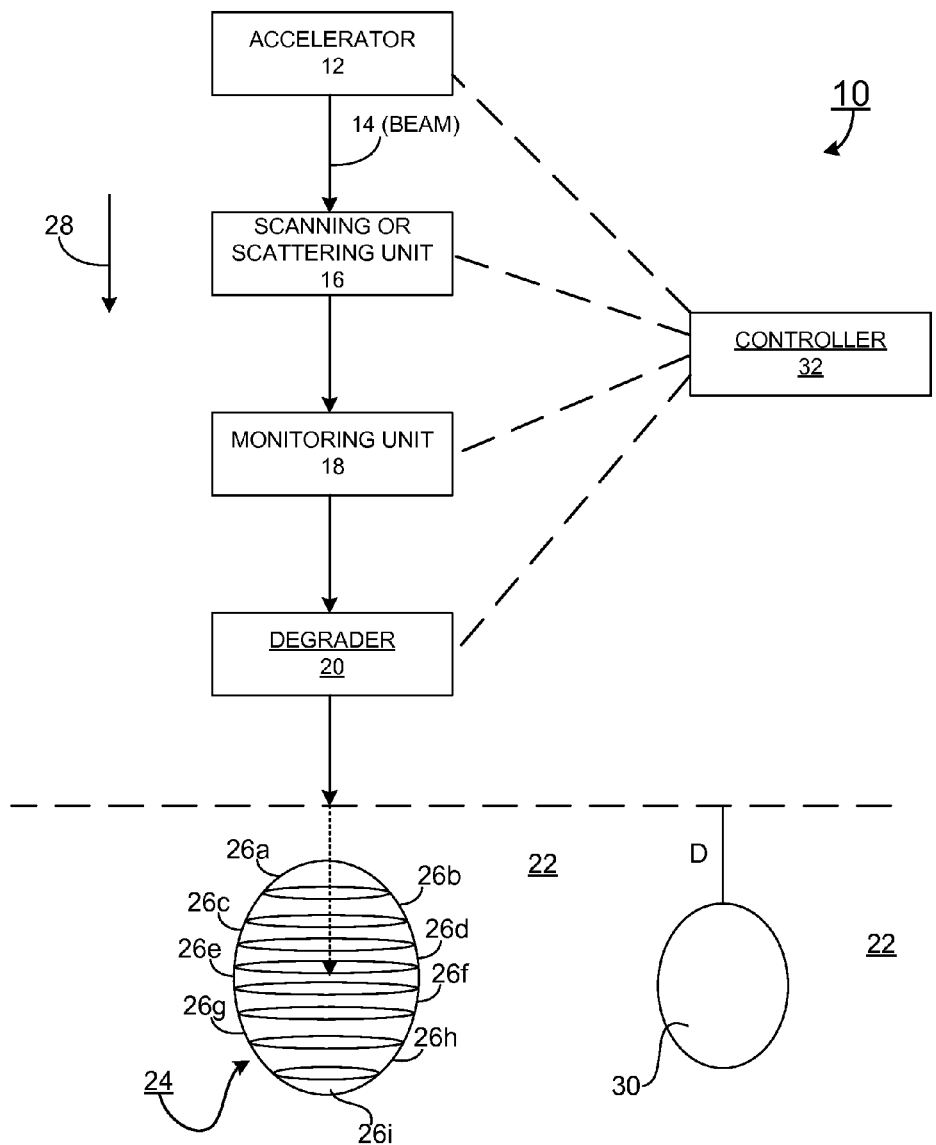
FIG. 1 is a block diagram showing an example of a treatment system.

Described herein is an example of a particle accelerator for use in a treatment system, such as a proton or ion therapy system. The example particle therapy system includes a particle accelerator—in this example, a synchrocyclotron—mounted on a gantry. The gantry enables the accelerator to be rotated around a patient position, as explained in more detail below. In some implementations, the gantry is steel and has two legs mounted for rotation on two respective bearings that lie on opposite sides of a patient. The particle accelerator is supported by a steel truss that is long enough to span a treatment area in which the patient lies and that is attached at both ends to the rotating legs of the gantry. As a result of rotation of the gantry around the patient, the particle accelerator also rotates.

In an example implementation, the particle accelerator (e.g., the synchrocyclotron) includes a cryostat that holds a superconducting coil for conducting a current that generates a magnetic field (B). In this example, the cryostat uses liquid helium (He) to maintain the coil at superconducting temperatures, e.g., 4° Kelvin (K). Magnetic pole pieces are located inside the cryostat under room temperature, and define a cavity in which particles are accelerated. In some implementations, the maximum magnetic field generated in the accelerator is at least 4 Tesla and can be up to 20 Tesla or higher, e.g., between 4 Tesla and 20 Tesla or between 6 Tesla and 20 Tesla.

In this example implementation, the particle accelerator includes a particle source (e.g., a Penning Ion Gauge—PIG source) to provide a plasma column to the cavity. Hydrogen gas is ionized to produce the plasma column. A power source provides a radio frequency (RF) voltage to the cavity to accelerate particles from the plasma column. As noted, in this example, the particle accelerator is a synchrocyclotron. Accordingly, the RF voltage is swept across a range of frequencies to account for relativistic effects on the particles (e.g., increasing particle mass) when accelerating particles from the column. The magnetic field produced by running current through the superconducting coil causes particles accelerated from the plasma column to accelerate orbitally within the cavity.

A magnetic field regenerator ("regenerator") is positioned near the outside of the cavity (e.g., at an interior edge thereof) to adjust the existing magnetic field inside the cavity to thereby change locations (e.g., the pitch and angle) of successive orbits of the particles accelerated from the plasma column so that, eventually, the particles output to an extraction channel that passes through the cryostat. The regenerator may increase the magnetic field at a point in the cavity (e.g., it may produce a magnetic field "bump" at an area of the cavity), thereby causing each successive orbit of particles at that point to precess outwardly toward the entry point of the extraction channel until it reaches the extraction channel. The extraction channel receives particles accelerated from the plasma column and outputs the received particles from the cavity as a particle beam.

The energy of the extracted particle beam (or the particle beam output from the accelerator) can affect the use of the particle beam in treatments. Generally, the energy of the particle beam (or particles in the particle beam) does not increase after the extraction. However, the energy may be reduced based on treatment needs after the extraction and before the treatment. Referring to FIG. 1, a sample treatment system 10 includes an accelerator 12, e.g., a synchrocyclotron, from which a particle (e.g., proton) beam 14 having a variable energy is extracted to irradiate a target volume 24 of a body 22. Optionally, one or more additional devices, such as a scanning unit 16 or a scattering unit 16, one or more monitoring units 18, and an energy degrader 20, are placed along the irradiation direction 28. The devices intercept the cross-section of the extracted beam 14 and alter one or more properties of the extracted beam for the treatment.

A target volume to be irradiated by a particle beam for treatment typically has a three-dimensional configuration. In some situations, to carry out the treatment, the target volume is divided into layers along the irradiation direction of the particle beam and the irradiation can be done on a layer-by-layer basis. For certain types of particles, such as protons, along the irradiation direction the penetration depth (or which layer the beam reaches) within the target volume is largely determined by the energy of the particle beam. The particle beam of a given energy does not reach substantially beyond the corresponding penetration depth. To move the beam irradiation from one layer to another layer of the target volume, the energy of the particle beam is changed.

In the example shown in FIG. 1, the target volume 24 is divided into nine layers 26a-26i along the irradiation direction 28. The irradiation typically starts from the deepest layer 26i, one layer at a time, gradually to the shallower layers and finishes with the shallowest layer 26a. Before application to the body 22, the energy of the particle beam 14 is controlled to be at a level to allow the particle to stop at a desired layer, e.g., the layer 26d, without substantially penetrating further into the body or the target volume, e.g., the layers 26e-26i or deeper into the body. In some examples, the desired energy of the particle beam 14 decreases as the treatment layer becomes shallower relative to the particle acceleration. Typically, the beam energy difference for treating adjacent layers of the target volume 24 is about 3 MeV to about 100 MeV, e.g., about 10 MeV to about 80 MeV, although other differences may also be possible, depending on, e.g., the thickness of the layers and the properties of the beam.

The energy variation for treating different layers of the target volume 24 can be performed at the accelerator 12 so that, in some implementations, no additional energy variation is required after the particle beam is extracted from the accelerator 12. The optional energy degrader 20 in the treatment system 10 may be eliminated from the system. In some implementations, the accelerator 12 can output particle beams having an energy that vary between about 100 MeV and about 300 MeV, e.g., between about 115 MeV and about 250 MeV. The variation can be continuous or non-continuous, e.g., one step at a time. In some implementations, the variation, continuous or non-continuous, can take place at a relatively high rate, e.g., up to about 50 MeV per second or up to about 20 MeV per second. Non-continuous variation can take place one step at a time with a step size of about 10 MeV to about 80 MeV.

When irradiation is complete in one layer, the accelerator 12 can vary the energy of the particle beam for irradiating a next layer, e.g., within several seconds or within less than one second. In some implementations, the treatment of the target volume 24 can be continued without substantial interruption or even without any interruption. In some situations, the step size of the non-continuous energy variation is selected to correspond to the energy difference needed for irradiating two adjacent layers of the target volume 24. For example, the step size can be the same or a fraction of the energy difference.

In some implementations, the accelerator 12 and the degrader 20 collectively vary the energy of the beam 14. For example, the accelerator 12 provides a coarse adjustment and the degrader 20 provides a fine adjustment or vice versa. In this example, the accelerator 12 can output the particle beam that varies energy with a variation step of about 10-80 MeV, and the degrader 20 adjusts (e.g., reduces) the energy of the beam at a variation step of about 2-10 MeV.

The reduced use (or absence) of the degrader, which can be range shifters, can facilitate maintaining the property and quality of the output beam from the accelerator, e.g., beam intensity. The control of the particle beam can be performed at the accelerator. Side effects, e.g., from neutrons generated when the particle beam passes the degrader 20 can be reduced or removed.

The energy of the particle beam 14 may also need adjustment when the treatment system 10 treats another target volume 30 in another body or body part 22' after completing the treatment in the target volume 24. The target volumes 24, 30 may be in the same body (or patient), or may belong to different patients. It is possible that the depth D of the target volume 30 from a surface of the body 22's is different for that of the target volume 24. Although some energy adjustment may be done by the degrader 20, the degrader 12 may only reduce the beam energy and not increase the beam energy. Sometimes the highest beam energy for treating the target volume 30 may be higher than the highest beam energy for treating the target volume 24. In such a situation, the accelerator 12 increases the output beam energy after treating the target volume 24 and before treating the target volume 30. In other situations, the highest beam energy required for treating the target volume 30 may be lower than the highest beam energy of the target volume. Although the degrader 20 can reduce the energy, the accelerator 12 can be adjusted to output a lower beam energy to reduce or eliminate the use of the degrader 20. The division of the target volumes 24, 30 into layers can be different or the same. And the target volume 30 can be treated similarly on a layer by layer basis to the treatment of the target volume 24.

The treatment of the different target volumes 24, 30 on the same patient may be substantially continuous, e.g., with the stopping time between the two volumes being no longer than about 30 minutes or less, e.g., 25 minutes or less, 20 minutes or less, 15 minutes or less, 10 minutes or less, 5 minutes or less, or 1 minute or less. As is explained in detail further below, the accelerator 12 can be mounted on a movable gantry and the movement of the gantry moves the accelerator to aim at different target volumes. In some situations, the accelerator 12 can complete the energy adjustment of the output beam 14 during the time the treatment system makes adjustment (such as moving the gantry) after completing the treatment of the target volume 24 and before starting treating the target volume 30. As soon as the alignment of the accelerator and the target volume 30 is done, the treatment can begin with the adjusted, desired beam energy. Beam energy adjustment for different patients can also be completed relatively efficiently. In some examples, all adjustments, including increasing/reducing beam energy and/or moving the gantry are done within about 30 minutes, e.g., within about 25 minutes, within about 20 minutes, within about 15 minutes, within about 10 minutes or within about 5 minutes.

In the same layer of a target volume, an irradiation dose is applied by moving the beam across the two-dimensional surface of the layer (which is sometimes called scanning beam) using a scanning unit 16. Alternatively, the layer can be irradiated by passing the extracted beam through one or more scatterers of the scattering unit 16 (which is sometimes called scattering beam).

The beam property, such as energy and intensity, can be selected before a treatment or can be adjusted during the treatment by controlling the accelerator 12 and/or other devices, such as the scanning unit/scatterer(s) 16, the degrader 20, and others not shown in the figure. In some implementations, the system 10 includes a controller 32, such as a computer, in communication with one or more devices in the system. Sometimes the control can be based on results of the monitoring performed by the one or more monitors 18, e.g., monitoring of the beam intensity, dose, beam location in the target volume, etc. Although the monitors 18 are shown to be between the device 16 and the degrader 20, one or more monitors can be placed at other locations of the beam irradiation path. The controller 32 can also store a treatment plan for one or more target volumes (of the same patient and/or different patients). The treatment plan can be determined before the treatment starts and can include parameters such as the shape of the target volume, the number of layers, the irradiation dose for each layer, the number of times each layer is irradiated, etc. The adjustment of a beam property within the system 10 can be performed based on the treatment plan. Additional adjustment can be made during the treatment, e.g., when deviation from the treatment plan is detected.

In some implementations, the accelerator 12 varies the energy of the output particle beam by varying the magnetic field in which the particle beam is accelerated. In particular, one or more sets of coils are used to receive variable electrical current to produce a variable magnetic field in the cavity. In some examples, one set of coils receive a fixed electrical current, while one or more other sets of coils receives a variable current so that the total current received by the coil sets varies. In some implementations, all sets of coils are superconducting. In other implementations, some sets of coils, such as the set for the fixed electrical current, are superconducting, while other sets of coils, such as the one or more sets for the variable current, are non-superconducting. Sometimes all sets of coils are non-superconducting.

Generally, the magnitude of the magnetic field is scalable with the magnitude of the electrical current. Adjusting the total electric current of the coils in a predetermined range can generate a magnetic field that varies in a corresponding, predetermined range. In some situations, a continuous adjustment of the electrical current can lead to a continuous variation of the magnetic field and a continuous variation of the output beam energy. Alternatively, when the electrical current applied to the coils is adjusted in a non-continuous, step manner, the magnetic field and the output beam energy also varies accordingly in a non-continuous manner. The scaling of the magnetic field to the current can allow the variation of the beam energy to be carried out relatively precisely, although sometimes minor adjustment other than the input current may be needed, the details of which are discussed below.

Furthermore, to output particle beams having a variable energy, the accelerator 12 is configured to apply the RF voltages that sweep over different ranges of frequencies, with each range corresponding to a different output beam energy. For example, if the accelerator 12 is configured to produce three different output beam energies, the RF voltage is capable of sweeping over three different ranges of frequencies. In another example, corresponding to continuous beam energy variations, the RF voltage sweeps over frequency ranges that continuously change. The different frequency ranges may have different lower frequency and/or upper frequency boundaries.

The particle beams having different energies can be extracted from the accelerator 12 without altering the features of the regenerator that is used for extracting particle beams having a single energy. In other implementations, the regenerator can be moved to disturb particle orbits or iron plugs can be added or removed to change the magnetic field bump based on the variable particle energy.

As an example, table 1 shows three energy levels at which the accelerator 12 can output particle beams. The corresponding parameters for producing the three energy levels are also listed. In particular, the magnet current refers to the total electrical current applied to the one or more coil sets in the accelerator 12; the maximum and minimum frequencies define the ranges in which the RF voltage sweeps; and r is the radial distance of a location to a center of the cavity in which the particles are accelerated.

TABLE 1

Examples of beam energies and respective parameters.

| Beam Energy (MeV) | Magnet Current (Amps) | Maximum Frequency (MHz) | Minimum Frequency (MHz) | Magnetic Field at r = 0 mm (Tesla) | Magnetic Field at r = 298 mm (Tesla) |
|---|---|---|---|---|---|
| 250 | 1990 | 132 | 99 | 8.7 | 8.2 |
| 235 | 1920 | 128 | 97 | 8.4 | 8.0 |
| 211 | 1760 | 120 | 93 | 7.9 | 7.5 |

Details of an example particle accelerator that produces charged particles having variable energies are described below. The accelerator can be a synchrocyclotron and the particles may be protons. The particles are formed into beams for use in treatments. The energy of the beam output from the particle accelerator can be varied during the treatment of one target volume in a patient, or between treatments of different target volumes of the same patient or different patients. In some implementations, settings of the accelerator are changed to vary the beam energy when no beam (or particles) is output from the accelerator. The energy variation can be continuous or non-continuous over a desired range.

Figure 2:
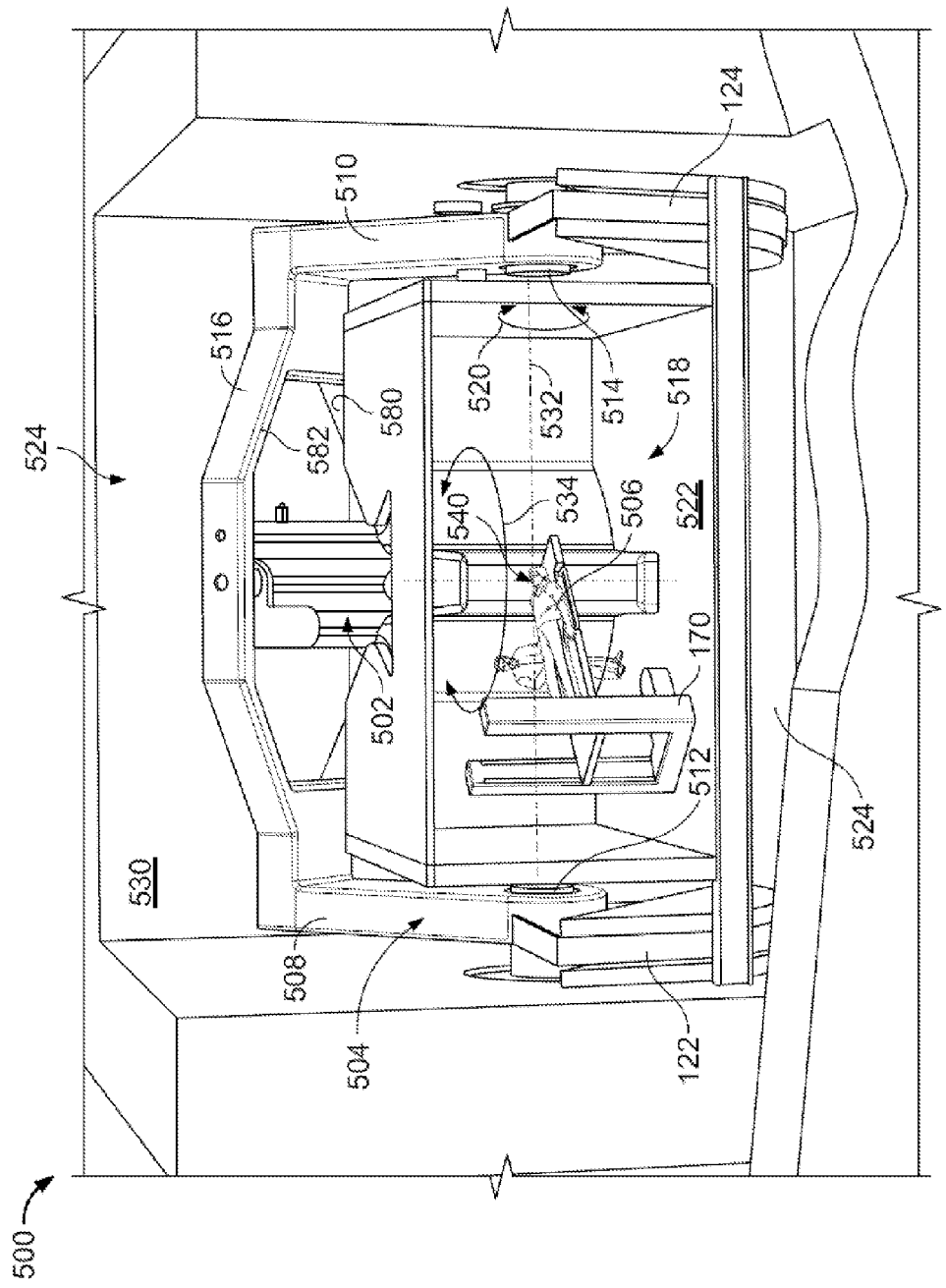
FIG. 2 is a perspective view of a therapy system.
Figure 3:
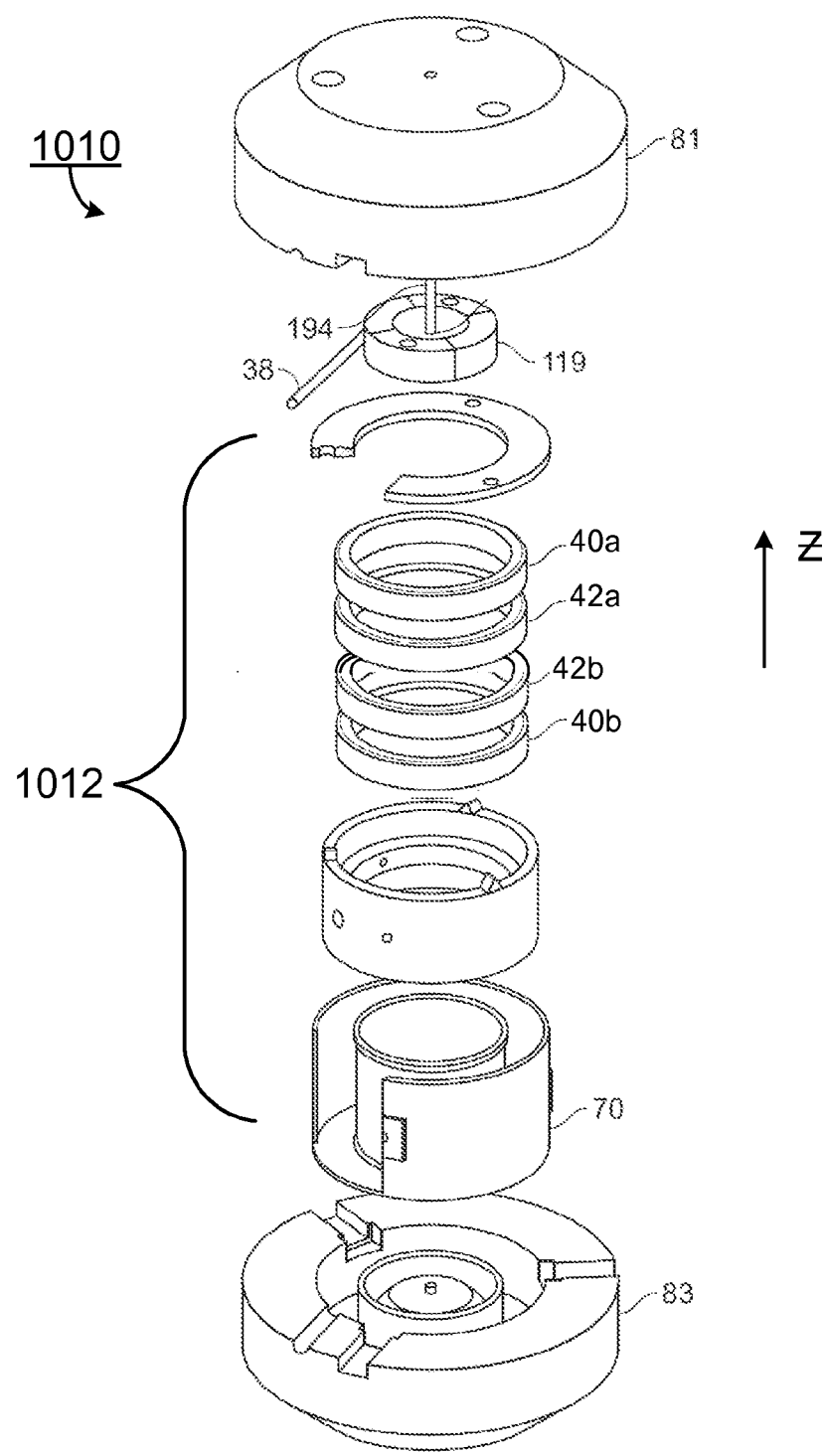
FIG. 3 is an exploded perspective view of components of a synchrocyclotron.

Referring to FIG. 2, a charged particle radiation therapy system 500 includes a beam-producing particle accelerator 502 having a weight and size small enough to permit it to be mounted on a rotating gantry 504 with its output directed straight (that is, essentially directly) from the accelerator housing toward a patient 506.

In some implementations, the steel gantry has two legs 508, 510 mounted for rotation on two respective bearings 512, 514 that lie on opposite sides of the patient. The accelerator is supported by a steel truss 516 that is long enough to span a treatment area 518 in which the patient lies (e.g., twice as long as a tall person, to permit the person to be rotated fully within the space with any desired target area of the patient remaining in the line of the beam) and is attached stably at both ends to the rotating legs of the gantry.

In some examples, the rotation of the gantry is limited to a range 520 of less than 360 degrees, e.g., about 180 degrees, to permit a floor 522 to extend from a wall of the vault 524 that houses the therapy system into the patient treatment area. The limited rotation range of the gantry also reduces the required thickness of some of the walls (which are never directly aligned with the beam, e.g., wall 530), which provide radiation shielding of people outside the treatment area. A range of 180 degrees of gantry rotation is enough to cover all treatment approach angles, but providing a larger range of travel can be useful. For example the range of rotation may be between 180 and 330 degrees and still provide clearance for the therapy floor space.

The horizontal rotational axis 532 of the gantry is located nominally one meter above the floor where the patient and therapist interact with the therapy system. This floor is positioned about 3 meters above the bottom floor of the therapy system shielded vault. The accelerator can swing under the raised floor for delivery of treatment beams from below the rotational axis. The patient couch moves and rotates in a substantially horizontal plane parallel to the rotational axis of the gantry. The couch can rotate through a range 534 of about 270 degrees in the horizontal plane with this configuration. This combination of gantry and patient rotational ranges and degrees of freedom allow the therapist to select virtually any approach angle for the beam. If needed, the patient can be placed on the couch in the opposite orientation and then all possible angles can be used.

In some implementations, the accelerator uses a synchrocyclotron configuration having a very high magnetic field superconducting electromagnetic structure. Because the bend radius of a charged particle of a given kinetic energy is reduced in direct proportion to an increase in the magnetic field applied to it, the very high magnetic field superconducting magnetic structure permits the accelerator to be made smaller and lighter. The synchrocyclotron uses a magnetic field that is uniform in rotation angle and falls off in strength with increasing radius. Such a field shape can be achieved regardless of the magnitude of the magnetic field, so in theory there is no upper limit to the magnetic field strength (and therefore the resulting particle energy at a fixed radius) that can be used in a synchrocyclotron.

Superconducting materials lose their superconducting properties in the presence of very high magnetic fields. High performance superconducting wire windings are used to allow very high magnetic fields to be achieved.

Superconducting materials typically need to be cooled to low temperatures for their superconducting properties to be realized. In some examples described here, cryo-coolers are used to bring the superconducting coil windings to temperatures near absolute zero. Using cryo-coolers can reduce complexity and cost.

The synchrocyclotron is supported on the gantry so that the beam is generated directly in line with the patient. The gantry permits rotation of the cyclotron about a horizontal rotational axis that contains a point (isocenter 540) within, or near, the patient. The split truss that is parallel to the rotational axis, supports the cyclotron on both sides.

Because the rotational range of the gantry is limited, a patient support area can be accommodated in a wide area around the isocenter. Because the floor can be extended broadly around the isocenter, a patient support table can be positioned to move relative to and to rotate about a vertical axis 542 through the isocenter so that, by a combination of gantry rotation and table motion and rotation, any angle of beam direction into any part of the patient can be achieved. The two gantry arms are separated by more than twice the height of a tall patient, allowing the couch with patient to rotate and translate in a horizontal plane above the raised floor.

Limiting the gantry rotation angle allows for a reduction in the thickness of at least one of the walls surrounding the treatment room. Thick walls, typically constructed of concrete, provide radiation protection to individuals outside the treatment room. A wall downstream of a stopping proton beam may be about twice as thick as a wall at the opposite end of the room to provide an equivalent level of protection. Limiting the range of gantry rotation enables the treatment room to be sited below earth grade on three sides, while allowing an occupied area adjacent to the thinnest wall reducing the cost of constructing the treatment room.

Variable Energy

In the example shown in FIG. 2, the superconducting synchrocyclotron 502 outputs particle beams that have a variable energy. The range of the variable energy can have an upper boundary that is about 200 MeV to about 300 MeV or higher, e.g., 200 MeV, about 205 MeV, about 210 MeV, about 215 MeV, about 220 MeV, about 225 MeV, about 230 MeV, about 235 MeV, about 240 MeV, about 245 MeV, about 250 MeV, about 255 MeV, about 260 MeV, about 265 MeV, about 270 MeV, about 275 MeV, about 280 MeV, about 285 MeV, about 290 MeV, about 295 MeV, or about 300 MeV or higher. The range can also have a lower boundary that is about 100 MeV or lower to about 200 MeV, e.g., about 100 MeV or lower, about 105 MeV, about 110 MeV, about 115 MeV, about 120 MeV, about 125 MeV, about 130 MeV, about 135 MeV, about 140 MeV, about 145 MeV, about 150 MeV, about 155 MeV, about 160 MeV, about 165 MeV, about 170 MeV, about 175 MeV, about 180 MeV, about 185 MeV, about 190 MeV, about 195 MeV, about 200 MeV.

In some situations, the variation is non-continuous and the variation step can have a size of about 10 MeV or lower, about 15 MeV, about 20 MeV, about 25 MeV, about 30 MeV, about 35 MeV, about 40 MeV, about 45 MeV, about 50 MeV, about 55 MeV, about 60 MeV, about 65 MeV, about 70 MeV, about 75 MeV, or about 80 MeV or higher. Varying the energy by one step size can take no more than 30 minutes, e.g., about 25 minutes or less, about 20 minutes or less, about 15 minutes or less, about 10 minutes or less, about 5 minutes or less, about 1 minute or less, or about 30 seconds or less. In other situations, the variation is continuous and the accelerator can adjust the energy of the particle beam at a relatively high rate, e.g., up to about 50 MeV per second, up to about 45 MeV per second, up to about 40 MeV per second, up to about 35 MeV per second, up to about 30 MeV per second, up to about 25 MeV per second, up to about 20 MeV per second, up to about 15 MeV per second, or up to about 10 MeV per second. The accelerator can be configured to adjust the particle energy both continuously and non-continuously. For example, a combination of the continuous and non-continuous variation can be used in a treatment of one target volume or in treatments of different target volumes. Flexible treatment planning and flexible treatment can be achieved.

The particle accelerator outputting a particle beam having a variable energy can provide accuracy in irradiation treatment and reduce the number of additional devices (other than the accelerator) for the treatment. For example, the use of degraders for changing the energy of an outputted particle beam may be reduced or eliminated. The properties of the particle beam, such as intensity, focus, etc. can be controlled at the particle accelerator and the particle beam can reach the target volume without substantial disturbance from the additional devices. The relatively high variation rate of the beam energy can reduce treatment time and allow for efficient use of the treatment system.

Variable Magnetic Field

In some implementations, the accelerator, such as the synchrocyclotron 502 of FIG. 2, accelerates particles or particle beams to variable energy levels by varying the magnetic field in the accelerator, which can be achieved by varying the electrical current applied to coils for generating the magnetic field. As shown in FIGS. 3, 4, 5, 6, and 7, an example synchrocyclotron 1010 (502 in FIG. 2) includes a magnet system 1012 that contains a particle source 90, a radiofrequency drive system 91, and a beam extraction system 38. The magnetic field established by the magnet system 1012 can vary by about 5% to about 35% of a maximum value of the magnetic field that two sets of coils 40a and 40b, and 42a and 42b are capable of generating. The magnetic field established by the magnet system has a shape appropriate to maintain focus of a contained proton beam using a combination of the two sets of coils and a pair of shaped ferromagnetic (e.g., low carbon steel) pole faces 44, 46.

Each set of coils is a split pair of annular coils to receive electrical current. In some situations, both sets of coils are superconducting. In other situations, only one set of the coils is superconducting and the other set is non-superconducting or normal conducting (also discussed further below). It is also possible that both sets of coils are non-superconducting. Suitable superconducting materials for use in the coils include niobium-3 tin ($Nb_3Sn$) and/or niobium-titanium. Other normal conducting materials can include copper. Examples of the coil set constructions are described further below.

The two sets of coils can be electrically connected serially or in parallel. In some implementations, the total electrical current received by the two sets of coils can include about 2 million ampere turns to about 10 million ampere turns, e.g., about 2.5 to about 7.5 million ampere turns or about 3.75 million ampere turns to about 5 million ampere turns. In some situations, one set of coils is configured to receive a fixed (or constant) portion of the total variable electrical current, while the other set of coils is configured to receive a variable portion of the total electrical current. The total electrical current of the two coil sets varies with the variation of the current in one coil set. In other situations, the electrical current applied to both sets of coils can vary. The variable total current in the two sets of coils can generate a magnetic field having a variable magnitude, which in turn varies the acceleration pathways of the particles and produces particles having variable energies.

Generally, the magnitude of the magnetic field generated by the coil(s) is scalable to the magnitude of the total electrical current applied to the coil(s). Based on the scalability, in some implementations, linear variation of the magnetic field strength can be achieved by linearly changing the total current of the coil sets. The total current can be adjusted at a relatively high rate that leads to a relatively high-rate adjustment of the magnetic field and the beam energy.

In the example shown in table 1, the ratio between values of the current and the magnetic field at the geometric center of the coil rings is: 1990:8.7 (approximately 228.7:1); 1920:8.4 (approximately 228.6:1); 1760:7.9 (approximately 222.8:1). Accordingly, adjusting the magnitude of the total current applied to a superconducting coil(s) can proportionally (based on the ratio) adjust the magnitude of the magnetic field.

Figure 8:
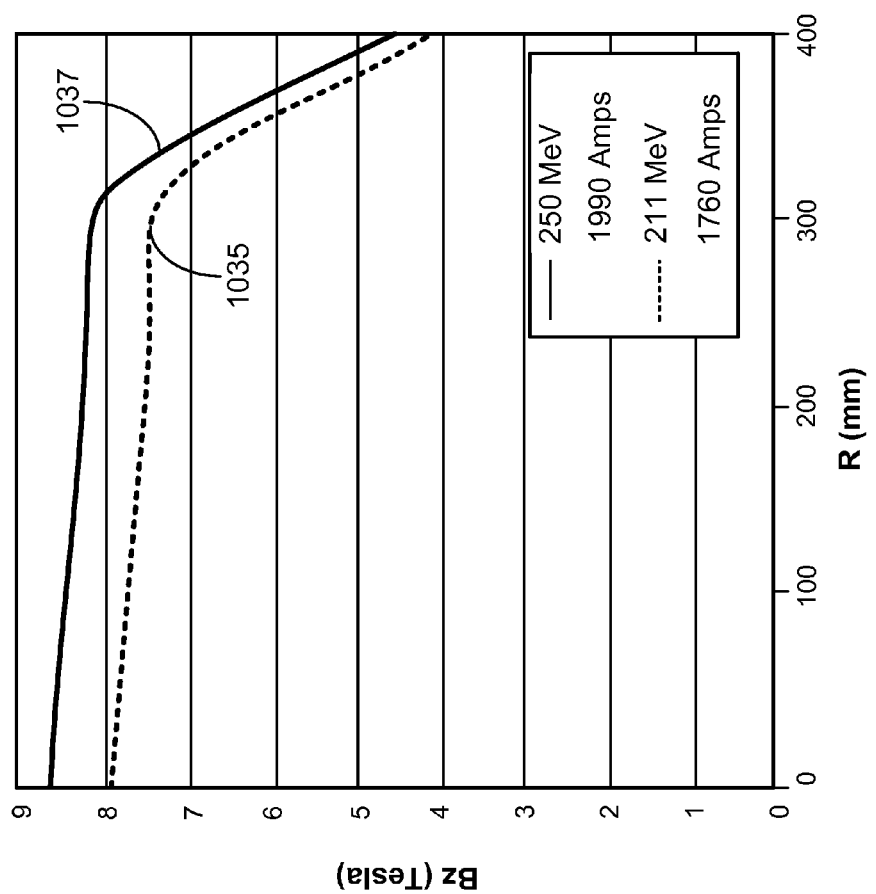
FIG. 8 is a plot of the magnitudes of the magnetic field at different locations in an acceleration chamber when different total electrical current is applied in the accelerator.

The scalability of the magnetic field to the total electrical current in the example of table 1 is also shown in the plot of FIG. 8, where $B_Z$ is the magnetic field along the Z direction;

and R is the radial distance measured from a geometric center of the coil rings along a direction perpendicular to the Z direction. The magnetic field has the highest value at the geometric center, and decreases as the distance R increases. The curves 1035, 1037 represent the magnetic field generated by the same coil sets receiving different total electrical current: 1760 Amperes and 1990 Amperes, respectively. The corresponding energies of the extracted particles are 211 MeV and 25 MeV, respectively. The two curves 1035, 1037 have substantially the same shape and the different parts of the curves 1035, 1037 are substantially parallel. As a result, either the curve 1035 or the curve 1037 can be linearly shifted to substantially match the other curve, indicating that the magnetic field is scalable to the total electrical current applied to the coil sets.

In some implementations, the scalability of the magnetic field to the total electrical current may not be perfect. For example, the ratio between the magnetic field and the current calculated based on the example shown in table 1 is not constant. Also, as shown in FIG. 8, the linear shift of one curve may not perfectly match the other curve. In some implementations, the total current is applied to the coil sets under the assumption of perfect scalability. The target magnetic field (under the assumption of perfect scalability) can be generated by additionally altering the features, e.g., geometry, of the coils to counteract the imperfection in the scalability. As one example, iron rods can be inserted or removed from one or both of the pole pieces. The features of the coils can be altered at a relatively high rate so that the rate of the magnetic field adjustment is not substantially affected as compared to the situation in which the scalability is perfect and only the electrical current needs to be adjusted. In the example of iron rods, the rods can be added or removed at the time scale of seconds or minutes, e.g., within 5 minutes, within 1 minute, less than 30 seconds, or less than 1 second.

In some implementations, settings of the accelerator, such as the current applied to the coil sets, can be chosen based on the substantial scalability of the magnetic field to the total electrical current in the coil sets.

Generally, to produce the total current that varies within a desired range, any combination of current applied to the two coil sets can be used. In an example, the coil set 42a, 42b can be configured to receive a fixed electrical current corresponding to a lower boundary of a desired range of the magnetic field. In the example shown in table 1, the fixed electrical current is 1760 Amperes. In addition, the coil set 40a, 40b can be configured to receive a variable electrical current having an upper boundary corresponding to a difference between an upper boundary and a lower boundary of the desired range of the magnetic field. In the example shown in table 1, the coil set 40a, 40b is configured to receive electrical current that varies between 0 Ampere and 230 Amperes.

In another example, the coil set 42a, 42b can be configured to receive a fixed electrical current corresponding to an upper boundary of a desired range of the magnetic field. In the example shown in table 1, the fixed current is 1990 Amperes. In addition, the coil set 40a, 40b can be configured to receive a variable electrical current having an upper boundary corresponding to a difference between a lower boundary and an upper boundary of the desired range of the magnetic field. In the example shown in table 1, the coil set 40a, 40b is configured to receive electrical current that varies between −230 Ampere and 0 Ampere.

The total variable magnetic field generated by the variable total current for accelerating the particles can have a maximum magnitude greater than 4 Tesla, e.g., greater than 5 Tesla, greater than 6 Tesla, greater than 7 Tesla, greater than 8 Tesla, greater than 9 Tesla, or greater than 10 Tesla, and up to about 20 Tesla or higher, e.g., up to about 18 Tesla, up to about 15 Tesla, or up to about 12 Tesla. In some implementations, variation of the total current in the coil sets can vary the magnetic field by about 0.2 Tesla to about 4.2 Tesla or more, e.g., about 0.2 Tesla to about 1.4 Tesla or about 0.6 Tesla to about 4.2 Tesla. In some situations, the amount of variation of the magnetic field can be proportional to the maximum magnitude.

Furthermore, at a given maximum magnitude of the magnetic field, the magnetic field strength is generally a function of distance from a geometric center of the accelerator and can be affected by the choice of geometry of coils 40a, 40b, 42a, and 42b and shape and material of magnetic poles. An example of the magnetic field strength variation as a function of the distance is shown in FIG. 8.

An example of the construction of the two sets of coils is discussed below. The two coil sets are centered on a common axis 47 and are spaced apart along the axis. In the example shown in FIGS. 9 and 10, the coil sets are formed by of $Nb_3Sn$-based superconducting 0.8 mm diameter strands 48 (that initially comprise a niobium-tin core surrounded by a copper sheath) deployed in a twisted cable-in-channel conductor geometry. After seven individual strands are cabled together, they are heated to cause a reaction that forms the final (brittle) superconducting material of the wire. After the material has been reacted, the wires are soldered into the copper channel (outer dimensions 3.18×2.54 mm and inner dimensions 2.08×2.08 mm) and covered with insulation 52 (in this example, a woven fiberglass material). The copper channel containing the wires 53 is then wound in two coil sets each having a rectangular cross-section of 8.55 cm×19.02 cm, having 26 layers and 49 turns per layer. The wound coil sets are then vacuum impregnated with an epoxy compound 54. The finished coil sets are mounted on an annular stainless steel reverse bobbin 56. Heater blankets 55 are placed at intervals in the layers of the windings to protect the assembly in the event of a magnet quench.

The wound coil sets are then vacuum impregnated with an epoxy compound. Each entire coil set can then be covered with copper sheets to provide thermal conductivity and mechanical stability and then contained in an additional layer of epoxy. The precompression of the coil sets can be provided by cooling the coil set to a low temperature and fitting the coil sets within the reverse bobbin. The reverse bobbin inner diameter is chosen so that when the entire mass is cooled to 4 K, the reverse bobbin stays in contact with the coil sets and provides some compression.

Figure 6:
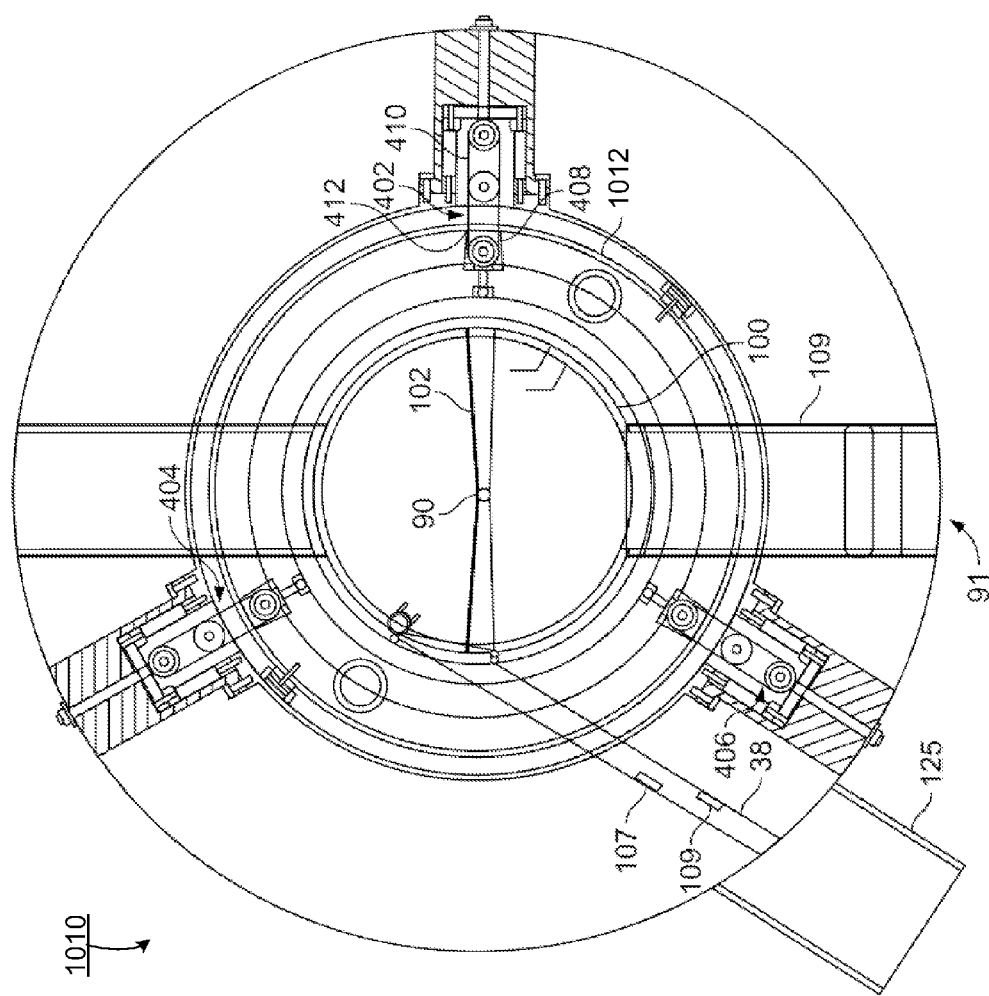
Figure 7:
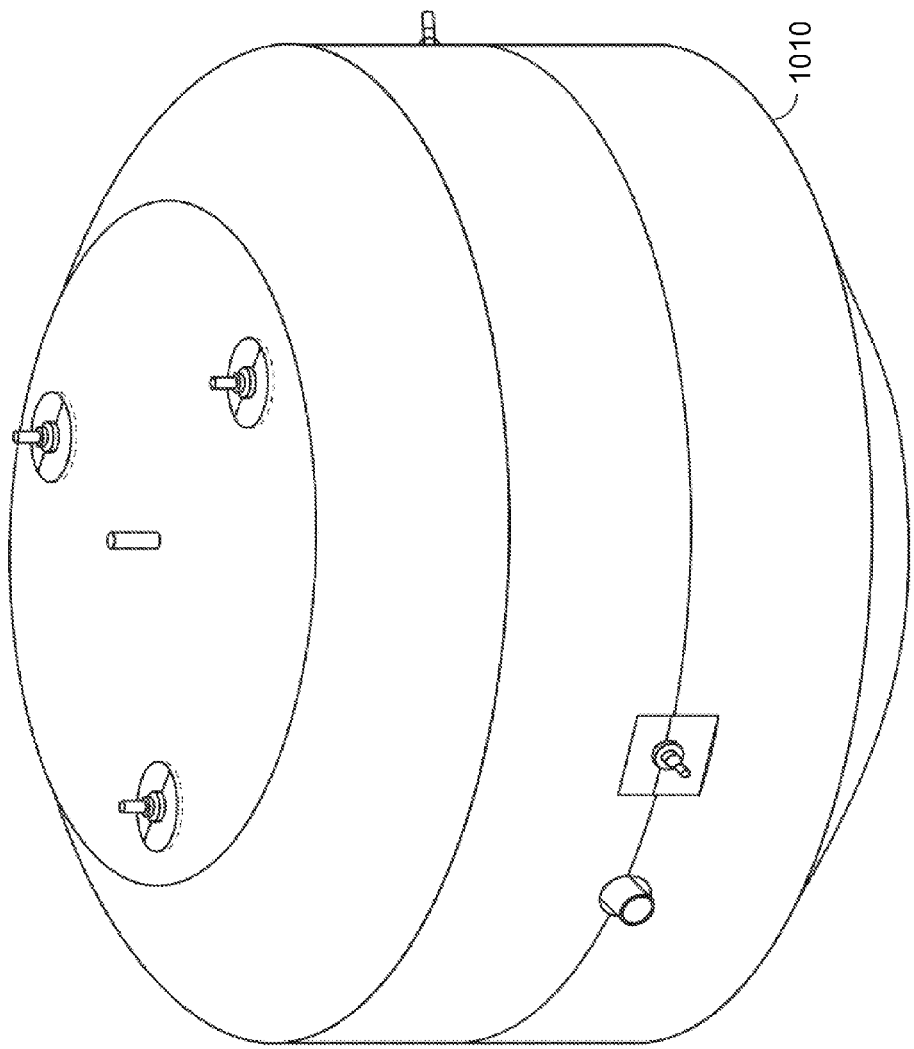
FIG. 7 is a perspective view of a synchrocyclotron.

The geometry of the coil sets is maintained by mounting the coil sets in the reverse rectangular bobbin 56 to exert a restorative force 60 that works against the distorting force produced when the coils are energized. As shown in FIG. 6, the position of the coil sets is maintained relative to the magnet yoke and cryostat using a set of warm-to-cold support straps 402, 404, 406. Supporting the cold mass with thin straps reduces the heat leakage imparted to the cold mass by the rigid support system. The straps are arranged to withstand the varying gravitational force on the coil sets as the magnet rotates on board the gantry. They withstand the combined effects of gravity and the large de-centering force realized by the coil sets when it is perturbed from a perfectly symmetric position relative to the magnet yoke. Additionally the links act to reduce dynamic forces imparted on the coil sets as the gantry accelerates and decelerates when its position is changed. Each warm-to-cold support includes one S2 fiberglass link and one carbon fiber link. The carbon fiber link is supported across pins between the warm yoke and an intermediate temperature (50-70 K), and the S2 fiberglass link 408 is supported across the intermediate temperature pin and a pin attached to the cold mass. Each link is 5 cm long (pin center to pin center) and is 17 mm wide. The link thickness is 9 mm. Each pin is made of high strength stainless steel and is 40 mm in diameter.

The main superconducting coils are maintained at temperatures near absolute zero (e.g., about 4 degrees Kelvin) by enclosing the coil assembly (the coils and the support structure) inside an evacuated annular aluminum or stainless steel cryostatic chamber that provides at least some free space around the coil structure. In some implementations, the temperature near absolute zero is achieved and maintained using a cooling channel (not shown) containing liquid helium, which is formed inside the support structure, and which contains a thermal connection between the liquid helium in the channel and the corresponding superconducting coil. An example of a liquid helium cooling system of the type described above, and that may be used is described in U.S. patent application Ser. No. 13/148,000 (Begg et al.).

As an example, the coil sets are maintained at temperatures near absolute zero (e.g., about 4 degrees Kelvin) by enclosing the coil assembly (the coils and the bobbin) inside an evacuated annular aluminum or stainless steel cryostatic chamber 70 that provides a free space around the coil structure, except at a limited set of support points 71, 73.

In some implementations, the temperature near absolute zero is achieved and maintained using one single-stage Gifford-McMahon cryo-cooler and three two-stage Gifford McMahon cryo-coolers. Each two stage cryo-cooler has a second stage cold end attached to a condenser that recondenses Helium vapor into liquid Helium. The cryo-cooler heads are supplied with compressed Helium from a compressor. The single-stage Gifford-McMahon cryo-cooler is arranged to cool high temperature (e.g., 50-70 degrees Kelvin) leads that supply current to the superconducting windings.

In some implementations, the temperature near absolute zero is achieved and maintained using two Gifford-McMahon cryo-coolers 72, 74 that are arranged at different positions on the coil assembly. Each cryo-cooler has a cold end 76 in contact with the coil assembly. The cryo-cooler heads 78 are supplied with compressed Helium from a compressor 80. Two other Gifford-McMahon cryo-coolers 77, 79 are arranged to cool high temperature (e.g., 60-80 degrees Kelvin) leads that supply current to the superconducting windings.

The coil assembly and cryostatic chamber are mounted within and fully enclosed by two halves 81, 83 of a pillbox-shaped magnet yoke 82. In this example, the inner diameter of the coil assembly is about 74.6 cm. The iron yoke 82 provides a path for the return magnetic field flux 84 and magnetically shields the volume 86 between the pole faces 44, 46 to prevent external magnetic influences from perturbing the shape of the magnetic field within that volume. The yoke also serves to decrease the stray magnetic field in the vicinity of the accelerator.

Although two coil sets are shown, the accelerator can alternatively include one coil set or more than two coil sets. In the situation where only one coil set is used, the coil set is configured to receive a variable electrical current to vary the magnetic field. In the situations where more than two coil sets are used, one or more of the coil sets is configured to receive a variable electrical current to vary the magnetic field.

Figure 9:
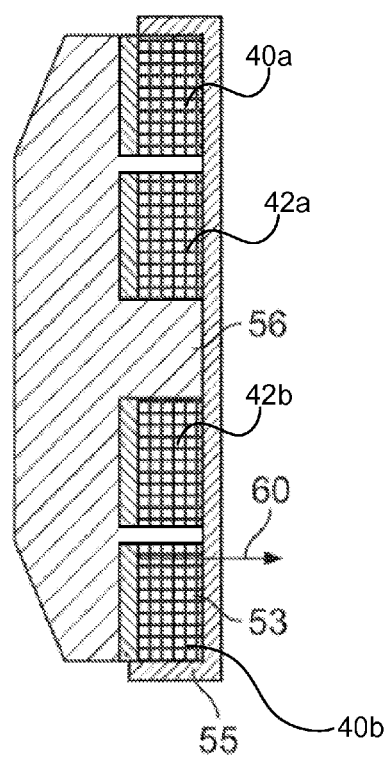
FIG. 9 is a cross-sectional view of a portion of a reverse bobbin and windings.
Figure 10:
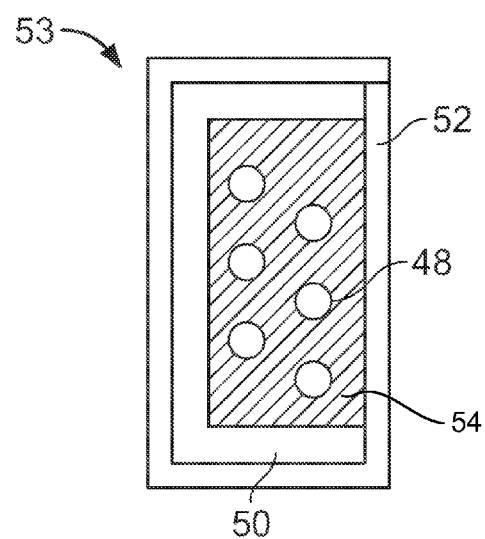
FIG. 10 is a cross sectional view of a cable-in-channel composite conductor.

One, two, or more sets of coils can be constructed similarly to the constructions shown in FIGS. 9 and 10. Although the two sets of coils are described to have the same radius and construction (e.g., number of layers and turns, materials, etc.), they can have different features. In some implementations, the different sets of coils are constructed based on the need for receiving different electrical current.

In addition to being variable, the magnetic field in the accelerator needs to have certain properties to maintain the particle beam within the chamber as it accelerates. The magnetic field index n, which is shown below, $$n=-(r/B)dB/dr,$$

should be kept positive to maintain this "weak" focusing. Here r is the radius of the beam and B is the magnetic field. Additionally the field index needs to be maintained below 0.2, because at this value the periodicity of radial oscillations and vertical oscillations of the beam coincide in a $v_r=2 v_z$ resonance. The betatron frequencies are defined by $c_r=(1-n)1/2$ and $v_z=n1/2$. The poles are ferromagnetic and ferromagnetic pole faces are designed to shape the magnetic field generated by the coils so that the field index n is maintained positive and less than 0.2 in the smallest diameter consistent with a 250 MeV beam in the given magnetic field.

The weak focusing of the magnetic field index can facilitate the variation of the particle beam energy based on the variation of the magnetic field. As the magnetic field is changed, continuously or in steps, by changing the total electrical current applied to the coil sets, the axial focusing of the magnetic field is changed accordingly. In some implementations, steering magnets (not shown) can be used to direct the magnetic field to correct any possible pointing errors caused by the variation of the field.

Stray magnetic fields exiting from the accelerator are limited by both the magnet yoke 46a, 46b (which also serves as a shield) and additional separate magnetic shield (not shown).

In some implementations, the return yoke and shield may be replaced by, or augmented by, an active return system. An example active return system includes one or more active return coils that conduct current in a direction opposite to current through the main superconducting coils. In some example implementations, there is an active return coil for each superconducting coil, e.g., two active return coils—one for each superconducting coil (referred to as a "main" coil). Each active return coil may also be a superconducting coil that surrounds the outside of a corresponding main superconducting coil.

Current passes through the active return coils in a direction that is opposite to the direction of current passing through the main coils. The current passing through the active return coils thus generates a magnetic field that is opposite in polarity to the magnetic field generated by the main coils. As a result, the magnetic field generated by an active return coil is able to dissipate at least some of the relatively strong stray magnetic field resulting from the corresponding main coil. In some implementations, each active return may be used to generate a magnetic field of between 2.5 T and 12 T or more. An example of an active return system that may be used is described in U.S. patent application Ser. No. 13/907,601, filed on May 31, 2013, the contents of which are incorporated herein by reference.

Figure 4:
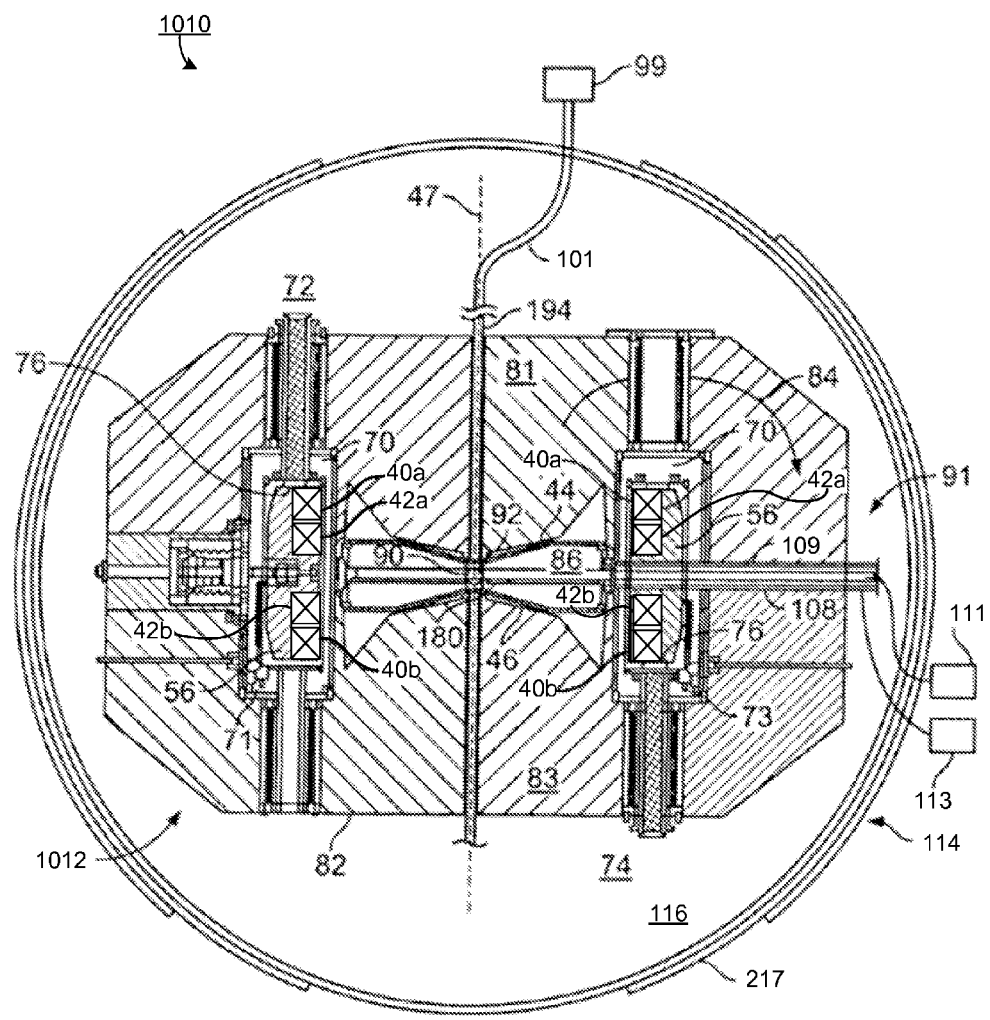
FIGS. 4, 5, and 6 are cross-sectional views of a synchrocyclotron.
Figure 5:
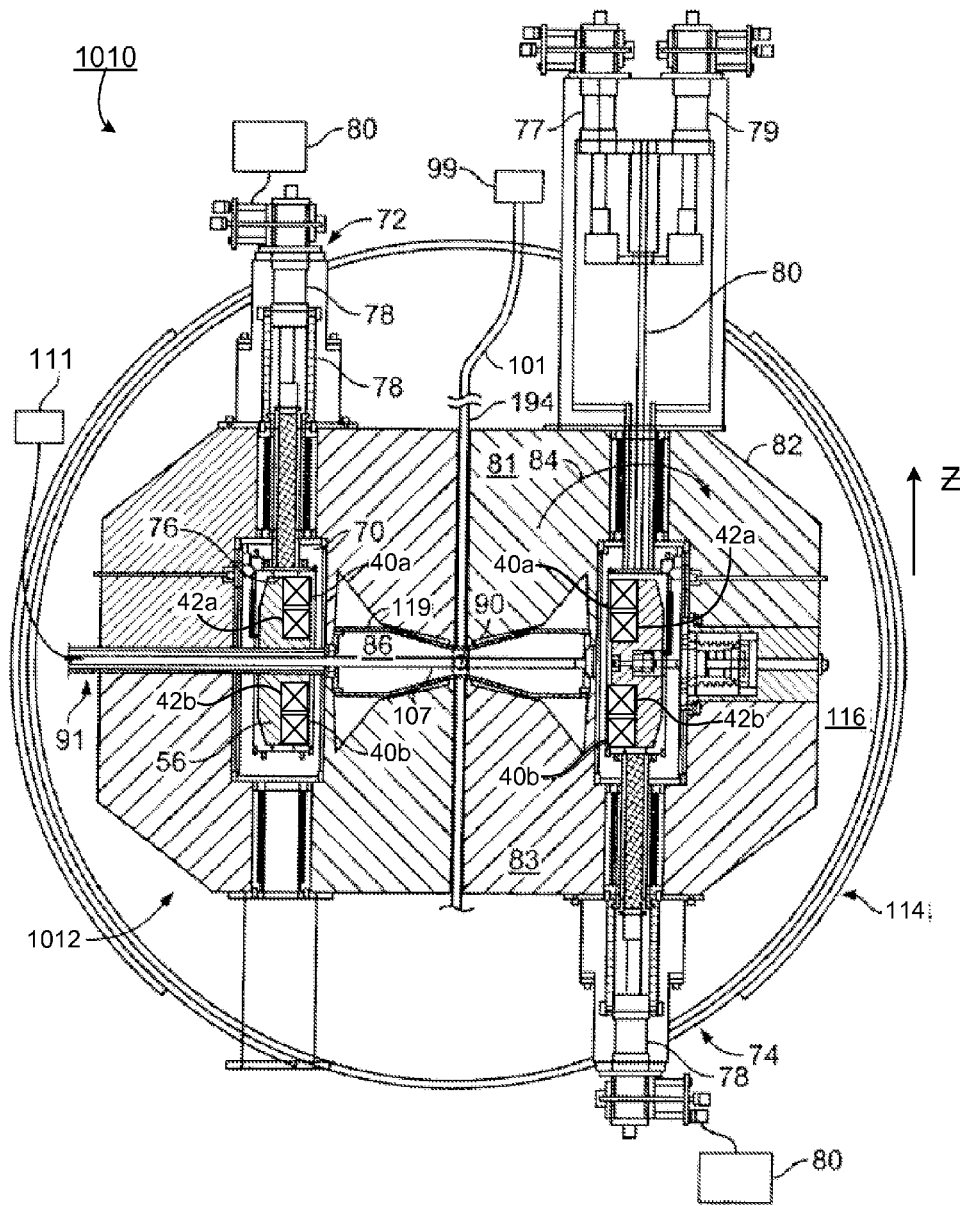

As shown in FIGS. 4 and 11, the synchrocyclotron includes a particle source 90 of a Penning ion gauge geometry located near the geometric center 92 of the magnet structure 82. The particle source may be as described below, or the particle source may be of the type described in U.S. patent application Ser. No. 11/948,662 incorporated herein by reference.

Particle source 90 is fed from a supply 99 of hydrogen through a gas line 101 and tube 194 that delivers gaseous hydrogen. Electric cables 94 carry an electric current from a current source 95 to stimulate electron discharge from cathodes 192, 190 that are aligned with the magnetic field 200.

In this example, the discharged electrons ionize the gas exiting through a small hole from tube 194 to create a supply of positive ions (protons) for acceleration by one semicircular (dee-shaped) radio-frequency plate 100 that spans half of the space enclosed by the magnet structure and one dummy dee plate 102. In the case of an interrupted particle source (an example of which is described in U.S. patent application Ser. No. 11/948,662), all (or a substantial part) of the tube containing plasma is removed at the acceleration region, thereby allowing ions to be more rapidly accelerated in a relatively high magnetic field.

RF Frequency Ranges

As shown in FIG. 12, the dee plate 100 is a hollow metal structure that has two semicircular surfaces 103, 105 that enclose a space 107 in which the protons are accelerated during half of their rotation around the space enclosed by the magnet structure. A duct 109 opening into the space 107 extends through the yoke to an external location from which a vacuum pump 111 can be attached to evacuate the space 107 and the rest of the space within a vacuum chamber 119 in which the acceleration takes place. The dummy dee 102 comprises a rectangular metal ring that is spaced near to the exposed rim of the dee plate. The dummy dee is grounded to the vacuum chamber and magnet yoke. The dee plate 100 is driven by a radio-frequency signal that is applied at the end of a radio-frequency transmission line to impart an electric field in the space 107. The radio frequency electric field is made to vary in time as the accelerated particle beam increases in distance from the geometric center. Examples of radio frequency waveform generators that are useful for this purpose are described in U.S. patent application Ser. No. 11/187,633, titled "A Programmable Radio Frequency Waveform Generator for a Synchrocyclotron," filed Jul. 21, 2005, and in U.S. Provisional Application No. 60/590,089, same title, filed on Jul. 21, 2004, both of which are incorporated herein by reference. The radio frequency electric field may be controlled in the manner described in U.S. patent application Ser. No. 11/948,359, entitled "Matching A Resonant Frequency Of A Resonant Cavity To A Frequency Of An Input Voltage", the contents of which are incorporated herein by reference.

For the beam emerging from the centrally located particle source to clear the particle source structure as it begins to spiral outward, a large voltage difference is required across the radio frequency plates. In some versions from 5,000 to 20,000 Volts may be applied across the radio frequency plates. To reduce the power required to drive this large voltage, the magnet structure is arranged to reduce the capacitance between the radio frequency plates and ground. This is done by creating sufficient clearance from the radio frequency structures through the outer yoke and the cryostat housing and making sufficient space between the magnet pole faces.

The high voltage alternating potential that drives the dee plate has a frequency that is swept downward during the accelerating cycle to account for the increasing relativistic mass of the protons and the decreasing magnetic field. The voltage can sweep over a frequency range in cycles, and each cycle can correspond to the acceleration cycle of the particles in the accelerator. In some implementations, the accelerator is a synchrocyclotron and the particle beams output from the accelerator are in the form of pulsed particle bunches. Each particle bunch can be accelerated within an acceleration cycle and the RF sweeping cycle can be the same as the cycle the particle bunches are produced or extracted.

The dummy dee does not require a hollow semi-cylindrical structure as it is at ground potential along with the vacuum chamber walls. Other plate arrangements could be used such as more than one pair of accelerating electrodes driven with different electrical phases or multiples of the fundamental frequency. The RF structure can be tuned to keep the correct resonant match during the required frequency sweep by using, for example, a rotating capacitor having intermeshing rotating and stationary blades. During each meshing of the blades, the capacitance increases, thus lowering the resonant frequency of the RF structure. The blades can be shaped to create a precise frequency sweep required. One bunch of particles is accelerated during each meshing of the blades of the rotating condenser.

The RF frequency range over which the high voltage on the dee plate 100 sweeps is related to the beam energy and different beam energies correspond to different RF ranges. Accordingly, as the beam energy varies in the accelerator, the corresponding RF range over which the voltage sweeps in cycles is changed. Different RF frequency ranges can be selected based on the beam energy ranges. In some implementations, to accommodate the ranges of the energy variation, the RF frequency range has a lower boundary that varies between about 40 MHz and about 250 MHz and an upper boundary that varies between about 56 MHz and about 340 MHz. For example, the lower boundary can vary between about 73 MHz to about 150 MHz and the upper boundary can vary between about 131 MHz and about 196 MHz. In the example shown in table 1, RF frequency range is 99 MHz to 132 MHz for a beam energy of 250 MeV, 97 MHz to 128 MHz for a beam energy of 235 MeV, and 93 MHz to 120 MHz for a beam energy of 211 MeV.

Figure 13:
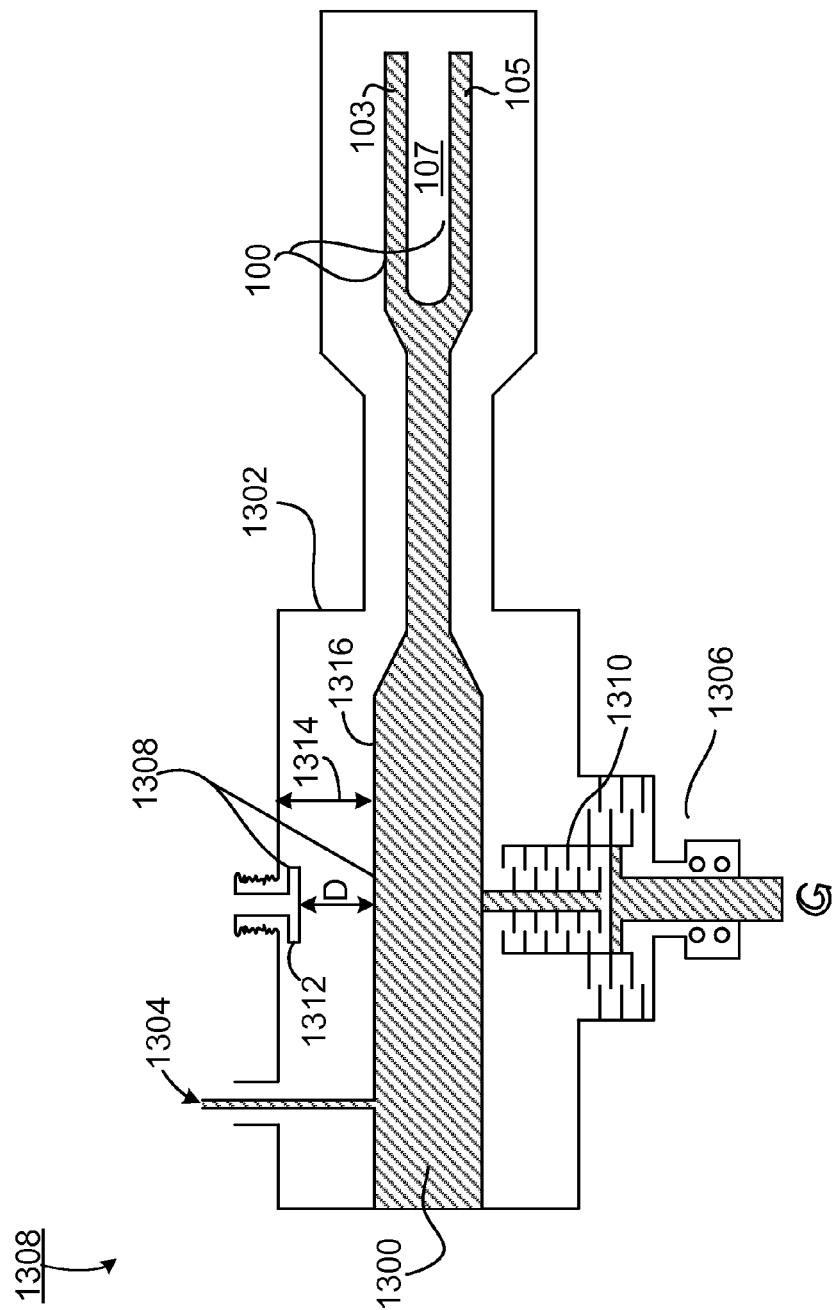
FIG. 13 is a cross-sectional view of an example of a radio frequency (RF) structure.

FIG. 13 shows an example RF structure for sweeping the voltage on the dee plate 100 over an RF frequency range for each energy level of the particle beam, and for varying the frequency range when the particle beam energy is varied. The semicircular surfaces 103, 105 of the dee plate 100 are connected to an inner conductor 1300 and housed in an outer conductor 1302. The high voltage is applied to the dee plate 100 from a power source (not shown, e.g., an oscillating voltage input) through a power coupling device 1304 that couples the power source to the inner conductor. In some implementations, the coupling device 1304 is positioned on the inner conductor 1300 to provide power transfer from the power source to the dee plate 100. In addition, the dee plate 100 is coupled to variable reactive elements 1306, 1308 to perform the RF frequency sweep for each particle energy level, and to change the RF frequency range for different particle energy levels.

In particular, the variable reactive element 1306 can be a rotating capacitor that has multiple blades 1310 rotatable by a motor (not shown). By meshing or unmeshing the blades 1310 during each cycle of RF sweeping, the capacitance of the RF structure changes, which in turn changes the resonant frequency of the RF structure. In some implementations, during each quarter cycle of the motor, the blades 1310 mesh with the each other. The capacitance of the RF structure increases and the resonant frequency decreases. The process reverses as the blades 1310 unmesh. As a result, the power required to generate the high voltage applied to the dee plate 103 and necessary to accelerate the beam can be reduced by a large factor. In some implementations, the shape of the blades 1310 is machined to form the required dependence of resonant frequency on time.

The blade rotation can be synchronized with the RF frequency generation. By varying the Q-factor of the RF cavity, the resonant frequency of the RF structure is kept close to the frequency of the alternating voltage potential applied to the dee plate 103 (the dummy dee is grounded and is not shown in FIG. 13).

The variable reactive element 1308 can be a capacitor formed by a plate 1312 and a surface 1316 of the inner conductor 1300. The plate 1312 is movable along a direction 1314 towards or away from the surface 1316. The capacitance of the capacitor changes as the distance D between the plate 1312 and the surface 1316 changes. For each frequency range to be swept for one particle energy, the distance D is at a set value, and to change the frequency range, the plate 1312 is moved corresponding to the change in the energy of the output beam.

In some implementations, the inner and outer conductors 1300, 1302 are formed of a metallic material, such as copper, aluminum, or silver. The blades 1310 and the plate 1312 can also be formed of the same or different metallic materials as the conductors 1300, 1302. The coupling device 1304 can be an electrical conductor. The variable reactive elements 1306, 1308 can have other forms and can couple to the dee plate 100 in other ways to perform the RF frequency sweep and the frequency range alteration. In some implementations, a single variable reactive element can be configured to perform the functions of both the variable reactive elements 1306, 1308. In other implementations, more than two variable reactive elements can be used.

Beam Acceleration and Extraction

The vacuum chamber 119 in which the acceleration occurs is a generally cylindrical container. The vacuum chamber encloses the RF plates and the particle source and is evacuated by the vacuum pump 111. Maintaining a high vacuum ensures that accelerating ions are not lost to collisions with gas molecules and enables the RF voltage to be kept at a higher level without arcing.

Protons traverse a generally spiral orbital path beginning at the particle source. In half of each loop of the spiral path, the protons gain energy as they pass through the RF electric field in space 107. As the ions gain energy, the radius of the central orbit of each successive loop of their spiral path is larger than the prior loop until the loop radius reaches the maximum radius of the pole face. At that location a magnetic and electric field perturbation directs ions into an area where the magnetic field rapidly decreases, and the ions depart the area of the high magnetic field and are directed through an evacuated tube 38, referred to herein as the extraction channel, to exit the yoke of the cyclotron. A magnetic regenerator may be used to change the magnetic field perturbation to direct the ions. The ions exiting the cyclotron will tend to disperse as they enter the area of markedly decreased magnetic field that exists in the room around the cyclotron. Beam shaping elements 107, 109 in the extraction channel 38 redirect the ions so that they stay in a straight beam of limited spatial extent.

As the beam exits the extraction channel it is passed through a beam formation system 125 (FIG. 6) that can be programmably controlled to create a desired combination of scattering angle and range modulation for the beam. Examples of beam forming systems useful for that purpose are described in U.S. patent application Ser. No. 10/949,734, titled "A Programmable Particle Scatterer for Radiation Therapy Beam Formation", filed Sep. 24, 2004, and U.S. Provisional Application No. 60/590,088, filed Jul. 21, 2005, both of which are incorporated herein by reference. Beam formation system 125 may be used in conjunction with an inner gantry 601, which is described below, to direct a beam to the patient. The beam formation system 125 can also be a scanning system.

During operation, the dee plates absorb energy from the applied radio frequency field as a result of conductive resistance along the surfaces of the plates. This energy appears as heat and is removed from the plates using water cooling lines 108 that release the heat in a heat exchanger 113 (FIG. 4).

Stray magnetic fields exiting from the cyclotron are limited by both the pillbox magnet yoke (which also serves as a shield) and a separate magnetic shield 114. The separate magnetic shield includes of a layer 117 of ferromagnetic material (e.g., steel or iron) that encloses the pillbox yoke, separated by a space 116. This configuration that includes a sandwich of a yoke, a space, and a shield achieves adequate shielding for a given leakage magnetic field at lower weight.

As mentioned, the gantry allows the synchrocyclotron to be rotated about the horizontal rotational axis 532. The truss structure 516 has two generally parallel spans 580, 582. The synchrocyclotron is cradled between the spans about midway between the legs. The gantry is balanced for rotation about the bearings using counterweights 122, 124 mounted on ends of the legs opposite the truss.

The gantry is driven to rotate by an electric motor mounted to one or both of the gantry legs and connected to the bearing housings by drive gears. The rotational position of the gantry is derived from signals provided by shaft angle encoders incorporated into the gantry drive motors and the drive gears.

At the location at which the ion beam exits the cyclotron, the beam formation system 125 acts on the ion beam to give it properties suitable for patient treatment. For example, the beam may be spread and its depth of penetration varied to provide uniform radiation across a given target volume. The beam formation system can include passive scattering elements as well as active scanning elements.

Figure 14:
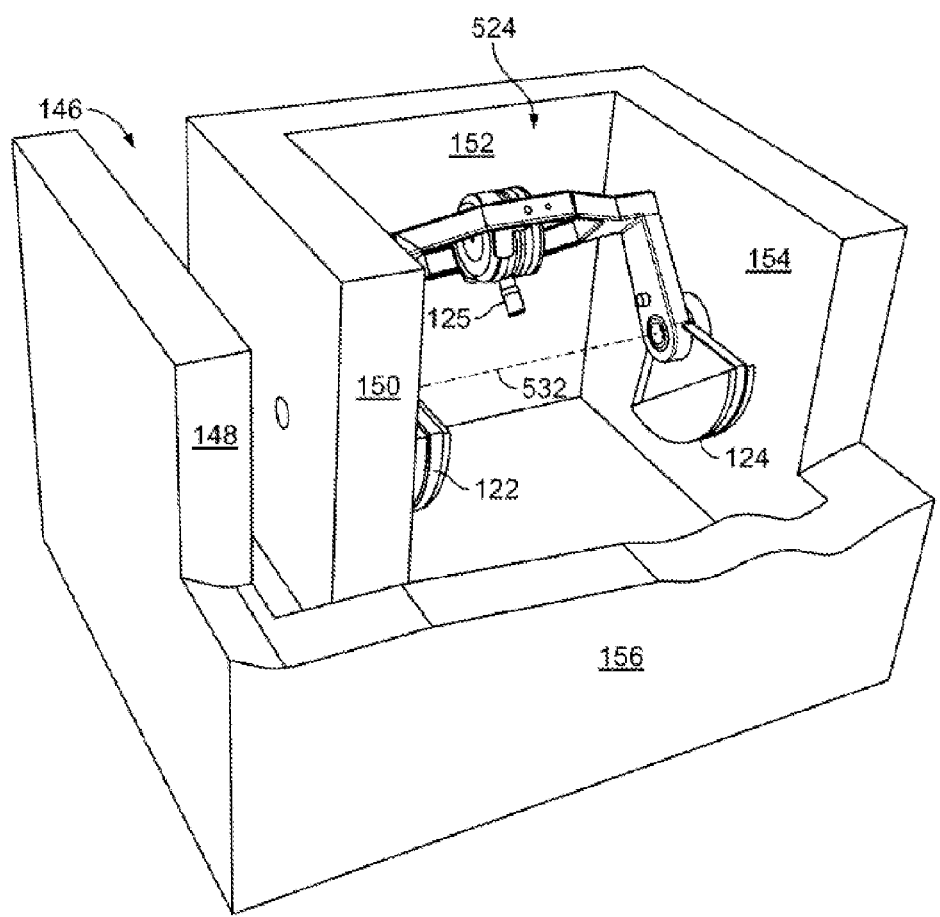
FIG. 14 is a perspective view of a vault.
Figure 15:
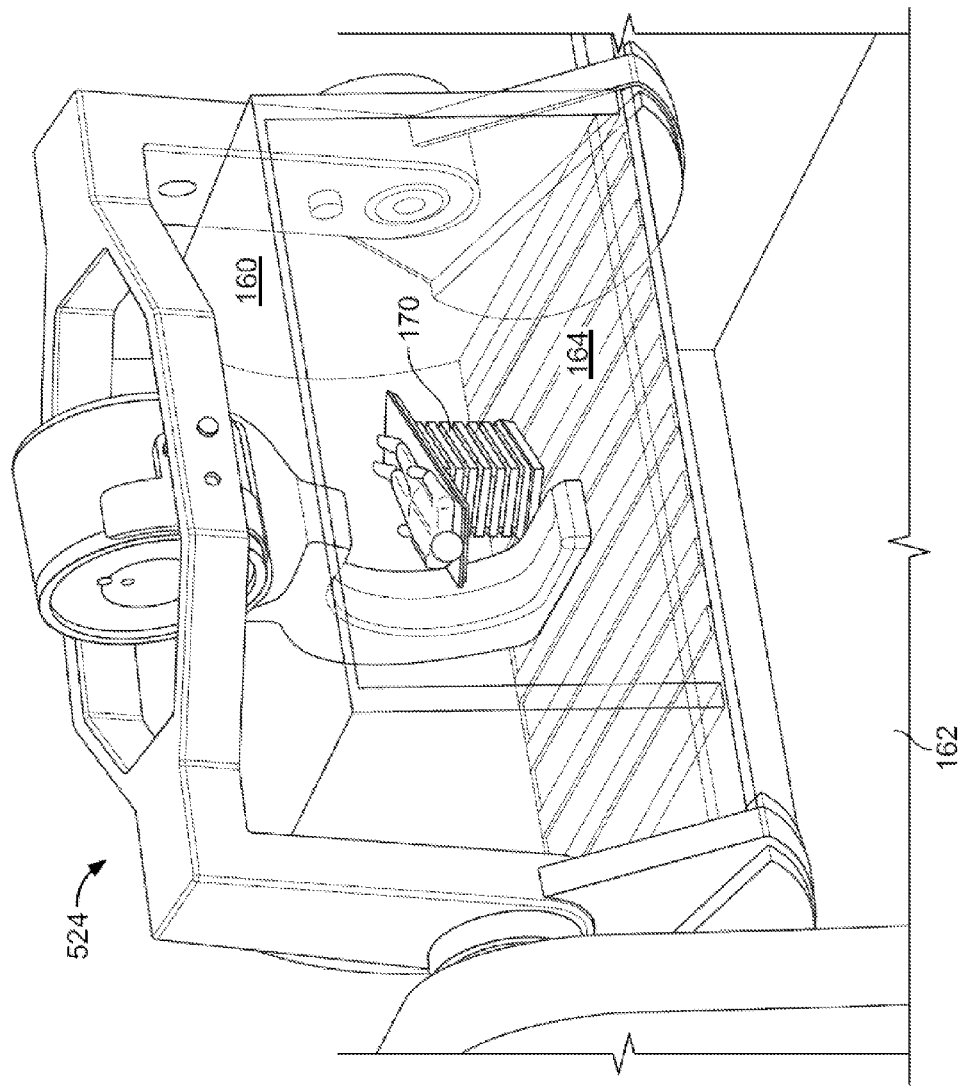
FIG. 15 is a perspective view of a treatment room with a vault.

As shown in FIGS. 2, 14, and 15, the gantry bearings are supported by the walls of a cyclotron vault 524. The gantry enables the cyclotron to be swung through a range 520 of 180 degrees (or more) including positions above, to the side of, and below the patient. The vault is tall enough to clear the gantry at the top and bottom extremes of its motion. A maze 146 sided by walls 148, 150 provides an entry and exit route for therapists and patients. Because at least one wall 152 is never in line with the proton beam directly from the cyclotron, it can be made relatively thin and still perform its shielding function. The other three side walls 154, 156, 150/148 of the room, which may need to be more heavily shielded, can be buried within an earthen hill (not shown). The required thickness of walls 154, 156, and 158 can be reduced, because the earth can itself provide some of the needed shielding.

Figure 16:
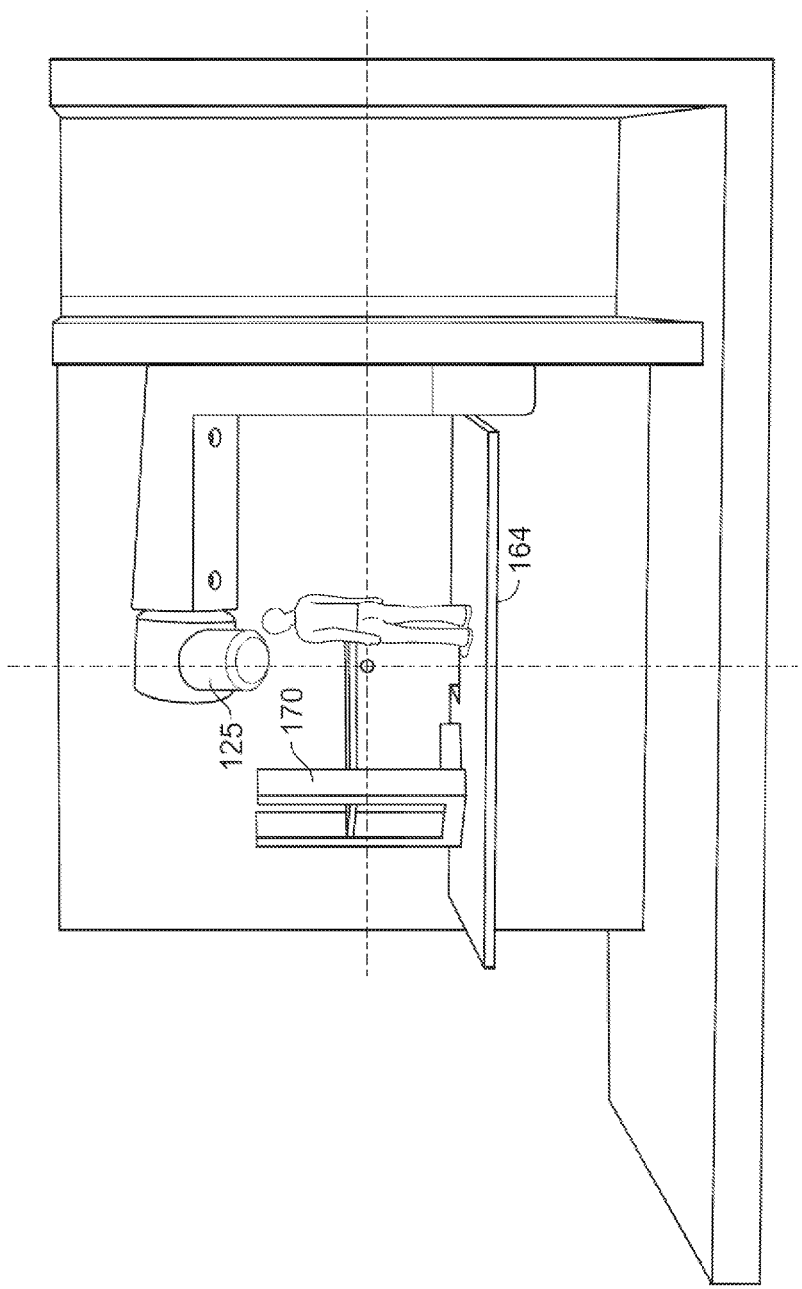
FIG. 16 shows a profile of one-half of a symmetrical profile of a pole face and a pole piece.

Referring to FIGS. 15 and 16, for safety and aesthetic reasons, a therapy room 160 may be constructed within the vault. The therapy room is cantilevered from walls 154, 156, 150 and the base 162 of the containing room into the space between the gantry legs in a manner that clears the swinging gantry and also maximizes the extent of the floor space 164 of the therapy room. Periodic servicing of the accelerator can be accomplished in the space below the raised floor. When the accelerator is rotated to the down position on the gantry, full access to the accelerator is possible in a space separate from the treatment area. Power supplies, cooling equipment, vacuum pumps and other support equipment can be located under the raised floor in this separate space. Within the treatment room, the patient support 170 can be mounted in a variety of ways that permit the support to be raised and lowered and the patient to be rotated and moved to a variety of positions and orientations.

In system 602 of FIG. 17, a beam-producing particle accelerator, in this case synchrocyclotron 604, is mounted on rotating gantry 605. Rotating gantry 605 is of the type described herein, and can angularly rotate around patient support 606. This feature enables synchrocyclotron 604 to provide a particle beam directly to the patient from various angles. For example, as in FIG. 17, if synchrocyclotron 604 is above patient support 606, the particle beam may be directed downwards toward the patient. Alternatively, if synchrocyclotron 604 is below patient support 606, the particle beam may be directed upwards toward the patient. The particle beam is applied directly to the patient in the sense that an intermediary beam routing mechanism is not required. A routing mechanism, in this context, is different from a shaping or sizing mechanism in that a shaping or sizing mechanism does not re-route the beam, but rather sizes and/or shapes the beam while maintaining the same general trajectory of the beam.

All of the active systems of the accelerator, such as a synchrocyclotron (the current driven superconducting coils, the RF-driven plates, the vacuum pumps for the vacuum acceleration chamber and for the superconducting coil cooling chamber, the current driven particle source, the hydrogen gas source, and the RF plate coolers, for example), are controlled by appropriate control electronics (not shown), which may include, e.g., one or more computers programmed with appropriate programs to effect control.

The control of the gantry, the patient support, the active beam shaping elements, and the accelerator to perform a therapy session is achieved by appropriate therapy control electronics (not shown).

The radiation therapy system described in this example is used for proton radiation therapy, but the same principles and details can be applied in analogous systems for use in heavy ion (ion) treatment systems.

The particle source may be of the type described in U.S. patent application Ser. No. 11/948,662 incorporated herein by reference. Examples of radio frequency waveform generators that are useful for this purpose are described in U.S. patent application Ser. No. 11/187,633, titled "A Programmable Radio Frequency Waveform Generator for a Synchrocyclotron," filed Jul. 21, 2005, and in U.S. Provisional Application No. 60/590,089, same title, filed on Jul. 21, 2004, both of which are incorporated herein by reference. The radio frequency electric field may be controlled in the manner described in U.S. patent application Ser. No. 11/948,359, entitled "Matching A Resonant Frequency Of A Resonant Cavity To A Frequency Of An Input Voltage", the contents of which are incorporated herein by reference.

Further details regarding the foregoing system may be found in U.S. Pat. No. 7,728,311, filed on Nov. 16, 2006 and entitled "Charged Particle Radiation Therapy", and in U.S. patent application Ser. No. 12/275,103, filed on Nov. 20, 2008 and entitled "Inner Gantry". The contents of U.S. Pat. No. 7,728,311 and in U.S. patent application Ser. No. 12/275,103 are hereby incorporated by reference into this disclosure.

Any two more of the foregoing implementations may be used in an appropriate combination in an appropriate particle accelerator (e.g., a synchrocyclotron). Likewise, individual features of any two more of the foregoing implementations may be used in an appropriate combination. The subsections and their respective titles are used to facilitate reading and understanding of the description. The titles of the subsections do not cover or limit the interpretation of the content of the respective subsections. The content of the subsections are not separate or independent from each other. Instead, any appropriate combinations of features from different subsections can be made.

Elements of different implementations described herein may be combined to form other implementations not specifically set forth above. Elements may be left out of the processes, systems, apparatus, etc., described herein without adversely affecting their operation. Various separate elements may be combined into one or more individual elements to perform the functions described herein.

The example implementations described herein are not limited to use with a particle therapy system or to use with the example particle therapy systems described herein. Rather, the example implementations can be used in any appropriate system that directs accelerated particles to an output.

Additional information concerning the design of the particle accelerator described herein can be found in U.S. Provisional Application No. 60/760,788, entitled "High-Field Superconducting Synchrocyclotron" and filed Jan. 20, 2006; U.S. patent application Ser. No. 11/463,402, entitled "Magnet Structure For Particle Acceleration" and filed Aug. 9, 2006; and U.S. Provisional Application No. 60/850,565, entitled "Cryogenic Vacuum Break Pneumatic Thermal Coupler" and filed Oct. 10, 2006, all of which are incorporated herein by reference as if set forth in full.

The following applications, which were filed on Sep. 28, 2012, are incorporated by reference into the subject application as if set forth herein in full: the U.S. Provisional Application entitled "CONTROLLING INTENSITY OF A PARTICLE BEAM" (Application No. 61/707,466), the U.S. Provisional Application entitled "ADJUSTING ENERGY OF A PARTICLE BEAM" (Application No. 61/707,515), the U.S. Provisional Application entitled "ADJUSTING COIL POSITION" (Application No. 61/707,548), the U.S. Provisional Application entitled "FOCUSING A PARTICLE BEAM USING MAGNETIC FIELD FLUTTER" (Application No. 61/707,572), the U.S. Provisional Application entitled "MAGNETIC FIELD REGENERATOR" (Application No. 61/707,590), the U.S. Provisional Application entitled "FOCUSING A PARTICLE BEAM" (Application No. 61/707,704), the U.S. Provisional Application entitled "CONTROLLING PARTICLE THERAPY (Application No. 61/707,624), and the U.S. Provisional Application entitled "CONTROL SYSTEM FOR A PARTICLE ACCELERATOR" (Application No. 61/707,645).

The following are also incorporated by reference into the subject application as if set forth herein in full: U.S. Pat. No. 7,728,311 which issued on Jun. 1, 2010, U.S. patent application Ser. No. 11/948,359 which was filed on Nov. 30, 2007, U.S. patent application Ser. No. 12/275,103 which was filed on Nov. 20, 2008, U.S. patent application Ser. No. 11/948,662 which was filed on Nov. 30, 2007, U.S. Provisional Application No. 60/991,454 which was filed on Nov.

30, 2007, U.S. Pat. No. 8,003,964 which issued on Aug. 23, 2011, U.S. Pat. No. 7,208,748 which issued on Apr. 24, 2007, U.S. Pat. No. 7,402,963 which issued on Jul. 22, 2008, and U.S. patent application Ser. No. 11/937,573 filed on Nov. 9, 2007.

Any features of the subject application may be combined with one or more appropriate features of the following: the U.S. Provisional Application entitled "CONTROLLING INTENSITY OF A PARTICLE BEAM" (Application No. 61/707,466), the U.S. Provisional Application entitled "ADJUSTING ENERGY OF A PARTICLE BEAM" (Application No. 61/707,515), the U.S. Provisional Application entitled "ADJUSTING COIL POSITION" (Application No. 61/707,548), the U.S. Provisional Application entitled "FOCUSING A PARTICLE BEAM USING MAGNETIC FIELD FLUTTER" (Application No. 61/707,572), the U.S. Provisional Application entitled "MAGNETIC FIELD REGENERATOR" (Application No. 61/707,590), the U.S. Provisional Application entitled "FOCUSING A PARTICLE BEAM" (Application No. 61/707,704), the U.S. Provisional Application entitled "CONTROLLING PARTICLE THERAPY (Application No. 61/707,624), and the U.S. Provisional Application entitled "CONTROL SYSTEM FOR A PARTICLE ACCELERATOR" (Application No. 61/707,645), U.S. Pat. No. 7,728,311 which issued on Jun. 1, 2010, U.S. patent application Ser. No. 11/948,359 which was filed on Nov. 30, 2007, U.S. patent application Ser. No. 12/275,103 which was filed on Nov. 20, 2008, U.S. patent application Ser. No. 11/948,662 which was filed on Nov. 30, 2007, U.S. Provisional Application No. 60/991,454 which was filed on Nov. 30, 2007, U.S. Pat. No. 8,003,964 which issued on Aug. 23, 2011, U.S. Pat. No. 7,208,748 which issued on Apr. 24, 2007, U.S. Pat. No. 7,402,963 which issued on Jul. 22, 2008, U.S. patent application Ser. No. 13/148,000 filed Feb. 9, 2010, and U.S. patent application Ser. No. 11/937,573 filed on Nov. 9, 2007.

Other implementations not specifically described herein are also within the scope of the following claims.

What is claimed is:

1. A synchrocyclotron comprising:
a voltage source to provide a radio frequency (RF) voltage to a cavity to accelerate particles from a particle source;
one or more coils to pass electrical current having one of multiple values and to generate a magnetic field in the cavity corresponding to the electrical current, the magnetic field for causing the particles to move orbitally within the cavity at an energy that corresponds to the electrical current, the magnetic field being at least 4 Tesla;
magnetic pole pieces at least partly defining the cavity, the magnetic pole pieces comprising ferromagnetic material; and
an extraction channel to receive the particles from the cavity and to output the particles, the particles that are output having an energy that corresponds to the electrical current;
wherein the synchrocyclotron is configured to enable setting of the electrical current to one of the multiple values, each of the multiple values corresponding to a different energy at which particles are output from the cavity;
wherein the energy of the particles that are output from the cavity is in a range that is between about 100 MeV and about 300 MeV; and
wherein the voltage source is configured to sweep the RF voltage over different frequency ranges, each different frequency range corresponding to a different energy at which particles are output from the cavity.

2. The synchrocyclotron of claim 1, wherein the electrical current comprises a first portion that is fixed and a second portion that is changeable to take on one of multiple values, the second portion of the electrical current being within a range to cause the magnetic field at an extraction radius of the synchrocyclotron to be between about 5% and 35% of a maximum value of the magnetic field.

3. The synchrocyclotron of claim 2, wherein the magnetic field at the extraction radius is changeable by between about 0.2 Tesla and about 1.4 Tesla.

4. The synchrocyclotron of claim 2, wherein the magnetic field at the extraction radius is changeable by between about 0.6 and about 4.2 Tesla.

5. The synchrocyclotron of claim 1, wherein the one or more coils comprises a first set of coils and a second set of coils, the first set being configured to receive a fixed portion of the electrical current, and the second set being configured to receive a portion of the electrical current that is changeable to take on one of multiple values.

6. The synchrocyclotron of claim 5, wherein the portion of the electrical current that is changeable to take on one of multiple values is within a range that causes the magnetic field at an extraction radius of the synchrocyclotron to change by about 5% and 35% of a maximum value of the magnetic field.

7. The synchrocyclotron of claim 6, wherein the magnetic field at the extraction radius is changeable by between about 0.2 Tesla and about 1.4 Tesla or between about 0.6 and about 4.2 Tesla.

8. The synchrocyclotron of claim 5, wherein the magnetic field has a magnitude having a range of about 4 Tesla to about 20 Tesla.

9. The synchrocyclotron of claim 1, wherein the one or more coils comprises one or more sets of coils, and wherein at least one set of coils is superconducting and comprises between 2 million ampere turns and 10 million ampere turns.

10. The synchrocyclotron of claim 1, wherein the energy of the particles that are output from the cavity is variable continuously between about 115 MeV and about 250 MeV.

11. The synchrocyclotron of claim 10, wherein the energy of the particles that are output from the cavity is variable at a rate up to 20 MeV per second.

12. The synchrocyclotron of claim 1, wherein the energy of the particles that are output from the cavity is variable non-continuously between about 115 MeV and about 250 MeV.

13. The synchrocyclotron of claim 12, wherein the energy of the particles is variable at a step size of about 10 MeV to about 80 MeV.

14. The synchrocyclotron of claim 13, wherein each variation of the energy by one step takes less than 30 minutes.

15. The synchrocyclotron of claim 1, wherein the one or more coils comprises a superconducting coil.

16. The synchrocyclotron of claim 1, wherein each frequency range comprises a lower boundary and an upper boundary, and wherein the lower boundary is within a range of about 40 MHz to about 250 MHz, and the upper boundary is within a range of about 56 MHz to about 340 MHz.

17. The synchrocyclotron of claim 16, wherein the lower boundary is within a range of about 73 MHz to about 150 MHz, and the upper boundary is within a range of about 131 MHz to about 196 MHz.

18. The synchrocyclotron of claim 16, further comprising one or more reactive elements coupled to the voltage source to sweep the RF voltage over a frequency range.

19. The synchrocyclotron of claim 18, wherein the one or more reactive elements are configured to select the frequency range for a corresponding energy at which the particles are output from the cavity.

20. The synchrocyclotron of claim 19, wherein the one or more reactive elements comprise a variable capacitor or variable inductor.

21. The synchrocyclotron of claim 1, wherein the one or more coils comprises a first set of coils and a second set of coils, the first set of coils being superconducting and configured to receive a fixed portion of the electrical current, and the second set of coils being superconducting or non-superconducting and configured to receive a portion of the electrical current that is changeable to take on one of multiple values.

22. A proton therapy system comprising:
the synchrocyclotron of claim 1; and
a gantry on which the synchrocyclotron is mounted, the gantry being rotatable relative to a patient position;
wherein the particles are protons and the proton therapy system is configured to output the protons from the synchrocyclotron towards the patient position.

23. The synchrocyclotron of claim 1, further comprising:
one or more ferromagnetic rods that are movable relative to the magnetic pole pieces in order to affect a value of the magnetic field.

24. The synchrocyclotron of claim 23, wherein the one or more ferromagnetic rods are movable within at least one of the magnetic pole pieces.

25. A synchrocyclotron comprising:
a voltage source to provide a radio frequency (RF) voltage to a cavity to accelerate particles from a particle source;
coils comprising a first set of coils and a second set of coils, the first set of coils to pass a first portion of an electrical current, and the second set of coils to pass a second portion of the electrical current, the first portion being fixed and the second portion being changeable to take on one of multiple values, the coils to generate a magnetic field to cause the particles to move orbitally within the cavity, the magnetic field being at least 4 Tesla; and
an extraction channel to receive the particles from the cavity, and to output the particles from the synchrocyclotron.

26. The synchrocyclotron of claim 25, wherein the second portion of the electrical current is within a range that causes the magnetic field at an extraction radius of the synchrocyclotron to change by between about 5% and 35% of a maximum value of the magnetic field.

27. The synchrocyclotron of claim 26, wherein the magnetic field at the extraction radius is changeable by between about 0.2 Tesla and about 1.4 Tesla or between about 0.6 and about 4.2 Tesla.

28. The synchrocyclotron of claim 25, wherein the magnetic field has a magnitude having a range of about 4 Tesla to about 20 Tesla.

* * * * *